(12) United States Patent
Franklin et al.

(10) Patent No.: US 9,518,277 B2
(45) Date of Patent: Dec. 13, 2016

(54) **GENETICALLY ENGINEERED MICROBIAL STRAINS INCLUDING *CHLORELLA PROTOTHECOIDES* LIPID PATHWAY GENES**

(71) Applicant: TerraVia Holdings, Inc., South San Francisco, CA (US)

(72) Inventors: Scott Franklin, La Jolla, CA (US); Shane Brubaker, El Cerrito, CA (US); George N. Rudenko, Mountain View, CA (US); Riyaz Bhat, South San Francisco, CA (US); Matthew Shoa-Azar, San Mateo, CA (US); Aravind Somanchi, Redwood City, CA (US); Aren Ewing, South San Francisco, CA (US)

(73) Assignee: TerraVia Holdings, Inc., South San Francisco, CA (US)

(*) Notice: Subject to any disclaimer, the term of this patent is extended or adjusted under 35 U.S.C. 154(b) by 231 days.

(21) Appl. No.: 14/099,704

(22) Filed: Dec. 6, 2013

(65) Prior Publication Data

US 2014/0178950 A1   Jun. 26, 2014

Related U.S. Application Data

(60) Provisional application No. 61/734,613, filed on Dec. 7, 2012, provisional application No. 61/902,705, filed on Nov. 11, 2013.

(51) Int. Cl.
| | |
|---|---|
| *C12P 7/64* | (2006.01) |
| *C12N 15/52* | (2006.01) |
| *C07H 21/00* | (2006.01) |
| *C12N 1/13* | (2006.01) |
| *C12N 1/15* | (2006.01) |
| *C12N 1/21* | (2006.01) |
| *C12N 9/10* | (2006.01) |

(52) U.S. Cl.
CPC ............. *C12P 7/6463* (2013.01); *C12N 15/52* (2013.01)

(58) Field of Classification Search
CPC ................................ C12N 15/52; C12P 7/6463
See application file for complete search history.

(56) References Cited

U.S. PATENT DOCUMENTS

| | | | |
|---|---|---|---|
| 4,945,050 | A | 7/1990 | Sanford et al. |
| 5,900,370 | A | 5/1999 | Running |
| 6,395,965 | B1 | 5/2002 | Xia |
| 7,135,290 | B2 | 11/2006 | Dillon |
| 8,187,860 | B2 | 5/2012 | Franklin et al. |
| 8,258,109 | B2 | 9/2012 | Bennett et al. |
| 8,791,088 | B2 | 7/2014 | Bennett et al. |
| 8,951,308 | B2 | 2/2015 | Ellis et al. |
| 2004/0236091 | A1 | 11/2004 | Chicz et al. |
| 2009/0203093 | A1 | 8/2009 | Steinbuchel et al. |
| 2009/0211150 | A1 | 8/2009 | Wu et al. |
| 2010/0021912 | A1 | 1/2010 | Farese et al. |
| 2010/0151112 | A1 | 6/2010 | Franklin et al. |
| 2011/0015417 | A1* | 1/2011 | Trimbur ............... C10L 1/026  554/127 |
| 2011/0020889 | A1 | 1/2011 | Feldman et al. |
| 2011/0293785 | A1 | 12/2011 | Franklin et al. |
| 2011/0294174 | A1 | 12/2011 | Franklin et al. |
| 2012/0028319 | A1 | 2/2012 | Trimbur et al. |
| 2013/0197247 | A1 | 8/2013 | Franklin et al. |
| 2013/0280793 | A1 | 10/2013 | Brown et al. |
| 2013/0323780 | A1 | 12/2013 | Schneider et al. |

FOREIGN PATENT DOCUMENTS

| | | |
|---|---|---|
| WO | WO 2008/151149 A2 | 12/2008 |
| WO | WO 2009/105927 A1 | 9/2009 |
| WO | WO 2009/126843 A2 | 10/2009 |
| WO | WO 2010/045368 A2 | 4/2010 |
| WO | WO 2010/063031 A2 | 6/2010 |
| WO | WO 2010/063032 A2 | 6/2010 |
| WO | WO 2010/120939 A2 | 10/2010 |
| WO | WO 2010/147642 A1 | 12/2010 |
| WO | WO 2011/008565 A1 | 1/2011 |
| WO | WO 2011/150410 A2 | 12/2011 |
| WO | WO 2011/150411 A1 | 12/2011 |
| WO | WO 2012/106560 A1 | 8/2012 |
| WO | WO 2013/056212 A2 | 4/2013 |
| WO | WO 2013/082186 A2 | 6/2013 |
| WO | WO 2013/158938 A1 | 10/2013 |
| WO | WO 2014/089514 A1 | 6/2014 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Branch, A., TIBS 23:45-50, 1998; A good antisense molecule is hard to find.*
US Office Action, dated Jul. 30, 2015, issued in U.S. Appl. No. 13/688,025.
PCT Invitation to Pay Additional Fees and, Where Applicable, Protest Fee dated Apr. 12, 2013 issued in PCT/US2012/066893.
PCT International Search Report and Written Opinion dated Jul. 19, 2013 issued in PCT/US2012/066893.
PCT International Preliminary Report on Patentability dated Jun. 12, 2014 issued in PCT/US2012/066893.

(Continued)

*Primary Examiner* — Delia Ramirez
(74) *Attorney, Agent, or Firm* — Emily M. Haliday; Weaver Austin Villeneuve & Sampson LLP

(57) ABSTRACT

Genetically engineered microbial, e.g., *Chlorella protothecoides*, cells producing microbial oils are useful as a food additive and a source of renewable fuels and industrial chemicals. Lipid biosynthesis genes for *Auxenochlorella protethecoides* are disclosed that are useful for increasing lipid production and altering fatty acid and triacylglycerol profiles in recombinant microrganisms including cells of the genus *Auxenochlorella* or *Prototheca*.

10 Claims, No Drawings

(56) References Cited

OTHER PUBLICATIONS

Database Geneseq [Online] Aug. 5, 2010 "P. moriforims fatty acyl-ACP thioesterase-1 cDNA, SEQ:134.", retrieved from EBI accession No. GSN :AYC84244 Database accession No. AYC84244 sequence.
Database EMBL [Online] Sep. 17, 2010 "Chlorella variabilis hypothetical protein," retrieved from EBI accession No. EMBL:EFN58098 sequence, One page.
Chinese First Office Action dated Jul. 9, 2015 issued in CN 201280068060.6.
European Office Action dated Jul. 3, 2015 issued in EP 12 799 433.3.
European Office Action dated Sep. 10, 2015 issued in EP 12 799 433.3.
Mexican Office Action dated Jun. 30, 2014 issued in MX/a/2014/006357.
PCT International Search Report and Written Opinion dated Mar. 24, 2014 issued in PCT/US2013/073718.
Mexican Office Action dated Sep. 2, 2014 issued in MX/a/2014/006357.
PCT International Preliminary Report on Patentability and Written Opinion dated Jun. 18, 2015 issued in PCT/US2013/073718.
Abe et al., (2008) "Expression of Exogenous Genes Under the Control of Endogenous *HSP70* and *CAB* Promoters in the *Closterium peracerosum—strigosum—littorale* complex," *Plant Cell Physiology*, 49(4):625-632.
Abe et al., (2011) "Stable Nuclear Transformation of the *Closterium peracerosum—strigosum—littorale* Complex," *Plant & Cell Physiology*, 52(9):1676-1685.
Ando et al., (Sep. 2009) "Establishment of *Agrobacterium tumefaciens*—Mediated Transformation of an Oleaginous Fungus, *Mortierella alpina* 1S-4, and Its Application for Eicosapentaenoic Acid Producer Breeding," *Applied and Environmental Biology*, 75(17):5529-5535.
Apt et al., (1996) "Stable nuclear transformation of the diatom *Phaeodactylum tricornutum*," *Molecular and General Genetics*, 252:572-579.
Armbrust et al., (Oct. 1, 2004) "The Genome of the Diatom *Thalassiosira Pseudonana*: Ecology, Evolution, and Metabolism," *Science*, 306(5693):79-86.
Boyle et al., (May 4, 2012) "Three Acyltransferases and Nitrogen-responsive Regulator Are Implicated in Nitrogen Starvation-induced Triacylglycerol Accumulation in *Chlamydomonas*," *The Journal of Biological Chemistry*, 287(19):15811-15825.
Brown, L.M., (1982) "Production of axenic cultures of algae by an osmotic method," *Phycologia*, 21(3):408-410.
Cerutti et al., (Jan. 1997) "A Eubacterial Gene Conferring Spectinomycin Resistance on *Chlamydomonas reinhardtii*: Integration Into the Nuclear Genome and Gene Expression," *Genetics*,145(1):97-110.
Chen et al., (1988) "Recognition of prokaryotic transcription terminators by spinach chloroplast RNA polymerase," *Nucleic Acids Research*,16(17):8411-8431.
Chen et al., (2001) "Highly efficient expression of rabbit neutrophil peptide-1 gene in *Chlorella ellipsoidea* cells," *Current Genetics*, 39(5):365-370.
Cho et al., (2007) "Optimum temperature and salinity conditions for growth of green algae *Chlorella ellipsoidea* and *Nannochloris oculata*," *Fisheries Science*, 73(5):1050-1056.
Chow et al., (1999) "Electrotransformation of *Chlorella vulgaris*," *Plant Cell Reports*, 18:778-780.
Courchesne, Noémie Manuelle Dorval el al., (2009) "Enhancement of lipid production using biochemical, genetic and transcription factor engineering approaches," *Journal of Biotechnology*, 141(1):31-41.
Davidi, Lital, et al., (Published online Jan. 10, 2012) "Characterization of major lipid droplet proteins front Dunaliella," Department of Biological Chemistry, The Weizmann Institute of Science, Rehovot 76100, Israel, *Springer*, 15pp.
Dawson et al., (1997) "Stable Transformation of *Chlorella*: Rescue of Nitrate Reductase-Deficient Mutants with the Nitrate Reductase Gene," *Current Microbiol.*, 35(6):356-362.
Deng et al., (Feb. 4, 2011) "The effects of nutritional restriction on neutral lipid accumulation in *Chlamydomonas* and *Chlorella*," *African Journal of Microbiology Research*, 5(3):260-270.
El-Sheekh et al., (1999) "Stable transformation of the intact cells of *Chlorella kessleri* with high velocity microprojectiles," *Biologia Plantarium*, 42:(2):209-216.
Ewing et al., (2014) "16S and 23S Plastid RDNA Phylogenies of *Prototheca* Species and Their Auxanographic Phenotypes," *J Phycol.*,50(4):765-769, Epub Jul. 10, 2014.
Ewing et al., (2013) "Whole genome sequencing and phylogeny for members of the microalgae genus *Prototheca*," Abstract and Poster presented on Nov. 12, 2013 at the *Functional and Comparative Genomics & Pharmacogenomics Conference in Chicago*, 2pp.
Fromm et al., (Sep. 1985) "Expression of genes transferred into monocot and dicot plant cells by electroporation," *Proc. Natl. Acad. Sci. USA*, 82:5824 5828.
Gao et al. (Jul. 10, 2014) "Oil accumulation mechanisms of the oleaginous microalga *Chlorella protothecoides* revealed through its genome, transcriptomes, and proteomes," *BMC Genomics*, 15:582, 14pp.
Hallmann et al., (Nov. 1994) "Reporter genes and highly regulated promoters as tools for transformation experiments in *Volvox carteri*," *Proc. Natl. Acad. Sci. USA*, 91:11562-11566.
Hawkins et al., (1999) "Expression of Human Growth Hormone by the Eukaryotic Alga, *Chlorella*," *Current Microbiology*, 38:335-341.
Hickenbottom, S.L., et al., (Jul. 2004) "Structure of a Lipid Droplet Protein: The PAT Family Member TIP47," *Structure*, 12:1199-1207.
Holder et al., (Sep. 2011) "Comparative and Functional Genomics of *Rhodococcus opacus* PD630 for Biofuels Development," *PLOS Genetics*, 7(9):e1002219, 18pp.
Huang et al. (2006) "Expression of mercuric reductase from *Bacillus megaterium* MB1 in eukaryotic microalga *Chlorella* sp. DT: an approach for mercury phytoremediation," *Appl. Microbiol. Biotechnol.* 72:197-205.
Iglesias-Prieto et al., (Nov. 1992) "Photosynthetic response to elevated temperature in the symbiotic dinoflagellate *Symbiodinium microadriaticum* in culture," *Proceedings of the National Academy of Sciences*, 89(21):10302-10305.
Jakobiak et al. (Dec. 2004) "The Bacterial Paromomycin Resistance Gene, *aphH*, as a Dominant Selectable Marker in *Volvox carteri*," *Protist*,155(4):381-393.
Jarvis et al. (1991) "Transient expression of firefly luciferase in protoplasts of the green alga *Chlorella ellipsoidea*," *Current Genetics*, 19:317-321.
Kalscheuer et al., (1999) "Establishment of a gene transfer system for *Rhodococcus opacus* PD630 based on electroporation and its application for recombinant biosynthesis of poly(3-hydroxyalkanoic acids)," *Applied and Environmental Microbiology*, 52:508-515.
Kang et al., (2004) "Genetic diversity in chlorella viruses flanking *kcv*, a gene that encodes a potassium ion channel protein," *Virology*, 326(1):150-159.
Kawasaki et al., (2004) "Immediate early genes expressed in chlorovirus infections," *Virology*, 318(1):214-223.
Kilian et al., (Dec. 27, 2011) "High-efficiency homologous recombination in the oil-producing alga *Nannochloropsis* sp.," *Proceedings of the National Academy of Sciences*, 108(52):21265-21269.
Kim et al., (2002) Stable Integration and Functional Expression of Flounder Growth Hormone Gene in Transformed Microalga, *Chlorella ellipsoidea, Mar. Biotechnol.*, 4(1):63-73.
Kobayashi et al., (Mar. 1993) "Enhanced Carotenoid Biosynthesis by Oxidative Stress in Enhanced Carotenoid Biosynthesis by Oxidative Stress in Acetate-Induced Cyst Cells of a Green Unicellular Alga, *Haematococcus pluvialis*," *Applied and Environmental Microbiology*, 59(3):867-873.
Lerche et al., (2009) "Stable nuclear transformation of Gonium pectorale," *BMC Biotechnology*, 9(64):21pp.

(56) References Cited

OTHER PUBLICATIONS

Levitan et al., (Apr. 26, 2005) "Dual targeting of the protein disulfide isomerase RB60 to the chloroplast and the endoplasmic reticulum," *Proc. Natl. Acad. Sci. USA*,102(17):6225-6230.

Low, K.L., et al., (Jul. 2010) "Lipid Droplet-associated Proteins Are Involved in the Biosynthesis and Hydrolysis of Triacylglycerol in *Mycobacterium bovis* Bacillus Calmette-Guérin," *The Journal of Biological Chemistry*, 285(28):21662-21670.

Lumbreras et al., (1998) "Efficient foreign gene expression in *Chlamydomonas reinhardtii* mediated by an endogenous intron," *Plant Journal*, 14(4):441-447.

Mackenzie et al., (Nov. 2000) "Isolation and Use of a Homologous Histone H4 Promoter and a Ribosomal DNA Region in a Transformation Vector for the Oil-Producing Fungus *Mortierella alpina*," *Applied and Environmental Microbiology*, 66(11):4655-4661.

Merchant et al., (Oct. 12, 2007) "The *Chlamydomonas* Genome Reveals the Evolution of Key Animal and Plant Functions," *Science*, 318(5848):245-250.

Mitra et al., (Oct. 14, 1994) "A Chlorella Virus Gene Promoter Functions as a Strong Promoter Both in Plants and Bacteria," *Biochemical Biophysical Research Communication*, 204(1):187-194.

Mitra et al., (Oct. 1994) "The *Chlorella* virus adenine methyltransferase gene promoter is a strong promoter in plants," *Plant Mol. Biol.*, 26(1):85-93.

Moellering, E.R., et al., (Jan. 1, 2010) "RNA Interference Silencing of a Major Lipid Droplet Protein Affects Lipid Droplet Size in *Chlamydomonas reinhardtii*", *Eukaryotic Cell*, 9(1):97-106.

Peled et al. (2011) "Isolation of a Novel Oil Globule Protein from the Green Alga *Haematococcus pluvialis* (Chlorophyceae)," *Lipids*, 46(9):851-861.

Pignede et al., (Aug. 2000) "Autocloning and Amplification of *LIP2* in *Yarrowia lipolytica*," *Applied and Environmental Biology*, 66(8):3283-3289.

Pore, (Oct. 1973) "Selective Medium for the Isolation of *Prototheca*," *App. Microbiology*, 26(4):648-649.

Poulsen et al., (2005) "A new molecular tool for transgenic diatoms Control of mRNA and protein biosynthesis by an inducible promoter-terminator cassette," *FEBS Journal*, 272:3413-3423.

Prochnik et al., (Jul. 9, 2010) "Genomic Analysis of Organismal Complexity in the Multicellular Green Alga *Volvox carteri*," *Science*, 329:223-226.

Pröschold et al., (Aug. 2005) "Portrait of a species: *Chlamydomonas reinhardtii*," *Genetics*,170:1601-1610.

Radakovits et al., (Apr. 2010) "Genetic Engineering of Algae for Enhanced Biofuel Production," *Eukaryotic Cell*, 9(4):486-501.

Radakovits et al., (Feb. 21, 2012) "Draft genome sequence and genetic transformation of the oleaginous alga *Nannochloropsis gaditana*," *Nature Communications*, 3:686 Article No. 10.1038, 10 pages.

Robenek et al., (2011) "Topography of Lipid Droplet-Associated Proteins: Insights from Freeze-Fracture Replica Immunogold Labeling," *Journal of Lipids*, vol. 2011, Article ID 409371, 10 pages.

Rosenberg, Julian N. et al., (2008) "A green light for engineered algae: redirecting metabolism to fuel a biotechnology revolution," *Current Opinion in Biotechnology*, 19(5):430-436.

Sanford, (Dec. 1988) "The biolistic process," *Trends in Biotech.* 6:299-302.

Schultz et al., (Apr. 2005) "A common core of secondary structure of the internal transcribed spacer 2 (ITS2) throughout the Eukaryota," *RNA*, 11(4):361-364.

Sekimoto et al., (2003) "Expressed Sequence Tags from the *Closterium peracerosum-strigosum-littorale* complex, a Unicellular Charophycean Alga, in the Sexual Reproduction Process," *DNA Research*, 10(4):147-153.

Steinbrenner et al., (Dec. 2006) "Transformation of the Green Alga *Haematococcus pluvialis* with a Phytoene Desaturase for Accelerated Astaxanthin Biosynthesis," *Applied and Environmental Microbiology*, 72(12):7477-7484.

Tan et al., (Aug. 2005) "Establishment of a Micro-Particle Bombardment Transformation System for *Dunaliella salina*," *The Journal of Microbiology*, 43(4):361-365.

Vieler et al., (Apr. 2012) "A Lipid Droplet Protein of *Nannochloropsis* with Functions Partially Analogous to Plant Pleosins," *Plant Physiology*, 158:1562-1569.

Walker et al., (2005) "Characterisation of the *Dunaliella tertiolecta RbcS* genes and their promoter activity in *Chlamydomonas reinhardtii*," *Plant Cell Rep.* 23(10-11):727-735.

Wang et al., (Dec. 2011) "Genome Characterization of the Oleaginous Fungus *Mortierella alpina*," *PLOS One*, 6(12):e28319, 16pp.

Wu et al., (2001) "Identification of *Chlorella* spp. isolates using ribosomal DNA sequences," *Bot. Bull. Acad. Sin*.42:115-121.

Yan et al., (2015) "*Auxenochlorella protothecoides* and *Prototheca wickerhamii* plastid genome sequences give insight into the origins of non-photosynthetic algae," *Scientific Reports*, 5:14465, 8pp.

Yang et al., (2010) "Identification of Perilipin-2 as a lipid droplet protein regulated in oocytes during maturation," *Reproduction, Fertility and Development*, 22:1262-1271.

Yang et al., (2012) "Controlling the size of lipid droplets: lipid and protein factors," *Current Opinion in Cell Biology*, 24:509-516.

Zaslavskaia et aL (Jun. 15, 2001) "Trophic Conversion of an Obligate Photoautotrophic Organism Through Metabolic Engineering," *Science*, 292:2073-2075.

Hypothetical protein CHLNCDRAFT_27559 [Chlorella variabilis] Chorella variabilis protein sequence. Genbank Id: XP_005843858. 1, Oct. 28, 2013.

US Notice of Allowance, dated Jan. 4, 2016, issued in U.S. Appl. No. 13/688,025.

European Extended Search Report dated Mar. 8, 2016 issued in EP 13 85 9876.

Database UniProt [Online] Nov. 28, 2012 Najihah et al.: "Isolation and partial characterization of beta ketoacyl-ACP synthase I (KAS I) cDNA clone from *Chlorella* sp.," retrieved from Database accession No. B2Z3P6 sequence, 213 AA, One page.

Chen et al., (2011) "Structural classification and properties of ketoacyl synthases," *Protein Science*, 20:1659-1667.

Chen et al., (2012) "Prediction of ketoacyl synthase family using reduced amino acid alphabets," *Journal of Industrial Microbiology and Biotechnology*, 39:579-584.

Lennen et al., (Oct. 23, 2012) "Engineering *Escherichia coli* to synthesize free fatty acids," *Trends in Biotechnology*, 30:659-667.

Mackintosh et al., (1989) "A new assay procedure to study the induction of β-ketoacyl-ACP synthase I and II, and the complete purification of β-ketoacyl-ACP synthase I from developing seeds of oilseed rape (*Brassica napus*)," *Biochimica Et Biophysica Acta*, 1002:114-124.

NN: (2010) "Research grants, 2010," Universiti Malaysia Terengganu Research Management Center / Project description (only one page is cited), Retrieved from the Internet on Feb. 8, 2016 at http://rmc.umt.edu.my/?page_id=239, 2pp.

Torella et al., (Jul. 9, 2013) "Tailored fatty acid synthesis via dynamic control of fatty acid elongation," *Proceedings of the National Academy of Sciences, U.S.A.*, 110(28):11290-11295.

\* cited by examiner

GENETICALLY ENGINEERED MICROBIAL STRAINS INCLUDING *CHLORELLA PROTOTHECOIDES* LIPID PATHWAY GENES

CROSS-REFERENCE TO RELATED APPLICATIONS

This application claims the benefit under 35 U.S.C. 119(e) of U.S. Provisional Patent Application No. 61/734,613, filed Dec. 7, 2012 and U.S. Provisional Patent Application No. 61/902,705, filed Nov. 11, 2013. Each of these applications is incorporated herein by reference in its entirety for all purposes.

REFERENCE TO A SEQUENCE LISTING

This application includes a sequence listing which has been submitted electronically in ASCII format and is hereby incorporated by reference in its entirety. Said ASCII copy, created on Dec. 6, 2013, is named SOLAP016US_SL.txt and is 78,185,624 bytes in size.

FIELD OF THE INVENTION

The present disclosure relates to genetically engineered microbes and to biofuels and bioproducts derived from the microbes, and thus find uses in the fields of microbiology, molecular biology, and chemistry, and in food, fuel, and industrial chemicals production. Certain aspects of the disclosure relate to polynucleotides, expression vectors, expression cassettes and host cells comprising coding sequences from the microalgae *Auxenochlorella protothecoides* (also known in the literature as *Chlorella protothecoides*). These terms may be used interchangeably.

DESCRIPTION OF RELATED DISCLOSURES

Microalgae, including genetically engineered microalgae, have been identified as important new sources of oil for use in food and fuels. See PCT Pub. Nos. WO 2008/151149, WO 2009/126843, and WO 2010/045368, each of which is incorporated herein by reference in its entirety for all purposes. *Auxenochlorella protothecoides* finds use in food and fuels (see: Safety evaluation of Whole Algalin Protein (WAP from *Chlorella protothecoides*, Szabo et al, *Food and Chemical Toxicology*, Vol 59, September 2013, pp. 34-45). While *Auxenochlorella* strains have been the focus of much effort in developing microbial oil production methods, more recently strains of the genus *Prototheca* have been identified as also having promise as a new source of microbial oils, including tailored oils for specific applications. See PCT Pub. Nos. WO 2010/063031, WO 2010/063032, WO 2011/150410, WO 2012/106560, and WO2013/158938, each of which is incorporated herein by reference in its entirety for all purposes. WO/2013/056212 discloses genes for optimization of productivity including photosynthesis genes. WO/2009/105927 discloses high-density fermentation methods for *Chlorella protothecoides* using heterotrophic culture. US20090211150 discloses methods for producing biodiesel from *Chlorella protothecoides*.

SUMMARY

In certain embodiments, the invention provides a recombinant (e.g., isolated) nucleic acid comprising a coding sequence that encodes a *Chlorella protothecoides* lipid biosynthesis protein or portion thereof. In some embodiments, provided is a recombinant nucleic acid comprising a coding sequence that encodes a *Chlorella protothecoides* lipid biosynthesis protein, provided that the protein is not stearoyl acyl carrier protein desaturase. In some embodiments the protein is not a stearol acyl carrier protein desaturase of SEQ ID NO: 49107 (coding sequence SEQ ID NO: 49108). In some embodiments, the coding sequence is in operable linkage with a promoter, an untranslated control element, and/or a targeting sequence, such as a plastidial targeting sequence and/or mitochondrial targeting sequence. The recombinant nucleic acid may be, e.g., a DNA molecule. In certain embodiments, the recombinant nucleic acid is an expression vector. The recombinant nucleic acid can, for example, include an expression cassette that encodes an mRNA that encodes a functional *Chlorella protothecoides* lipid biosynthesis enzyme. Alternatively or in addition, the recombinant nucleic acid can include an expression cassette that encodes an inhibitory RNA that suppresses expression of a *Chlorella protothecoides* lipid biosynthesis gene. In some embodiments, the lipid biosynthesis protein is a protein in Table 1. In some embodiments, the protein has at least 50%, 60%, 70%, 80%, 85%, 90% or 95% sequence identity to a protein provided herein or a protein encoded by a gene provided herein. In some embodiments the protein or the gene encoding the protein is listed in Table 1.

In some embodiments, the protein encoded by the coding sequence in the nucleic acid contains one or more point mutations, deletions, substitutions, or combinations thereof. In other embodiments, the protein has at least one point mutation in comparison to a protein in Table 1. In some embodiments, the protein encoded by the coding sequence is a functional protein. In some embodiments, the protein is diacylglycerol diacyltransferase (DGAT) having at least one point mutation. In other embodiments, the recombinant nucleic acid further encodes sucrose invertase.

In certain embodiments, also provided is a genetically engineered microbial cell transformed with a recombinant nucleic acid provided herein. In some embodiments, the cell is a microbial, plant, or yeast cell. In particular embodiments, provided is a cell comprising one or more exogenous gene(s), wherein the exogenous gene is a *Chlorella protothecoides* lipid biosynthesis gene selected from the genes listed in Table 1. The genetically engineered microbial cell can, for example, be a cell of the genus *Prototheca* or *Chlorella*. In particular embodiments, the cell comprises both an endogenous lipid biosynthesis gene and one or more exogenous *Chlorella protothecoides* lipid biosynthesis gene(s) selected from the genes listed in Table 1. In certain embodiments, the exogenous gene can encode a lipid biosynthesis protein, wherein the amino acid sequence of the lipid biosynthesis protein is identical to the endogenous lipid biosynthesis protein. For example, the exogenous gene can include a nucleotide sequence in which the codons of the nucleotide sequence encoding the amino acids of the lipid biosynthesis protein have been altered, as compared to the codons in the native nucleic acid. In various embodiments, the exogenous gene can encode a protein with at least 50%, 60%, 70%, 75%, 80%, 85%, 90%, 95%, 96%, 97%, 98%, or 99% amino acid identity to the native *Chlorella protothecoides* protein. The exogenous gene can, in some embodiments, be in operable linkage with a promoter element that is not the native *Chlorella protothecoides* promoter, an untranslated control element that is not the native *Chlorella protothecoides* untranslated control element, and/or a nucleotide sequence encoding a transit peptide that is not the native *Chlorella protothecoides* transit peptide. The transit peptide can, for example, be a plastidial targeting sequence or a mitochondrial targeting sequence. In certain embodiments, the cell has a 23S rRNA sequence with at least 75%, 80%, 85%, 90%, 95%, 96%, 97%, 98%, or 99% nucleotide identity to SEQ ID NO: 60. In some embodiments, the cell is a *Chlorella* cell. In particular embodiments, the cell is a *Prototheca* cell, wherein the cell has a fatty acid profile that is at least 10% C8-C14.

In certain embodiments, another aspect of the invention is a method for obtaining microbial oil comprising culturing a genetically engineered cell, e.g., a *Chlorella* cell, described above under conditions such that oil is produced. In certain embodiments, the microbial oil thus produced has a fatty acid profile that is at least 10% C8-C14. The invention also includes a microbial oil produced by this method.

In some embodiments provided is a microbial oil obtained from a cell provided herein.

In some cases, the microbial oil is a microalgal oil comprising C29 and C28 sterols, wherein the amount of C28 sterols is greater than C29 sterols.

In some cases, the microbial oil is a microalgal oil comprising one or more of: at least 10% ergosterol; ergosterol and β-sitosterol, wherein the ratio of ergosterol to β-sitosterol is greater than 25:1; ergosterol and brassicasterol; ergosterol, brassicasterol, and poriferasterol, and wherein the oil is optionally free from one or more of β-sitosterol, campesterol, and stigmasterol.

In particular embodiments, the invention provides genetically engineered cell, e.g., of the genus *Chlorella*, wherein the activity of one or more endogenous lipid biosynthesis gene, selected from the genes listed in Table 1, has been attenuated. In various embodiments, the activity of the endogenous gene has been attenuated through chromosomal gene deletion, chromosomal gene insertion, frameshift mutation, point mutation, and/or inhibitory RNA. The genetically engineered cell can, in certain embodiments, further comprise an exogenous *Chlorella protothecoides* lipid biosynthesis pathway gene selected from the genes listed in Table 1. In particular embodiments, one or more allele(s) of an endogenous lipid biosynthesis gene in the genetically engineered cell is attenuated.

In certain embodiments, one allele of the endogenous lipid biosynthesis gene is replaced, in the genetically engineered cell, with a polynucleotide encoding, e.g., an exogenous *Chlorella protothecoides* lipid biosynthesis pathway gene selected from Table 1 and a selectable marker. In a variation of this embodiment, two or more alleles of the endogenous lipid biosynthesis gene are each replaced with a polynucleotide encoding an exogenous *Chlorella protothecoides* lipid biosynthesis pathway gene selected from Table 1 and a selectable marker. In certain embodiments, the genetically engineered cell has a 23S rRNA sequence with at least 75%, 80%, 85%, 90%, 95%, 96%, 97%, 98%, or 99% nucleotide identity to SEQ ID NO: 60 or SEQ ID NO 5. In particular embodiments, the genetically engineered cell is a *Chlorella* or *Prototheca* cell, wherein the cell has a fatty acid profile that is at least 10% C8-C14. In some embodiments, the cell has a fatty acid profile that is at least at least 50%, 60%, or 70% C12:0. In some embodiments, the cell has a fatty acid profile that is at least at least 70%, 75%, 80%, 85%, or 90% C18:1. In certain embodiments, the invention also provides a method for obtaining microbial oil comprising culturing this genetically engineered cell, which may be, e.g., a *Chlorella* or *Prototheca* cell, under conditions such that oil is produced. In certain embodiments, the microbial oil thus produced has a fatty acid profile that is at least 10% C8-C14. The invention also includes a microbial oil produced by this method.

In another aspect, the present invention provides a genetically engineered microbial cell, e.g., *Chlorella* or *Prototheca* cell, in which one or more lipid biosynthesis genes have been modified to increase or decrease expression of such one or more genes such that the fatty acid profile of the genetically engineered strain differs from that of the strain from which it was derived. In one embodiment, at least two genes have been modified. In various embodiments, the genetic modifications include one or more of the following modifications: (i) attenuation of a gene or its enzymatic product; and (ii) increased expression of a gene or its enzymatic product; (iii) altered activity of a gene or its enzymatic product.

In various embodiments, the genetically engineered cell has one or more attenuated genes, wherein the genes attenuated have been attenuated by a means selected from the group consisting of a homologous recombination event and introduction of an exogenous gene that codes for an interfering RNA. In various embodiments, one or more alleles of a gene are attenuated. In some embodiments, genes are attenuated to reduce unwanted side products e.g. starch, cell membranes, or other cellular components.

In various embodiments, the genetically engineered cell has one or more over-expressed genes, wherein the genes over-expressed have been up-regulated by a means selected from the group consisting of introduction of additional copies of said gene into said cell; introduction of new expression control elements for said gene; and alteration of the protein-coding sequence of the gene. In various embodiments, one or more alleles of a gene are over-expressed. In various embodiments, manipulation of gene expression results in improved lipid productivity, oil per cell, and yield per g of sugar. In some embodiments, the cell cycle is manipulated to produce larger cells containing an increased volume of oil. In some embodiments, sugar uptake and other aspects of cellular metabolism are enhanced.

In various embodiments, the modified genes of the genetically engineered cell are selected from the group consisting of *Chlorella protothecoides* lipid biosynthesis genes presented in Table 1. In various embodiments, the genetically engineered cell comprises an exogenous gene selected from the group consisting of *Chlorella protothecoides* lipid biosynthesis genes presented in Table 1. In various embodiments, the genetically engineered cell comprises one or more over-expressed alleles of a gene, the gene selected from the group consisting of *Chlorella protothecoides* lipid biosynthesis genes presented in Table 1. In various embodiments, the genetically engineered cell has an attenuated gene selected from the group consisting of *Chlorella protothecoides* lipid biosynthesis genes presented in Table 1. In various embodiments, the genetically engineered cell has one more attenuated alleles of a gene, the gene selected from the group consisting of *Chlorella protothecoides* lipid biosynthesis genes presented in Table 1.

In various embodiments, the genetically engineered cell has a fatty acid profile selected from the group consisting of: 3% to 60% C8:0, 3% to 60% C10:0, 3% to 70% C12:0, 3% to 95% C14:0, 3% to 95% C16:0, 3% to 95% C18:0, 3% to 95% C18:1, 0% to 60% C18:2, 0% to 60% C18:3 or combinations thereof. In various embodiments, the ratio of C10:0 to C12:0 is at least 3:1. In some cases, the ratio of C10:0 to C14:0 is at least 10:1. In various embodiments, the ratio of C12:0 to C14:0 is at least 3:1. In various embodiments, the genetically engineered cell has a fatty acid profile of at least 40% saturated fatty acids, of at least 60% saturated fatty acids, or at least 85% saturated fatty acids.

In another aspect, the present invention provides methods for obtaining microbial oil comprising culturing a genetically engineered *Chlorella* cell of the invention under conditions such that oil is produced. In various embodiments, the microbial oil has a fatty acid profile selected from the group consisting of: 3% to 40% C8:0, 3% to 60% C10:0, 3% to 70% C12:0, 3% to 95% C14:0, 3% to 95% C16:0, 3% to 95% C18:0, 3% to 95% C18:1, 0% to 60% C18:2, 0% to 60% C18:3 or combinations thereof. In various embodiments, the ratio of C10:0 to C12:0 is at least 3:1. In some cases, the ratio of C10:0 to C14:0 is at least 10:1. In various embodiments, the ratio of C12:0 to C14:0 is at least 3:1. In various embodiments, the genetically engineered cell has a fatty acid profile of at least 40% saturated fatty acids, of at least 60% saturated fatty acids, or at least 85% saturated fatty acids.

In an additional aspect, the present invention provides microbial oils and foods, fuels, and chemicals containing said oil or a chemical derived therefrom.

In another aspect, the present invention provides recombinant nucleic acids useful in methods for making genetically modified *Chlorella* and other cells. The nucleic acids of the invention comprise all or some portion of a *Chlorella protothecoides* lipid biosynthesis gene.

In various embodiments, these nucleic acids include expression cassettes, which consist of a coding sequence and control sequences that regulate expression of the coding sequence, which may code for an mRNA that encodes a lipid biosynthesis protein, enzyme, or for an RNAi that acts to suppress expression of a lipid biosynthesis gene.

In other embodiments, these nucleic acids are expression vectors that include one or more expression cassettes and stably replicate in a *Chlorella* or other host cell, either by integration into chromosomal DNA of the host cell or as freely replicating vectors.

In other embodiments, these nucleic acids comprise only a portion of a *Chlorella protothecoides* lipid biosynthesis gene, which portion may be a portion of a coding sequence, an exon, or a control element. Such nucleic acids are useful in the construction of expression cassettes for *Chlorella* and non-*Chlorella* host cells, for integration of exogenous DNA into *Chlorella* host cells, and for construction of nucleic acids useful for attenuating *Chlorella* lipid biosynthetic genes by homologous recombination.

In some embodiments, provided are sequences, compositions, host cells, and methods for overexpression of a lipid biosynthesis gene. In some aspects, the overexpressed lipid biosynthesis gene is one or more of LEC2, DGAT, ATP:citrate lyase (ACL), malic enzyme, lipase, fatty acyl-CoA reductase, Acyl-CoA Binding Proteins (ACBPs), or Lipoic Acid Synthase (LS1).

These and other aspects and embodiments of the invention are described in the detailed description of the invention below, and are exemplified in the examples below. Any or all of the features discussed above and throughout the application can be combined in various embodiments of the present invention.

DETAILED DESCRIPTION

Section I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

A nucleic acid "active in microalgae" refers to a nucleic acid that is functional in microalgae. For example, a promoter that has been used to drive an antibiotic resistance gene to impart antibiotic resistance to a transgenic microalgae is active in microalgae.

"Acyl carrier protein" or "ACP" is a protein that binds a growing acyl chain during fatty acid synthesis as a thiol ester at the distal thiol of the 4'-phosphopantetheine moiety and comprises a component of the fatty acid synthase complex.

"Acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Allele" refers to one or two or more forms of a gene or genetic locus. Alleles of a gene may share 100% or less nucleotide sequence identity. Gene products encoded by alleles of a gene may share 100% or less amino acid sequence identity. Overexperession of different alleles of a gene and/or the gene products encoded therein may confer different phenotypes to a genetically engineered organism. Attenuation of different alleles of a gene and/or the gene products encoded therein may confer different phenotypes to a genetically engineered organism.

"Attenuation of a Gene" refers to (i) genetically engineering a gene so that it has, relative to a wild-type gene, different control sequences that result in decreased amounts of a gene product (RNA including mRNA, inhibitory RNA molecules, and other RNAs, polypeptides); (ii) genetically engineering a cell so that it has, relative to a wild-type cell, fewer or no detectable copies of a gene and decreased amounts of the corresponding gene product; and/or (iii) genetically engineering the coding sequence of a gene to either decrease the stability and/or activity of the gene product (i.e., if the increase the stability of an RNA gene product, increase translation of an mRNA gene product, and/or decrease the level of enzymatic activity of a protein encoded by the mRNA gene product, i.e., by making the protein less stable or less active (which may also be referred to as "attenuation of an Enzymatic Product"). An "Attenuated Gene Product" is the gene product of attenuation of a gene by any of the foregoing methods. An "Attenuated Gene" is a gene that has been genetically engineered by one or more of the methods described herein that results in decreased amounts of gene product. Attenuation of a gene thus results in "Decreased Expression of a Gene", "downregulation of the gene", or "inactivation of the gene".

"Axenic" is a culture of an organism substantially free from contamination by other living organisms.

"Biomass" is material produced by growth and/or propagation of cells. Biomass may contain cells and/or intracellular contents as well as extracellular material, includes, but is not limited to, compounds secreted by a cell.

"Catalyst" is an agent, such as a molecule or macromolecular complex, capable of facilitating or promoting a chemical reaction of a reactant to a product without becoming a part of the product. A catalyst increases the rate of a reaction, after which, the catalyst may act on another reactant to form the product. A catalyst generally lowers the overall activation energy required for the reaction such that it proceeds more quickly or at a lower temperature. Thus, a reaction equilibrium may be more quickly attained. Examples of catalysts include enzymes, which are biological catalysts; heat, which is a non-biological catalyst; and metals used in fossil oil refining processes.

"Co-culture", and variants thereof such as "co-cultivate" and "co-ferment", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Coding Sequence" refers to that portion of a gene or expression cassette that encodes the RNA transcribed from that gene or expression cassette in a cell, specifically that portion of the mRNA that is translated into the protein encoded by that mRNA. Any non-translated portions of a gene between translated portions are referred to as "introns".

"Cofactor" or "co-factor" is any molecule, other than the substrate, required for an enzyme to carry out its enzymatic activity.

"Complementary DNA" or "cDNA" is a DNA copy of mRNA, usually obtained by reverse transcription of messenger RNA (mRNA) or amplification (e.g., via polymerase chain reaction ("PCR")).

"Control Sequence" refers to nucleic acid sequences in a gene or expression cassette that regulate transcription of a coding sequence and so include promoters, enhancers, transcription termination sequences, and translation initiation sequences.

"Cultivated", and variants thereof such as "cultured" and "fermented", refer to the intentional fostering of growth (increases in cell size, cellular contents, and/or cellular activity) and/or propagation (increases in cell numbers via mitosis) of one or more cells by use of selected and/or controlled conditions. The combination of both growth and propagation may be termed proliferation. Examples of selected and/or controlled conditions include the use of a defined medium (with known characteristics such as pH, ionic strength, and carbon source), specified temperature, oxygen tension, carbon dioxide levels, and growth in a bioreactor. Cultivate does not refer to the growth or propagation of microorganisms in nature or otherwise without human intervention; for example, natural growth of an organism that ultimately becomes fossilized to produce geological crude oil is not cultivation.

"Cytolysis" is the lysis of cells in a hypotonic environment. Cytolysis is caused by excessive osmosis, or movement of water, towards the inside of a cell (hyperhydration). The cell cannot withstand the osmotic pressure of the water inside, and so it explodes.

"Delipidated meal" and "delipidated microbial biomass" is microbial biomass after oil (including lipids) has been extracted or isolated from it, either through the use of mechanical (i.e., exerted by an expeller press) or solvent extraction or both. Delipidated meal has a reduced amount of oil/lipids as compared to before the extraction or isolation of oil/lipids from the microbial biomass but does contain some residual oil/lipid.

"Desaturase" are enzymes in the lipid synthesis pathway responsible for the introduction of double bonds (unsaturation) into the fatty acid chains of fatty acid or triacylglyceride molecules. Examples include but are not limited to stearoyl-Acyl carrier protein desaturase (SAD) and fatty acid desaturase (FAD), also known as fatty acyl desaturase.

"Expression Cassette" refers to a coding sequence and a promoter, optionally in combination with one or more control sequences. Expression cassettes for enzymes include, for example and without limitation, a translation initiation control sequence.

"Expression vector" or "expression construct" or "plasmid" or "recombinant DNA construct" refer to a nucleic acid that has been generated via human intervention, including by recombinant means or direct chemical synthesis, with a series of specified nucleic acid elements that permit transcription and/or translation of a particular nucleic acid in a host cell. The expression vector may be part of a plasmid, virus, or nucleic acid fragment. Typically, the expression vector includes a nucleic acid to be transcribed operably linked to a promoter. Some expression cassettes are expression vectors, but expression vectors often contain more than one expression cassette, for example expression cassettes for selectable markers are sometimes included in expression vectors for introducing exogenous genes into host cells. One of skill in the art understands that a "recombinant nucleic acid" that encodes a particular gene, or portion thereof, is isolated from the specific context in which it naturally occurs.

"Exogenous gene" is a nucleic acid that codes for the expression of an RNA and/or protein that has been introduced ("transformed") into a cell, and is also referred to as a "transgene". A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Exogenously provided" refers to a molecule provided to the culture media of a cell culture.

"Expeller pressing" is a mechanical method for extracting oil from raw materials such as soybeans and rapeseed. An expeller press is a screw type machine, which presses material through a caged barrel-like cavity. Raw materials enter one side of the press and spent cake exits the other side while oil seeps out between the bars in the cage and is collected. The machine uses friction and continuous pressure from the screw drives to move and compress the raw material. The oil seeps through small openings that do not allow solids to pass through. As the raw material is pressed, friction typically causes it to heat up.

"Fatty acids" shall mean free fatty acids, fatty acid salts, or fatty acyl moieties in a glycerolipid.

"Fatty acid modification enzyme" or "fatty acid modifying enzyme" refers to an enzyme that alters the covalent structure of a fatty acid. Examples of fatty acid modification enzymes include lipase, fatty acyl-CoA/aldehyde reductase, fatty acyl-CoA reductase, fatty aldehyde reductase, fatty aldehyde decarbonylase.

"Fatty acid profile" refers to the distribution of fatty acids in a cell or oil derived from a cell in terms of chain length and/or saturation pattern. In this context the saturation pattern can comprise a measure of saturated versus unsaturated acid or a more detailed analysis of the distribution of the positions of double bonds in the various fatty acids of a cell. The fatty acid profile in be readily determined, for example by using gas chromatography. In one method, the fatty acids of the triacylglycerol are converted into a fatty acid methyl ester (FAME) using well known methods. The FAME molecules are then detected by gas chromatography. For example, a separate peak is observed for a fatty acid of 14 carbon atoms with no unsaturation (C14:0) compared to any other fatty acid such as C14:1. The peak area for each class of FAME determined using GC-FID is proportional to the weight percentages of the fatty acids. Unless specified otherwise, the fatty acid profile is expressed as a weight percent of the total fatty acid content. When referring to fatty acid profiles, "at least 4% C8-C14" means that at least 4% by weight of the total fatty acids in a cell or in an extracted glycerolipid composition have a chain length that includes 8, 10, 12 or 14 carbon atoms.

"Fatty acid synthesis enzyme" refers to an enzyme that alters the chain length, saturation, or functional group modification of a fatty acid, or can otherwise lead to an altered fatty acid profile in a cell. Examples of fatty acid synthesis enzymes include fatty acyl-ACP thioesterase, desaturase, including stearoyl acyl carrier protein desaturase (SAD) and fatty acyl destaurase (FAD), fatty acyl hydroxylase, and β-keto-acyl-ACP synthase.

"Fatty acyl-ACP thioesterase" is an enzyme that catalyzes the cleavage of a fatty acid from an acyl carrier protein (ACP) during fatty acid synthesis.

"Fatty acyl-CoA/aldehyde reductase" is an enzyme that catalyzes the reduction of an acyl-CoA molecule to a primary alcohol.

"Fatty acyl-CoA reductase" is an enzyme that catalyzes the reduction of an acyl-CoA molecule to an aldehyde.

"Fatty aldehyde decarbonylase" is an enzyme that catalyzes the conversion of a fatty aldehyde to an alkane.

"Fatty aldehyde reductase" is an enzyme that catalyzes the reduction of an aldehyde to a primary alcohol.

"Fixed carbon source" is a molecule(s) containing carbon, typically an organic molecule, that is present at ambient temperature and pressure in solid or liquid form in a culture media that may be utilized by a microorganism cultured therein.

"Functional protein" refers to a protein whose its activity has been retained even though it may be attenuated.

"Genetically engineered", "genetically engineer", and "genetic engineering" refers to alteration of the DNA and/or RNA of a living cell by human intervention. Typically, the alteration is mediated by the introduction of one or more expression vectors, but in some instances, functionally equivalent alterations may be achieved by mutagenesis alone.

"Glycerolipid" refers to a glycerol molecule esterified at the sn-1, sn-2 or sn-3 position of the glycerol with one or more phosphate, fatty acid, phosphoserine, phosphocholine, phosphoinositol, or phosphoethanolamine, or other moieties covalently attached to the glycerol backbone. Examples of glycerolipids include triacylglycerides (triglycerides), diacylglycerides (diglycerides), monoacylglycerides (monoglycerides), glycerol-3-phosphate, lysophosphatidic acid, phosphatidic acid, phosphatidylcholine, phosphatidylserine, phosphatidylglycerol, and phosphatidylethanolamine.

"Glycerolipid synthesis enzyme" refers to an enzyme involved in the synthesis of glycerolipids. Glycerolipid synthesis enzymes function, for example, to covalently attach acyl groups to a substituted glycerol. Examples of glycerolipid synthesis enzymes include glycerol-3-phosphate acyltransferase, lysophosphatidic acid acyltransferase, diacylglycerol acyltransferase, phospholipid diacylglycerol acyltransferase, and phosphatidic acid phosphatase.

"Glycerophospholipid" is a glycerolipid that at the sn-1, sn-2 or sn-3 positions of the glycerol backbone has at least one or more covalently bound phosphate or a covalently bound phosphate containing moiety, for example, phosphocholine, phosphoserine, phosphoinositol, and phosphoethanolamine. Glycerophospholipids include phosphoglycerol, lysophosphatidic acid, phosphatidic acid, phosphatidylcholine, phosphatidylserine, phosphatidylglycerol, and phosphatidylethanolamine.

"Heterotrophic" as it pertains to culture conditions is culturing in the substantial absence of light while utilizing or metabolizing a fixed carbon source.

"Homogenate" is biomass that has been physically disrupted.

"Hydrogen:carbon ratio" is the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

"Hydrophobic fraction" is the portion, or fraction, of a material that is more soluble in a hydrophobic phase in comparison to an aqueous phase. A hydrophobic fraction is substantially insoluble in water and usually non-polar.

"Increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

"Inducible promoter" is a promoter that mediates transcription of an operably linked gene in response to a particular stimulus. Examples of such promoters may be promoter sequences that are induced in conditions of changing pH or nitrogen levels.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"In situ" means "in place" or "in its original position".

"Limiting concentration of a nutrient" is a concentration of a compound in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

"Lipase" is a water-soluble enzyme that catalyzes the hydrolysis of ester bonds in water-insoluble, lipid substrates. Lipases catalyze the hydrolysis of lipids into glycerols and fatty acids.

"Lipids" are a class of molecules that are soluble in nonpolar solvents (such as ether and chloroform) and are relatively or completely insoluble in water. Lipid molecules have these properties, because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). As used herein, the term "triacylglycerides" and "triglycerides" are interchangeable. "Fats" and "oils" are a subgroup of lipids called "triacylglycerides." "Oil," as distinguished from "fat" refers to triacylglycerides that are generally liquid at ordinary room temperature and pressure. Fatty acids are conventionally named by the notation that recites number of carbon atoms and the number of double bonds separated by a colon. For example oleic acid can be referred to as C18:1 and capric acid can be referred to as C10:0.

"Lipid biosynthesis pathway" or "lipid biosynthetic pathway" or "lipid metabolic pathway" or "lipid pathway" refers to the synthesis or degradation of lipids. Thus enzymes of the lipid biosynthesis pathway (e.g. lipid pathway enzyme) include fatty acid synthesis enzymes, fatty acid modification enzymes, and glycerolipid synthesis enzymes, as well as proteins (e.g. lipid pathway protein) that affect lipid metabolism, i.e., either lipid modification or degradation, and any proteins that chemically modify lipids, as well as carrier proteins. Lipid biosynthesis proteins also include transcription factors and kinases that are involved in lipid metabolism.

"Lipid biosynthesis gene" is any gene that encodes a protein that is involved in lipid metabolism, either in lipid synthesis, modification, or degradation, and any protein that chemically modifies lipids including carrier proteins.

"Lipid pathway enzyme" is any enzyme that plays a role in lipid metabolism, i.e., either lipid synthesis, modification, or degradation, and any proteins that chemically modify lipids, as well as carrier proteins.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Microalgae" is a eukaryotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella*, *Dunaliella*, and *Prototheca*. Microalgae also include other microbial photosynthetic organisms that exhibit cell-cell adhesion, such as *Agmenellum*, *Anabaena*, and *Pyrobotrys*. Microalgae also include obligate heterotrophic microorganisms that have lost the ability to perform photosynthesis, such as certain dinoflagellate algae species and species of the genus *Prototheca*.

"Microorganism" and "microbe" are microscopic unicellular organisms.

"Naturally co-expressed" with reference to two proteins or genes means that the proteins or their genes are co-expressed naturally in a tissue or organism from which they are derived, e.g., because the genes encoding the two proteins are under the control of a common regulatory sequence or because they are expressed in response to the same stimulus.

"Overexpression of a Gene" refers to (i) genetically engineering a gene so that it has, relative to a wild-type gene, different control sequences that result in increased amounts of a gene product (RNA and, if the RNA is an mRNA, the protein encoded by the mRNA) in a cell; (ii) genetically engineering a cell so that it has, relative to a wild-type cell, more copies of a gene and increased amounts of the corresponding gene product; and/or (iii) genetically engineering the coding sequence of a gene to either increase the stability and/or activity of the gene product (i.e., if the increase the stability of an RNA gene product, increase translation of an mRNA gene product, and/or increase the level of enzymatic activity of a protein encoded by the mRNA gene product, i.e., by making the protein more stable or more active (which may also be referred to as "Overexpression of an Enzymatic Product"). An "Overexpressed Gene" is the product of overexpression of a gene by any of the foregoing methods. Overexpression of a gene thus results in "Increased Expression of a Gene".

"Promoter" is a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which may be located as much as several thousand base pairs from the start site of transcription.

"*Prototheca* cell" refers to any cell, strain, and species of microalgae of the genus *Prototheca*. Illustrative *Prototheca* cells and strains include, without limitation, those of any of the following species: *Prototheca wickerhamii*, *Prototheca stagnora*, *Prototheca portoricensis*, *Prototheca moriformis*, and *Prototheca zopfii*. In one important embodiment, a *Prototheca* cell is a cell or strain of *Prototheca moriformis*. More generally, microalgal cells, strains, and species that share greater than 75% sequence identity with the 23s rRNA of *Prototheca moriformis* or that listed in SEQ ID NO: 5.

"Recombinant" is a cell, nucleic acid, protein or vector that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid originally formed in vitro, in general, by the manipulation of nucleic acid, e.g., using polymerases and endonucleases, or otherwise is in a form not normally found in nature, including an isolated form, i.e., wherein the nucleic acid is separated from at least one other component with which the native form of the nucleic acid naturally occurs. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The term "replacement" or "replace" or "replaced" when used in reference to modification of a gene sequence by another refers to the ablation or knockout of an endogenous gene by homologous recombination with an exogenous gene sequence containing suitable flanking regions.

"Inhibitory RNA" refers to RNA that inhibits gene expression. Inhibitory RNA includes double-stranded interfering RNA Inhibitory RNA includes long RNA hairpins, which, in some embodiments, are ~200 to 750 nucleotides in length, and comprise a coding sequence of the target gene of 50 to 650 nucleotides and its complementary sequence separated by sequence long enough (typically 25 to 200 nucleotides) to allow the coding sequence and its complementary to form a double-stranded sequence. RNAi also includes microRNAs, which are shorter than long RNA hairpins comprising typically only 19-22 nucleotides of the coding sequence of the target gene and its complement together with flanking sequences to engage the enzymes in the cell that mediate interference with gene expression by RNAi.

"Sonication" is a process of disrupting biological materials, such as a cell, by use of sound wave energy.

"Sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

"Up-regulation of an exogenous gene" refers to (i) genetically engineering a gene so that it has, relative to a wild-type gene, different control sequences that result in increased amounts of a gene product (RNA and, if the RNA is an mRNA, the protein encoded by the mRNA) in a cell; (ii) genetically engineering a cell so that it has, relative to a wild-type cell, more copies of a gene and increased amounts of the corresponding gene product; and/or (iii) genetically engineering the coding sequence of a gene to either increase the stability and/or activity of the gene product (i.e., if the increase the stability of an RNA gene product, increase translation of an mRNA gene product, and/or increase the level of enzymatic activity of a protein encoded by the mRNA gene product, i.e., by making the protein more stable or more active (which may also be referred to as "Up-regulation of an Enzymatic Product"). An "Up-regulated Gene" is the product of increased expression of a gene by any of the foregoing methods. Up-regulation of a gene thus results in "Increased Expression of a Gene".

Section II. Microalgae Lipid Biosynthesis Pathway

In certain embodiments the present invention provides recombinant *Chlorella protothecoides* cells that have been modified to alter the properties and/or proportions of lipids or fatty acids produced. The lipid biosynthesis pathway can further, or alternatively, be modified to alter the properties and/or proportions of various lipid molecules produced through enzymatic processing of lipids and intermediates in the lipid biosynthesis pathway. In various embodiments, the recombinant *Chlorella protothecoides* cells of the invention have, relative to their untransformed counterparts, optimized lipid yield per unit volume and/or per unit time, carbon chain length (e.g., for renewable diesel production or for industrial chemicals applications requiring lipid feedstock), reduced number of double or triple bonds, optionally to zero, and increasing the hydrogen:carbon ratio of a particular species of lipid or of a population of distinct lipid. In other embodiments, the lipids have increased number of double bonds.

In particular embodiments, one or more key enzymes that control branch points of metabolism of fatty acids and glycerolipids have been up-regulated or down-regulated to improve lipid production. Up-regulation, or over-expression, of genes may be achieved, for example, by transforming cells with expression constructs in which a gene encoding the enzyme of interest is expressed, e.g., using a strong promoter and/or enhancer elements that increase transcription. Such constructs can include a selectable marker such that the transformants may be subjected to selection, which can result in amplification of the construct and an increase in the expression level of the encoded enzyme. Down-regulation, or attenuation, of genes may be achieved, for example, by transforming cells with expression cassettes that ablate, through homologous recombination, all or a portion of the chromosomally-encoded corresponding gene. Expression levels of lipid pathway enzymes can also optionally be reduced through the use of inhibitory RNA constructs. Optionally, endogenous lipid pathway genes may be modified to alter individually or in combination their enzymatic specificity, level of expression, or cellular localization. The expression cassettes used in up- or down-regulation can replicate by integration into chromosomal DNA of the host cell or as a freely replicating vector.

Genes and gene products of the *Chlorella protothecoides* lipid biosynthesis pathway are listed in Table 1 and detailed in the subsections below.

TABLE 1

*Chlorella protothecoides* Lipid Pathway Genes and Proteins

| Sequence description | SEQ ID NO |
| --- | --- |
| Homomeric Acetyl-CoA carboxylase | SEQ ID NO: 63, nucleotide, SEQ ID NO: 64 protein |
| Acetyl-CoA Carboxylase 2 | SEQ ID NO: 65, nucleotide, SEQ ID NO: 66 protein |
| ACC-BC-1; ACCase, subunit, Heteromeric acetyl-CoA carboxylase Biotin Carboxylase (BC) subunit | SEQ ID NO: 67, nucleotide, SEQ ID NO: 68 protein |
| Acetyl-CoA Carboxylase subunit, Heteromeric acetyl-CoA carboxylase BCCP subunit | SEQ ID NO: 61, nucleotide, SEQ ID NO: 62, protein |
| acetyl-CoA carboxylase alpha-CT subunit | SEQ ID NO: 69 nucleotide, SEQ ID NO: 70, protein |
| Plastidial Acyl-Carrier Protein | SEQ ID NO: 73, nucleotide, 74, protein |
| Mitochondrial Acyl-Carrier Protein (ACP) | SEQ ID NO: 71 nucleotide, SEQ ID NO: 72 protein |
| Malonyl-CoA: ACP transacylase (MAT) | SEQ ID NO: 75, nucleotide, SEQ ID NO: 76, protein |
| Ketoacyl-ACP synthase I (KASI) | SEQ ID NO: 49126, nucleotide SEQ ID NO: 49127, protein |
| Ketoacyl-ACP synthase II (KASII) | SEQ ID NO: 77, nucleotide, SEQ ID NO: 78, protein |
| Ketoacyl-ACP reductase (KAR) | SEQ ID NO: 79, nucleotide, SEQ ID NO: 80, protein |
| 3-hydroxyacyl-ACP dehydrase (HD) | SEQ ID NO: 81, nucleotide, SEQ ID NO: 82, protein |
| Enoyl-ACP reductase (ENR) | SEQ ID NO: 83, nucleotide, SEQ ID NO: 84, protein |
| Stearoyl-ACP desaturase (SAD) | SEQ ID NO: 85, nucleotide, SEQ ID NO: 86, protein |
| Glycerol-3-phosphate acyltransferase (GPAT) | SEQ ID NO: 87, nucleotide, SEQ ID NO: 38, protein |
| 1-Acyl-sn-glycerol-3-phosphate acyltransferase (LPAAT) | SEQ ID NO: 89, nucleotide, SEQ ID NO: 90, protein |
| Diacylglycerol acyltransferase 2 (DGAT2) | SEQ ID NO: 91, nucleotide, SEQ ID NO: 92, protein |
| Diacylglycerol acyltransferase (DGAT) | SEQ ID NO: 93, nucleotide, SEQ ID NO: 94, protein |

TABLE 1-continued

Chlorella protothecoides Lipid Pathway Genes and Proteins

| Sequence description | SEQ ID NO |
|---|---|
| Fatty-acyl-ACP Thioesterase (FATA) | SEQ ID NO: 49128, nucleotide SEQ ID NO: 49129, protein |
| Fatty Acid (Oleate) Desaturase (FAD2) | SEQ ID NO: 95, nucleotide, SEQ ID NO: 96, protein |
| Pyruvate dehydrogenase | SEQ ID NO: 49130, 49131, 49132, nucleotide SEQ ID NO: 49133, 49134 protein |
| Acetate kinase | SEQ ID NO: 49135, nucleotide SEQ ID NO: 49136, protein |
| Phosphate acetyltransferase | SEQ ID NO: 49137, nucleotide SEQ ID NO: 49138, protein |
| Ketoacyl-ACP synthase III | SEQ ID NO: 49139, nucleotide SEQ ID NO: 49140, protein |
| Ketoacyl-ACP reductase (KAR) | SEQ ID NO: 49141, nucleotide SEQ ID NO: 49142, protein |
| Ketoacyl-CoA reductase (KCR) | SEQ ID NO: 49143, nucleotide SEQ ID NO: 49144, protein |
| Enoyl-CoA Reductase (ECR) | SEQ ID NO: 49145, nucleotide, SEQ ID NO: 49146, protein |
| Long-chain Acyl-CoA Synthetase (LACS) | SEQ ID NO: 49147, nucleotide SEQ ID NO: 49148, protein |
| Diacylglycerol Kinase (DGK) | SEQ ID NO: 49149, nucleotide SEQ ID NO: 49150, protein |
| Choline Kinase | SEQ ID NO: 49151, nucleotide SEQ ID NO: 49152, protein |
| Lipoate Synthase (LS) | SEQ ID NO: 49153, nucleotide SEQ ID NO: 49154, protein |
| Leafy cotyledon2 (LEC2) | SEQ ID NO: 49155, nucleotide SEQ ID NO: 49156, protein |
| Malic Enzyme | SEQ ID NO: 49157, nucl SEQ ID NO: 49158, protein |
| Acyl-CoA Binding protein (ACBP) | SEQ ID NO: 49159, nucl SEQ ID NO: 49160, protein |
| Phosphatidate cytidylyltransferase | SEQ ID NO: 49161, nucl SEQ ID NO: 49162, protein |
| Enoyl-CoA hydratase | SEQ ID NO: 49163, nucl SEQ ID NO: 49164, protein |
| Acyl-CoA oxidase | SEQ ID NO: 49165, nucl SEQ ID NO: 49166, protein |
| FAD3 Desaturase (Linoleate) | SEQ ID NO: 49167, nucl SEQ ID NO: 49168, protein |
| Glyoxysomal fatty acid beta-oxidation multifunctional protein | SEQ ID NO: 49169, nucl SEQ ID NO: 49170, protein |
| Monoglyceride lipase (MGL) | SEQ ID NO: 49171, nucl SEQ ID NO: 49172, protein |
| Triacylglycerol lipase 1 and 2 (TGL1, TGL2) | SEQ ID NO: 49173, 49174, nucleotide SEQ ID NO: 49175, 49176, protein |
| Lipid droplet protein 1, LDP1 | SEQ ID NO: 49177, nucleotide SEQ ID NO: 49178, protein |
| Nitrogen Response Regulator (NRR) | SEQ ID NO: 49179, nucleotide SEQ ID NO: 49180 protein |
| Monoacylglycerol Acyltransferase (MGAT1) | SEQ ID NO: 49181, nucleotide SEQ ID NO: 49182, protein |
| PDAT/LCAT/PDCT | SEQ ID NO: 49183, nucleotide SEQ ID NO: 49184, protein |
| Citrate Synthase | SEQ ID NO: 49185, nucleotide |

TABLE 1-continued

Chlorella protothecoides Lipid Pathway Genes and Proteins

| Sequence description | SEQ ID NO |
|---|---|
| Cellulase/Endoglucanase (EG1)/ Expansin | SEQ ID NO: 49186, protein SEQ ID NO: 49187, nucleotide |
| Rab/RAN GTPase | SEQ ID NO: 49188, protein SEQ ID NO: 49189, nucleotide SEQ ID NO: 49190, protein |
| ACP-P Promoter | SEQ ID NO: 49191, nucleotide |

A. Acetyl-CoA—Malonyl-CoA to Acyl-ACP

The early stages of fatty acid synthesis involve the conversion of a fixed carbon (e.g., glucose, sucrose, etc.) or other carbon sources into pyruvate. Next, the pyruvate dehydrogenase complex (PDH), comprising pyruvate dehydrogenase, dihydrolipoyl transacetylase, and dihydrolipoyl dehydrogenase, converts the three carbon metabolite pyruvate into the two carbon metabolite acetyl-CoA. The acetyl-CoA carboxylase (ACC) complex, utilizing bicarbonate as a substrate, generates the 3-carbon compound malonyl-CoA. Malonyl-CoA:ACP acyltransferase (MAT) then catalyzes the transfer of a malonyl group from malonyl-CoA to the acyl carrier protein (ACP), thereby generating malonyl-ACP. ACP is used as the acyl carrier for the various intermediate reactions in fatty acid biosynthesis. The metabolites acetyl-CoA and malonyl-CoA and the ACP protein are thus important starting points for fatty acid biosynthesis.

To genetically engineer a microbe for increased production of fatty acids and lipids, recombinant modifications may be made, either individually or in combination to obtain increased acetyl-CoA/malonyl-CoA/ACP production. For example, to increase malonyl-CoA production, an expression cassette may be generated and used to transform a microbe to overexpress polynucleotides encoding one or more components of the ACC enzyme complex under the control of a constitutive or regulated promoter. Additional examples of enzymes suitable for up-regulation according to embodiments of the invention include enzymes of the pyruvate dehydrogenase complex (examples, some from microalgae, include GenBank Accession Numbers NP_415392; AAA53047; Q1XDM1; and CAF05587). Up-regulation of pyruvate dehydrogenase can increase production of acetyl-CoA, and thereby increase fatty acid synthesis.

The acetyl-CoA carboxylase complex catalyzes the initial step in fatty acid synthesis. Accordingly, one or more enzymes comprising this complex may be up-regulated to increase production of fatty acids (examples, some from microalgae, include GenBank accession numbers BAA94752; AAA75528; AAA81471; YP_537052; YP_536879; NP_045833; and BAA57908). Enzymes of the ACCase complex may include the heteromeric ACCase BC subunit 1, the heteromeric ACCase BCC subunit, the heteromeric ACCase a-CT subunit, and the heteromeric ACCase b-CT subunit 1.

Enzymes that deplete pools of pyruvate or acetyl-CoA for the synthesis of metabolites other than fatty acids may compete with lipid biosynthesis pathway enzymes for precursor metabolites. Attenuation of these competitor enzymes may increase the production of fatty acids or lipids. To genetically engineer a microbe for increased production of fatty acids and lipids, recombinant modifications can be made, either individually or in combination to attenuate enzymes that compete for metabolite precursors. For example, to decrease the use of acetyl-CoA for acetate production, an expression cassette can be generated to ablate the gene or genes encoding acetate kinase enzymes. Attenuation of acetate kinase can also be achieved through the construction and use of expression cassettes comprising an antisense RNA under the control of a constitutive or regulated promoter. Additional examples of enzymes suitable for down-regulation according to the methods of the invention include lactate dehydrogenase, which synthesizes lactate from pyruvate or phosphate acetyltransferase (PTA), which catalyzes the conversion of acetyl-CoA to acetylphosphate, a step in the metabolism of acetate.

B. Acyl-ACP to Fatty Acid

The growing acyl-ACP chain is elongated in 2-carbon increments through a set of four enzymatic reactions involving condensation, a first reduction reaction, dehydration, and a second reduction reaction. These reactions are catalyzed by a condensing enzyme (0-ketoacyl-ACP synthase, KAS), a first reductase enzyme (β-ketoacyl-ACP reductase, KAR), a dehydrase (β-hydroxyacyl-ACP dehydrase, HR) and a second reductase (enoyl-ACP reductase, ENR). Up-regulation of KASI can be used to enhance fatty acid biosynthesis, and hence lipid production. Replacement of KASI by heterologous KAS genes with varying specificities can also be used to alter oil profile.

The initial condensation reaction between malonyl-ACP and acetyl-CoA to produce a 4-carbon compound is catalyzed by β-ketoacyl-ACP synthase (KAS) III. Successive 2-carbon additions to the elongating acyl-ACP chain, through C16:0, are catalyzed by KAS I. The enzyme KASII performs a 2-carbon extension of C16:0-ACP to C18:0-ACP. Depending on the desired length of fatty acid to be produced, one or more genes encoding KAS enzymes can be attenuated or over-expressed in the microbe.

Fatty acyl-ACP thioesterase (TE) enzymes terminate elongation by hydrolyzing the acyl-ACP into free fatty acids and ACP. TEs may show specificity for acyl-ACPs of certain carbon lengths and degree of saturation or may be broad TEs, able to cleave acyl-ACP chains of varying length and level of saturation. The substrate specificity of TEs is an important contributor to establishing the chain length and degree of saturation of fatty acids. Depending on the desired length or degree of saturation of the fatty acid to be produced, one or more genes encoding acyl-ACP thioesterases can be attenuated or over-expressed in the microbe. For example, an endogenous fatty acyl-ACP thioesterase gene showing preference for C18-ACP (FATA may be knocked out or reduced in expression while concomitantly a different TE, showing specificity for saturated C12 and C14-ACPs is overexpressed in the microbe, thereby altering the population of fatty acids in the microbe).

C. Unsaturated Fatty Acids and Fatty Acyl Chains

The introduction of carbon-carbon double bonds into a fatty acid, fatty acyl-CoA, or fatty acyl-ACP chains relies on the activity of desaturases. Desaturase enzymes may show specificity for the carbon chain length and degree of saturation of their substrates. Specific desaturases can convert saturated fatty acids or saturated fatty acyl-ACPs to unsaturated fatty acids or unsaturated fatty acyl-ACPs. Other desaturases enzymes may increase the number of carbon-carbon double bonds of unsaturated fatty acids.

Stearoyl-ACP desaturase (see, e.g., GenBank Accession numbers AAF15308; ABM45911; AAY86086, for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. For illustrative purposes, SADs are responsible for the synthesis of C18:1 fatty acids from C18:0 precursors.

Additional desaturases are the fatty acyl desaturases (FADs), including the phosphatidylglycerol desaturase (FAD4), the plastidial oleate desaturase (FADE), the plastidial linoleate desaturase (FAD7/FAD8), endoplasmic reticulum oleate desaturase (FAD2), the endoplasmic reticulum linolate desaturase (FAD3), the delta 12 fatty acid desaturase (Δ12 FAD) and the delta 15 fatty acid desaturase (Δ15 FAD). These desaturases also provide modifications with respect to lipid saturation. For illustrative purposes, Δ12 fatty acid desaturases are responsible for the synthesis of C18:2 fatty acids from C18:1 precursors and Δ15 fatty acid desaturases are responsible for the synthesis of C18:3 fatty acids from C18:2 precursors.

Still additional desaturases, including the palmitate-specific monogalactosyldiacylglycerol desaturase (FADS), the linoleoyl desaturase, ω-6 fatty acid desaturases, ω-3 fatty acid desaturases, and ω-6-oleate desaturases, provide modifications with respect to lipid saturation. The expression of one or more desaturases, such as ω-6 fatty acid desaturase, ω-3 fatty acid desaturase, or ω-6-oleate desaturase, can be controlled to alter the ratio of unsaturated to saturated fatty acids.

Acyl-ACPs synthesized in the plastid are either used directly within that organelle to form lipids, including glycerolipids, or exported outside the plastid for synthesis of lipids including phospholipids, triacygylcerol, or waxes. Lipid biosynthesis genes may show specificity for activity in specific subcellular locations.

D. Fatty acid to Fatty Acyl-CoA

Fatty acids are activated to Acyl-CoAs by Long-Chain Fatty acid CoA synthetases, (LACS) also known as long-chain fatty acids CoA ligases. LACS is involved in the channeling of fatty acids to various metabolic pathways, including breakdown of fatty acids. It is also involved in the uptake of exogenous fatty acids. In particular, LACS are involved in re-cycling of medium chain fatty acids in transgenic strains expressing heterologous medium-chain thioesterases. Thus, it is particularly useful to attenuate or knock out LACS expression in the transgenic strain to reduce futile cycling of medium-chain fatty acids. This approach provides higher productivity and yield combined with increased medium chain fatty acids in a transgenic strain expressing a medium-chain thioesterase.

E. Lipid Biosynthesis

Triacylglycerides may be formed through three sequential acyl-CoA-dependent acylations of a sn-glycerol-3-phosphate molecule. The first acylation, the rate-limiting step of glycerolipid synthesis, is catalyzed by glycerol-3-phosphate acyltransferase (GPAT) to produce lyso-phosphatidic acid. The second acylation step is catalyzed by the enzyme acyl-CoA:lyso-phosphatidic acid acyltransferase (LPAAT). Prior to the third acylation step, the enzyme phosphatidic acid phosphatase (PAP) (or lipins) carries out the removal of the phosphate group from phosphatidic acid to generate sn-1,2-diacylglycerol (DAG). The final acyl-CoA-dependent acylation is catalyzed by acyl-CoA: diacylglycerol acyltransferase (DGAT).

Microbes may be genetically engineered for increased production of lipids. For example, to increase the production of TAGs, an expression cassette may be generated and used to transform a microbe to polynucleotides operable to increase the expression of GPAT. This expression cassette may comprise a constitutive or inducible promoter active to drive expression of GPAT and may be utilized in the genetic background of a strain in which endogenous GPAT activity has been attenuated.

Microbes may be genetically engineered for increased production of triacylglycerol molecules with desired properties. Certain acyltransferase enzymes, including GPATs, LPAATs, and DGATs may demonstrate specificity for a subcellular localization or substrate specificity for the length and degree of saturation of the acyl-CoA chain they transfer to the substituted glycerol backbone. Additionally, LPAAT and DGAT enzymes may show substrate specificity for the form of substituted glycerol to which they transfer an acyl-CoA. Depending on the desired properties of the triacylglyceridesto be produced, one or more genes encoding GPATs, LPAATs, DGATs, or other acyltranferases may be attenuated or over-expressed in the microbe. For example, to increase the production of TAGs with midchain fatty acids esterified at the sn-2 position, an expression cassette may be generated and used to transform a microbe to overexpress an LPAAT having specificity for transferring midchains. This expression cassette may comprise a constitutive or inducible promoter active to drive expression of LPAAT and may be utilized in the genetic background of a strain in which endogenous LPAAT activity has been attenuated.

In a similar fashion, to increase production of TAGs, an expression cassette may be generated and used to transform a microbe to overexpress polynucleotides encoding a DGAT, active to transfer a acyl-CoA to a DAG molecule. This expression cassette may comprise a constitutive or inducible promoter active to drive expression of DGAT2. According to the desired characteristics of the fatty acids or lipids to be produced by the recombinant microbe, it may be advantageous to couple up-regulation of a TE characterized by substrate specificity with one or more GPAT, LPAAT, or DGAT enzymes showing the same substrate specificity.

The Monoacylglycerol Acyltransferase (MGAT) gene, catalyzed the synthesis of diacyglycerol, and can generally also catalyze the final step in triacylglycerol biosynthesis. Hence, upregulation of the MGAT gene provided in this invention may be desirable.

Alternate lipid pathway enzymes can generate triacylglyceride molecules through a route separate from that above. Enzymes of the fatty acyl-CoA-independent triacylglycerol pathway transfer fatty acyl groups between phosphatidylcholine (PC) moieties employing acyl-lysophosphatidylcholine acyl transferases that may exhibit selective substrate specificity, ultimately transferring them to diacylglycerol.

The PDAT (Phospholipid:Diacylglycerol Acyltransferase) gene represents an important alternative pathway for lipid biosynthesis. This enzyme is involved in membrane lipid turnover and can catalyze the production of TAG via 1) transacylation of DAG by acyl groups from phospholipids and galactolipids, and 2) DAG:DAG transacylation. It may also contain broad specificity, including PDCT activity (PhosphatidylCholine:Diacylglycerol Acyltransferase), meaning that this enzyme plays a key role in recycling of membrane components into TAG. The PDAT in algae is often unrecognizable when searching by homology using a PDAT from plants, and instead LCAT (Lecithin:Cholesterol Acyltransferase) genes may have PDAT activity in algae. We provide here a PDAT/PDCT/LCAT enzyme from *Auxenochlorella protothecoides* that is useful for overexpression to enhance lipid biosynthesis. Furthermore, expression of this gene will enhance conversion of membrane components to TAG during the lipid production phase, a highly desirable goal. Finally, this enzyme may be modified, altered in expression, or replaced with a heterologous PDAT to alter final TAG profiles and regiospecficity, by first providing additional genes to alter membrane components (chaing length, desaturation levels) that will then find their way in to TAG molecules.

F. Additional Lipid Molecules

In addition to their incorporation into DAGs and TAGs, fatty acids or fatty acyl molecules may be incorporated into a range of lipid molecules including but not limited to phospholipids, phosphatidylcholine (PC), phosphatidylserine (PS), phosphatidylinositol (PI), sphingolipids (SL), monogalactosyldiacylglycerol, digalactosyldiacylglycerol, and wax esters. Enzymes that synthesize molecules of PC, PS, PI, SL, wax esters, or the galactolipids monogalactosyldiacylglycerol (MGDG) or digalactosyldiacylglycerol (DGDG) may compete with enzymes that lead to or ultimately synthesize DAGs and TAGs for substrates including fatty acids or fatty acyl molecules. Genes encoding proteins involved in the synthesis, utilization, or degradation of PC, PS, PI, SL, monogalactosyldiacylglycerol, digalactosyldiacylglycerol, or wax esters may include diacylglycerol cholinephosphotransferase (DAG-CPT), cytidine diphosphate diacylglycerol synthase (CTP-DAG synthase), phosphatidylinositol synthase (PI synthase), choline kinase (CK), phosphatidylinositol-3-kinase (PI3-Kinase), phosphatidylinositol-4-kinase (PI4-Kinase), diacyerolglycerol kinase (DGK), phosphatidylglycerol-3-phosphate phosphatase (PGPP), cholinephosphate cytidylyltransferase (CPCT), phosphatidylserine decarboxylase (PSD), phospholipase C (PliC), phospholipase D (PliD), sphingolipid desaturase (SD), monogalactosyldiacylglycerol synthase (MGDG synthase), digalactosyldiacylglycerol synthase (DGDG synthase), ketoacyl-CoA synthase (KCS), 3-ketoacyl reductase (KR), and wax synthase (WS). Depending on the desired properties of the lipid molecule to be produced, one or more genes encoding enzymes that utilize fatty acids or fatty acyl molecules as substrates to produce lipid molecules may be attenuated or over-expressed in the microbe, for example using RNAi, hairpin constructs, or double or single knockouts.

In one embodiment, provided are sequences, compositions, and methods for inhibition of Diacylglycerol Kinase (DGK), which converts DAG to PA. For example, DGK can be inhibited through use of RNAi, hairpin constructs, or double or single knockouts. DGK provides a key regulatory point for the flow of lipid precursors into either synthesis of Phosphatidic Acid (PA) to form phospholipids, or to triacylglycerol biosynthesis. Thus, manipulation of the timing and expression level of DGK is highly desirable. In particular, a preferred promoter such as, but not limited to, the ACP-P promoter, driving and RNAi construct for DGK, is used to allow for efficient expression of DGK during growth phase, followed by attenuation during the lipid production. This shifts the cell from phospholipid production, during the growth phase, to higher levels of TAG production during the lipid production phase. Depending on the nature of the DGK subunit, it may also be desirable in some cases to overexpress a DGK. For example, DGK epsilon subunit stimulated lipogenesis. In other embodiments, provided are sequences, compositions, and methods for overexpression of DGK epsilon subtype (DGKe). In some aspects, overexpression of DGKe results in selective removal of DAGs with certain acyl groups such as C20:4.

To engineer a microbe for the increased production of triglycerides, it may be advantageous to attenuate enzymes that support phospholipid synthesis. For example, to decrease production of the phospholipid cytidine diphosphate (CDP)-diacylglycerol, an expression cassette may be generated and used to transform a microbe to attenuate phosphatidate cytidylyltransferase, which catalyzes condensation of phosphatidic acid and cytidine triphosphate to produce to CDP-diacylglycerol.

Further, additional lipid moieties other than triacylglycerides may utilize derivations of phosphorylated glycerol as a backbone. Enzymes such as phosphatidylglycerophosphate synthase (PGP Synthase), involved in the synthesis of phopholipids may compete with enzymes that provide for triacylglycerols for substrates including phosphorylated forms of glycerol. Depending on the desired properties of the lipid molecule to be produced, one or more genes encoding phosphatidylglycerophosphate synthase may be attenuated or over-expressed in the microbe. Lipoate Synthase (LS), also called Lipoyl Synthase or Lipoic Acid Synthase, is generally localized to the mitochondria and utilized in the synthesis of lipoic acid. Lipoic acid is an important co-factor and antioxidant.

G. Fatty Acid Degradation

To genetically engineer a microbe for increased production of specific fatty acids and lipids, recombinant modifications may be made, either individually or in combination, to decrease the degradation of fatty acids and lipids. As proteins such as acyl-CoA oxidase, 3-ketoacyl-CoA thiolase, acyl-CoA dehydrogenase, glyoxysomal fatty acid beta-oxidation multifunctional protein, and enoyl-CoA hydratase are involved in the degradation of fatty acids, these and other proteins may be attenuated in the microbe to slow or prevent fatty acid degradation. For example, to engineer a microbe to decrease fatty acid degradation, an expression cassette may be generated and used to transform a microbe to down-regulate one or more of acyl-CoA oxidase, enoyl-CoA hydratase, and glyoxysomal fatty acid beta-oxidation multifunctional protein, either through a knockout or knockdown approach. According to the desired chain length and degree of saturation of the fatty acids to be produced by the recombinant microbe, it may be advantageous to down-regulate fatty acid or lipid degradation enzymes in the genetic background of a microbe that has been engineered to alter additional lipid pathway genes or gene products.

Long-chain acyl-CoA synthetases (also known in the art as long-chain acyl-CoA ligases) convert free fatty acids into acyl-CoA thioesters. These acyl-CoA thioesters may then be degraded by enzymes involved in fatty β-oxidation. To engineer a microbe for decreased fatty acid degradation, an expression cassette may be generated and used to transform a microbe to down-regulate long-chain acyl-CoA synthetase, either through a knockout or knockdown approach.

H. Monoglyceride, Triglyceride, and Lipid Degradation

A strategy to increase the recombinant microbial production of triglycerides is to prevent or reduce the enzymatic degradation of these molecules. Enzymes such as monoglyceride lipase and triacylglycerol lipase that hydrolyze triglycerides to fatty acids and glycerol are examples of proteins that may be attenuated in a microbe to slow or prevent degradation of triglycerides. For example, to engineer a microbe to decrease triglyceride degradation an expression cassette may be generated and used to transform a microbe to down-regulate monoglyceride lipase or triacylglycerol lipase, either through a knockout or knockdown approach. According to embodiments of the present invention, it may be advantageous to attenuate one or more lipases under specific culture conditions, for example during lipid production.

I. Global Regulators

Furthermore, up- and/or down-regulation of genes may be applied to global regulators controlling the expression of the genes of the lipid biosynthetic pathway. Accordingly, one or more global regulators of lipid synthesis may be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see GenBank accession numbers NP_035610 and Q9WTN3). In one embodiment, a global regulator such as the endogenous LEC2 homolog (Leafy Cotyledon 2 homolog), a B3 DNA-binding domain protein, may be upregulated to increase lipid production. Decoupling or alteration of nitrogen sensing from the process of lipid biosynthesis may also be of value (Boyle et al, J. Biol. Chem., May 4, 2012). Also presented in this invention is a Nitrogen Response Regulator, NRR1, a Squamosa Binding protein. In some instance it may be desirable, for example, to increase the response to nitrogen starvation by enhancing expression of NRR1.

J. Lipid Droplet Proteins

Eukaryotic cells store triacylglycerol molecules in distinct organelles, often called lipid droplets. Proteins associated with lipid droplet proteins, such as lipid droplet protein 1 (LDP1, are crucial to lipid droplet structure, formation, size, and number. In some instances, attenuation of lipid droplet proteins results in increases in lipid droplet size. In other instances, overexpression of mutated sequences of lipid droplet proteins results in increased lipid droplet size and number. To genetically engineer a microbe for the production of fatty acids and lipids, recombinant modifications can be made, either individually or in combination to alter the expression of lipid droplet proteins. For example, an expression cassette can be generated to attenuate or ablate the gene or genes lipid droplet proteins. Attenuation through the use of RNAi may be coupled to an inducible or constitutive promoter. In an additional embodiment, an expression cassette can be generated to overexpress one or more lipid droplet proteins. Overexpression of lipid droplet proteins may be driven by constitutive or inducible promoters.

K. Altering Carbon Metabolism

Numerous enzymatic pathways are involved in metabolizing sugars and metabolites into intermediates suitable for use in fatty acid or lipid synthesis or for other cellular pathways. In one embodiment of the present invention, it is advantageous to alter the regulation or activity of enzymes that contribute to production of metabolites involved in lipid synthesis or that utilize the intermediates or metabolites of lipid synthesis for pathways other than the fatty acid and lipid pathways. The Kreb's cycle is such a metabolic pathway that consumes acetyl-CoA to ultimately produce carbon dioxide. Enzymatic participants of the Kreb's Cycle include fumarate hydratase (also known in the art as fumarase). To engineer a microbe for the increased production of specific fatty acids or lipids, an expression cassette may be generated and used to transform a microbe to attenuate fumarate hydratase, either through a knockout or knockdown approach. According to embodiments of the present invention, it may be advantageous to attenuate fumarate hydratase under specific culture conditions, for example during lipid production. This can be achieved with the use of tunable promoters disclosed herein, for instance the promoter for ACP will be up-regulated strongly during lipid production, and hence and RNAi construct bearing an RNAi for fumarate hydratase, under control of the ACP promoter, will activate less strongly during the growth phase and will be activated strongly during the lipid production phase.

An additional example of an enzyme involved in carbon metabolism is NAD-dependent glycerol-3-phosphate dehydrogenase that reversibly converts sn-glycerol 3-phosphate to dihydrohyxacetone phosphate, (also known in the art as glycerone phosphate). To increase the level of the triacylglycerol backbone precursor molecule, the sn-glycerol 3-phosphate metabolite, an expression cassette may be generated and used to transform a microbe to enhance expression of NAD-dependent glycerol-3-phosphate dehydrogenase. According to embodiments of the present invention, it may be advantageous to attenuate NAD-dependent glycerol-3-phosphate dehydrogenase under specific culture conditions, for example during lipid production. In some embodiments, it may be advantageous to combine the expression of several pathway enzymes for triacylglycerol production, for example the PAP, G3PDH, GPAT, LPPAT, and DGAT combination.

Other proteins, such as glycerophosphodiester phosphodiesterase, synthesize intermediates of the lipid pathway. Glycerophosphodiester phosphodiesterase hydrolyses a glycerophosphodiester to form sn-glycerol 3-phosphate, which may be used in lipid synthesis. To engineer a microbe for increased production of lipids, an expression cassette may be generated and used to transform a microbe to overexpress polynucleotides encoding glycerophosphodiester phosphodiesterase. Celluases, such as endoglucanase, are useful for breaking down cellulosic compounds into sugar utilizable by the cell. Provided is an endogenous endoglucanase that may potentially find uses in secretion to break down cellulosic material, or as a mechanism for loosening cell walls to allow for enhanced lipid droplet formation.

L. Other Genes

ACBPs (Acyl-CoA Binding Proteins) may also transport fatty acids to the nucleus where they may influence transcription and the activity of DNA polymerase and other enzymes. ACBPs influence the incorporation of fatty acids into triacylglycerol and have varying substrate affinities. The ACBP may be over-expressed, knocked out, or replaced with a heterologous ACBP with a different substrate preference, (e.g. Bovine ACBP).

In another embodiment, it is desirable to attenuate Citrate synthase. Citrate synthase competes with the pathway for lipid biosynthesis, competing with the ATP-Citrate Lyase, a critical enzyme in lipid production. Down-regulation of Citrate synthase reduces the competition for this pathway and enhances total lipid biosynthesis.

M. Cell Cycle & Cell Size

One method for enhancing lipid biosynthesis provided herein is to alter the cell cycle of the host cell so that it becomes arreseted during cell division. This produces cells that are larger and contain more lipid per cell. Since this also provides more lipid volume per unit surface area and requires reduced numbers of membrane components, proteins, nuclear components, organelles, and translational machinery, it provide increased productivity and yield. We provide here a small Rab/RAN GTPase involved in cell cycle. Overexpression of this gene using a suitable promoter is expected to lead to cell cycle arrest during lipid production and create larger cells.

Another method for increasing cell size is to overexpress Expansin. We present here an endoglucanase/expansin gene that is useful for 1) secreting from the cell to break down external cellulose feedstocks and 2) overexpressing to loosen the host cell wall and provide for expansion of the cell; larger cells can support a larger volume of lipid with a reduced surface area of membrane, providing enhanced productitivity and yield.

N. Fatty Acid Elongation

Fatty acid elongation proceeds from long-chain fatty acyl-CoAs, taking place in the endoplasmic reticulum. It is catalyzed by the Ketoacyl-CoA Synthases (KCS), Enoyl-CoA Reductase (ECR) and Ketoacyl-CoA Reductase (KCR). These genes are provided in Table 1. Manipulation of the fatty acid elongation pathway is highly desirable for the production of Very-Long Chain Fatty Acids (VLCFAs) such as Erucic Acid. The uses of Erucid acid include but are not limited to: oil paints, surfactatants, lubricants, appetite suppressants. In some preferred embodiments, heterologous KCS genes are introduced into the transgenic strain, and existing KCS genes may be replaced or attenuated, to produce high levels of VLCFAs such as Eruic acid. It may also be desirable knockout or attenuate the endogenous FAD gene(s), also provided in Table 1, to reduce competition with the elongation pathway.

Section III. Cultivation

In certain embodiments, the present invention generally relates to cultivation of microbes, e.g., oleaginous microbes, such as microalgae, including *Chlorella* and *Prototheca* species and strains, and yeast, fungi, and bacteria species and strains, for the production of microbial oil (lipids). In particular embodiments, the microbes are recombinant microbes.

1. *Chlorella protothecoides* Species and Strains

Species of *Chlorella protothecoides* can be identified by amplification of certain target regions of the genome. For example, identification of a specific *Chlorella protothecoides* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121, "Identification of *Chlorella* spp. isolates using ribosomal DNA sequences". Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Chlorella protothecoides*, but other hydrocarbon and lipid producing organisms with similar lipid profiles and production capability. For examples of methods of identification and classification of algae also see for example *Genetics*, 2005 August; 170(4):1601-10 and *RNA*, 2005 April; 11(4): 361-4.

Thus, genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae used in the present invention. Examples of such DNA sequence comparison for species within the *Chlorella protothecoides* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

In some embodiments the microalgae have genomic DNA sequences encoding for 23S rRNA that have at least 99%, least 95%, at least 90%, or at least 85% nucleotide identity to at least one of the sequences listed in SEQ ID NOs: 1-9 and 60.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=-4, and a comparison of both strands. For amino acid sequences, the BLASTP program uses as defaults a word length (W) of 3, an expectation (E) of 10, and the BLOSUM62 scoring matrix. The TBLASTN program (using protein sequence to find nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Other considerations affecting the selection of microorganisms for use in the invention include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light).

2. Bioreactor

Microorganisms are cultured both for purposes of conducting genetic manipulations and for production of hydrocarbons (e.g., lipids, fatty acids, aldehydes, alcohols, and alkanes). The former type of culture is conducted on a small scale and initially, at least, under conditions in which the starting microorganism can grow. Culture for purposes of hydrocarbon production is usually conducted on a large scale (e.g., 10,000 L, 40,000 L, 100,000 L or larger bioreactors) in a bioreactor. Microalgae, including *Chlorella protothecoides* species are typically cultured in the methods of the invention in liquid media within a bioreactor. Typically, the bioreactor does not allow light to enter.

The bioreactor or fermenter is used to culture microalgal cells through the various phases of their physiological cycle. Bioreactors offer many advantages for use in heterotrophic growth and propagation methods. To produce biomass for use in food, microalgae are preferably fermented in large quantities in liquid, such as in suspension cultures as an example. Bioreactors such as steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained for reproduction of microalgae until a desired increase in number of said microalgae has been achieved.

Bioreactor ports can be used to introduce, or extract, gases, solids, semisolids, and liquids, into the bioreactor chamber containing the microalgae. While many bioreactors have more than one port (for example, one for media entry, and another for sampling), it is not necessary that only one substance enter or leave a port. For example, a port can be used to flow culture media into the bioreactor and later used for sampling, gas entry, gas exit, or other purposes. Preferably, a sampling port can be used repeatedly without altering compromising the axenic nature of the culture. A sampling port can be configured with a valve or other device that allows the flow of sample to be stopped and started or to provide a means of continuous sampling. Bioreactors typically have at least one port that allows inoculation of a culture, and such a port can also be used for other purposes such as media or gas entry.

Bioreactors ports allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

3. Media

Microalgal culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)_2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at www.utex.org/, a site maintained by the University of Texas at Austin, 1 University Station A6700, Austin, Tex., 78712-0183, for its culture collection of algae (UTEX). For example, various fresh water and salt water media include those described in PCT Pub. No. WO 2008/151149, incorporated herein by reference.

In a particular example, Proteose Medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use. Another example is the *Chlorella protothecoides* isolation medium (PIM), which comprises 10 g/L postassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose 0.001 g/L thiamine hydrochloride, 20 g/L agar, 0.25 g/L 5-fluorocytosine, at a pH in the range of 5.0 to 5.2 (see Pore, 1973, App. Microbiology, 26: 648-649). Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic). Additionally, U.S. Pat. No. 5,900,370 describes media formulations and conditions suitable for heterotrophic fermentation of *Chlorella protothecoides* species.

For oil production, selection of a fixed carbon source is important, as the cost of the fixed carbon source must be sufficiently low to make oil production economical. Thus, while suitable carbon sources include, for example, acetate, floridoside, fructose, galactose, glucuronic acid, glucose, glycerol, lactose, mannose, N-acetylglucosamine, rhamnose, sucrose, and/or xylose, selection of feedstocks containing those compounds is an important aspect of the methods of the invention. Suitable feedstocks useful in accordance with the methods of the invention include, for example, black liquor, corn starch, depolymerized cellulosic material, milk whey, molasses, potato, sorghum, sucrose, sugar beet, sugar cane, rice, and wheat. Carbon sources can also be provided as a mixture, such as a mixture of sucrose and depolymerized sugar beet pulp. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Highly concentrated carbon sources as feedstock for fermentation are preferred. For example, in some embodiments glucose levels of at least 300 g/L, at least 400 g/L, at least 500 g/L, or at least 600 g/L or more of glucose level of the feedstock prior to the cultivation step, is added to a fed batch cultivation, in which the highly concentrated fixed carbon source is fed to the cells over time as the cells grow and accumulate lipid. In other embodiments, sucrose levels of at least 500 g/L, at least 600 g/L, at least 700 g/L, at least 800 g/L or more of sucrose prior to the cultivation is added to a fed batch cultivation, in which the highly concentrated fixed carbon source is fed to the cells over time as the cells grow and accumulate lipid. Non-limiting examples of highly concentrated fixed carbon source such as sucrose include thick cane juice, sugar cane juice, sugar beet juice and molasses. Carbon sources of particular interest for purposes of the present invention include cellulose (in a depolymerized form), glycerol, sucrose, and sorghum, each of which is discussed in more detail below.

In accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstocks have been found to be inhibitory to yeast growth, and yeast cannot use the 5-carbon sugars produced from cellulosic materials (e.g., xylose from hemi-cellulose). By contrast, microalgae can grow on processed cellulosic material. Cellulosic materials generally include about 40-60% cellulose; about 20-40% hemicellulose; and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Cellulosic materials are treated to increase the efficiency with which the microbe can utilize the sugar(s) contained within the materials. The invention provides novel methods for the treatment of cellulosic materials after acid explosion so that the materials are suitable for use in a heterotrophic culture of microbes (e.g., microalgae and oleaginous yeast). As discussed above, lignocellulosic biomass is comprised of various fractions, including cellulose, a crystalline polymer of beta 1,4 linked glucose (a six-carbon sugar), hemicellulose, a more loosely associated polymer predominantly comprised of xylose (a five-carbon sugar) and to a lesser extent mannose, galactose, arabinose, lignin, a complex aromatic polymer comprised of sinapyl alcohol and its derivatives, and pectins, which are linear chains of an alpha 1,4 μlnked polygalacturonic acid. Because of the polymeric structure of cellulose and hemicellulose, the sugars (e.g., monomeric glucose and xylose) in them are not in a form that can be efficiently used (metabolized) by many microbes. For such microbes, further processing of the cellulosic biomass to generate the monomeric sugars that make up the polymers can be very helpful to ensuring that the cellulosic materials are efficiently utilized as a feedstock (carbon source).

In another embodiment of the methods of the invention, the carbon source is glycerol, including acidulated and non-acidulated glycerol byproduct from biodiesel transesterification. In one embodiment, the carbon source includes glycerol and at least one other carbon source. In some cases, all of the glycerol and the at least one other fixed carbon source are provided to the microorganism at the beginning of the fermentation. In some cases, the glycerol and the at least one other fixed carbon source are provided to the microorganism simultaneously at a predetermined ratio. In some cases, the glycerol and the at least one other fixed carbon source are fed to the microbes at a predetermined rate over the course of fermentation.

Some microalgae undergo cell division faster in the presence of glycerol than in the presence of glucose (see PCT Pub. No. 2008/151149). In these instances, two-stage growth processes in which cells are first fed glycerol to rapidly increase cell density, and are then fed glucose to accumulate lipids can improve the efficiency with which lipids are produced. The use of the glycerol byproduct of the transesterification process provides significant economic advantages when put back into the production process. Other feeding methods are provided as well, such as mixtures of glycerol and glucose. Feeding such mixtures also captures the same economic benefits. In addition, the invention provides methods of feeding alternative sugars to microalgae such as sucrose in various combinations with glycerol.

In another embodiment of the methods of the invention, the carbon source is invert sugar. Invert sugar is produced by splitting the sucrose into its monosaccharide components, fructose and glucose. Production of invert sugar can be achieved through several methods that are known in the art. One such method is heating an aqueous solution of sucrose. Often, catalysts are employed in order to accelerate the conversion of sucrose into invert sugar. These catalysts can be biological, for example enzymes such as invertases and sucrases can be added to the sucrose to accelerate the hydrolysis reaction to produce invert sugar. Acid is an example of non-biological catalyst, when paired with heat, can accelerate the hydrolysis reaction. Once the invert sugar is made, it is less prone to crystallization compared to sucrose and thus, provides advantages for storage and in fed batch fermentation, which in the case of heterotrophic cultivation of microbes, including microalgae, there is a need for concentrated carbon source. In one embodiment, the carbon source is invert sugar, preferably in a concentrated form, preferably at least 800 g/liter, at least 900 g/liter, at least 1000 g/liter or at least 1100 g/liter prior to the cultivation step, which is optionally a fed batch cultivation. The invert sugar, preferably in a concentrated form, is fed to the cells over time as the cells grow and accumulate lipid.

In another embodiment of the methods of the invention, the carbon source is sucrose, including a complex feedstock containing sucrose, such as thick cane juice from sugar cane processing. Because of the higher densities of the cultures for heterotrophic oil production, the fixed carbon source (e.g., sucrose, glucose, etc.) is preferably in a concentrated form, preferably at least 500 g/liter, at least 600 g/liter, at least 700 g/liter or at least 800 g/liter of the fixed carbon source prior to the cultivation step, which is optionally a fed batch cultivation in which the material is fed to the cells over time as the cells grow and accumulate lipid. In the some cases, the carbon source is sucrose in the form of thick cane juice, preferably in a concentrated form, preferably at least 60% solids or about 770 g/liter sugar, at least 70% solids or about 925 g/liter sugar, or at least 80% solids or about 1125 g/liter sugar prior to the cultivation step, which is optionally a fed batch cultivation. The concentrated thick cane juice is fed to the cells over time as the cells grow and accumulate lipid In one embodiment, the culture medium further includes at least one sucrose utilization enzyme. In some cases, the culture medium includes a sucrose invertase. In one embodiment, the sucrose invertase enzyme is a secrectable sucrose invertase enzyme encoded by an exogenous sucrose invertase gene expressed by the population of microorganisms. Thus, in some cases, as described in more detail in Section IV, below, the microalgae has been genetically engineered to express a sucrose utilization enzyme, such as a sucrose transporter, a sucrose invertase, a hexokinase, a glucokinase, or a fructokinase.

Complex feedstocks containing sucrose include waste molasses from sugar cane processing; the use of this low-value waste product of sugar cane processing can provide significant cost savings in the production of hydrocarbons and other oils. Another complex feedstock containing sucrose that is useful in the methods of the invention is sorghum, including sorghum syrup and pure sorghum. *Sorghum* syrup is produced from the juice of sweet sorghum cane. Its sugar profile consists of mainly glucose (dextrose), fructose and sucrose.

Section IV. Genetic Engineering Methods and Materials

In some embodiments, present invention provides methods and materials for genetically modifying microalgal cells to enhance lipid production, modify the properties or proportions of components generated by the microorganism, or to improve or provide de novo growth characteristics on a variety of feedstock materials. Recombinant host cells useful in the methods provided herein include but not limited to recombinant *Chlorella protothecoides, Chlorella minutissima, Chlorella sorokiniana, Chlorella ellipsoidea, Chlorella* sp., *Chlorella emersonii, Prototheca moriformis, Prototheca zopfii, Prototheca wickerhamii, Prototheca blaschkaea, Prototheca krugani* (or *kruegani*), and *Prototheca stagnora* host cells.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see for example Gene. 1995 Oct. 16; 164(1):49-53).

1. Engineering Methods—Transformation

Cells can be transformed by any suitable technique including, e.g., biolistics, electroporation (see Maruyama et al. (2004), Biotechnology Techniques 8:821-826), glass bead transformation and silicon carbide whisker transformation. Another method that can be used involves forming protoplasts and using $CaCl_2$ and polyethylene glycol (PEG) to introduce recombinant DNA into microalgal cells (see Kim et al. (2002), Mar. Biotechnol. 4:63-73, which reports the use of this method for the transformation of *Chorella ellipsoidea*). Co-transformation of microalgae can be used to introduce two distinct vector molecules into a cell simultaneously (see for example Jakobiak et al. (2004) Protist 155(4):381-93).

Biolistic methods (see, for example, Sanford, Trends In Biotech. (1988) 6:299-302, U.S. Pat. No. 4,945,050; electroporation (Fromm et al., Proc. Nat'l. Acad. Sci. (USA) (1985) 82:5824-5828); use of a laser beam, microinjection or any other method capable of introducing DNA into a microalgae can also be used for transformation of a cell provided herein.

2. Engineering Methods—Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences. The mechanistic steps of this process, in most cases, include: (1) pairing of homologous DNA segments; (2) introduction of double-stranded breaks into the donor DNA molecule; (3) invasion of the template DNA molecule by the free donor DNA ends followed by DNA synthesis; and (4) resolution of double-strand break repair events that result in final recombination products.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, resulting in excellent genetic stability, even in the absence of genetic selection. Because different chromosomal loci will likey impact gene expression, even from heterologous promoters/UTRs, homologous recombination can be a method of querying loci in an unfamiliar genome environment and to assess the impact of these environments on gene expression.

Particularly useful genetic engineering applications using homologous recombination is to co-opt specific host regulatory elements such as promoters/UTRs to drive heterologous gene expression in a highly specific fashion. For example, ablation or knockout of desaturase genes/gene families with a heterologous gene encoding a selective marker might be expected to increase overall percentage of saturated fatty acids produced in the host cell. *protothecoides* Another approach to decreasing expression of an endogenous gene is to use an RNA-induced down-regulation or silencing of gene expression including, but not limited to an RNAi or antisense approach, as well as a dsRNA approach. Antisense, RNAi, RNA hairpin, and dsRNA approaches are well known in the art and include the introduction of an expression construct that when expressed as mRNA would lead to the formation of hairpin RNA or an expression construct containing a portion of the target gene that would be transcribed in the antisense orientation. All four approaches would result in the decreased expression of the target gene. Examples 3 and 4 describe expression constructs and working examples of the attenuation, or down-regulation of endogenous *Prototheca moriformis* lipid biosynthesis genes by an RNA hairpin approach.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activites such as substrate specificity, affinities and Km, and thus affecting the desired change in metabolism of the host cell. Homologous recombination provides a powerful means to manipulate the host nuclear or organellar genome resulting in gene targeting, gene conversion, gene deletion, gene duplication, gene inversion and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurance of undesired events. Other methods of increasing recombination efficiency include using PCR to generate transforming transgenic DNA containing linear ends homologous to the genomic sequences being targeted.

For purposes of non-limiting illustration, regions of donor DNA sequences that are useful for homologous recombination include the KE858 region of DNA in *Prototheca moriformis*. KE858 is a 1.3 kb, genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. This region and Examples of using this region for homologous recombination targeting has been described in PCT Publication No. WO 2010/063032 Another region of donor DNA that is useful is portions of the 6S genomic sequence. The use of this sequence in homologous recombination in *Prototheca morifomis* is described below in the Examples. These regions are potentially useful for integrating *Auxenochlorella prototothecoides* lipid biosynthesis genes into *Prototheca moriformis*. These corresponding regions can also be identified by homology and used in *Auxenochlorella protothecoides* as transgene integration sites.

For purposes of non-limiting illustration, regions of DNA sequences that are useful for homologous recombination include the photosynthetic related genes in *Chlorella protothecoides* plastid sequences. These include the gene regions corresponding to psbB, psbT, psbN, psbH, psbD, chlL, psbI, psaI, psbj, psbL, psbE, psbZ, psaM, psaK, chlB, psaA, psaB, and psaC (SEQ ID NO. 49111-49117). The intergenic regions between these may also be targeted.

3. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell. To aid the reader, this subsection is divided into subsections. Subsection A describes control sequences typically contained on vectors as well as novel control sequences provided by the present invention. Subsection B describes genes typically contained in vectors as well as novel codon optimization methods and genes prepared using them provided by the invention. Subsection C describes selectable markers contained on vectors and provided by the present invention. Subsection D describes methods and procedures used to identify genes.

A. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location within or outside the cell.

Thus, an exemplary vector design for expression of an exogenous gene in a microalgae contains a coding sequence for a desired gene product (for example, a selectable marker, a lipid pathway enzyme, or a sucrose utilization enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration. The promoterless method of transformation has been proven to work in microalgae (see for example Lumbreras, et. al. Plant Journal (1998) 14(4): pp. 441-447).

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Illustrative exogenous and/or endogenous promoters that are active in microalgae (as well as antibiotic resistance genes functional in microalgae) are described in PCT Pub. No. WO 2008/151149 and references cited therein The promoter used to express an exogenous gene can be the promoter naturally linked to that gene or can be a heterologous gene. Some promoters are active in more than one species of microalgae. Other promoters are species-specific. Illustrative promoters include promoters such as β-tubulin from *Chlamydomonas reinhardtii*, used in the Examples below, and viral promoters, such as cauliflower mosaic virus (CMV) and *chlorella* virus, which have been shown to be active in multiple species of microalgae (see for example Plant Cell Rep. 2005 March; 23(10-11):727-35; J. Microbiol. 2005 August; 43(4):361-5; Mar Biotechnol (NY). 2002 January; 4(1):63-73). Another promoter that is suitable for use for expression of exogenous genes in *Prototheca* is the *Chlorella sorokiniana* glutamate dehydrogenase promoter/5'UTR. Optionally, at least 10, 20, 30, 40, 50, or 60 nucleotides or more of these sequences containing a promoter are used. Illustrative promoters useful for expression of exogenous genes in *Prototheca* are listed in the sequence listing of this application, such as the promoter of the *Chlorella* HUP1 gene (SEQ ID NO:10) and the *Chlorella ellipsoidea* nitrate reductase promoter (SEQ ID NO:11).

*Chlorella* virus promoters can also be used to express genes in *Prototheca*, such as SEQ ID NOs: 1-7 of U.S. Pat. No. 6,395,965. Additional promoters active in *Prototheca* can be found, for example, in Biochem Biophys Res Commun. 1994 Oct. 14; 204(1):187-94; Plant Mol. Biol. 1994 October; 26(1):85-93; Virology. 2004 Aug. 15; 326(1):150-9; and Virology. 2004 Jan. 5; 318(1):214-23. Other useful promoters are described in detail in the Examples below.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule (e.g, glucose, as in SEQ ID NO:10), temperature (heat or cold), lack of nitrogen in culture media, etc. Suitable promoters can activate transcription of an essentially silent gene or upregulate, preferably substantially, transcription of an operably linked gene that is transcribed at a low level. Examples below describe additional inducible promoters that are useful in *Auxenochlorella* or *Prototheca* cells, including the ACP-P promoter.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

The present invention also provides in some embodiments control sequences and recombinant genes and vectors containing them that provide for the compartmentalized expression of a gene of interest. Organelles for targeting are chloroplasts (plastids) mitochondria. The endoplasmic reticulum is another key cellular compartment that may be desirable for targeting. Targeting sequences encode peptides that direct the expressed protein from its expression site to the targeted organelle. Chloroplast targeting sequences, plastid targeting sequences, mitochondrial targeting sequences and endoplasmic reticulum targeting sequences encode transit peptides that direct the expressed protein to the chloroplast, plastid, mitochondria or endoplasmic reticulum, respectively. In some embodiments, the present invention provides control sequences and recombinant genes and vectors containing them that provide for the secretion of a protein outside the cell. Secreted proteins include, for example, a sucrose invertase enzyme.

Proteins expressed in the nuclear genome can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors of the present invention to target expression of a protein to an *Auxenochlorella* or *Prototheca* plastid.

In another embodiment, the expression of polypeptide in *Auxenochlorella* is targeted to the plastid genome via homologous recombination. In place of using plastid targeting signals, recombination and expression of the lipid biosynthesis enzyme occurs within the plastid in this case. In some embodiments, a sequence is targeted to a site in the plastid encoding a protein related to photosynthetic growth.

In another embodiment, the expression of polypeptide in *Chlorella* is targeted to the plastid genome. In place of using plastid targeting signals as in the case of recombination in the nuclei, genetic recombination and expression of lipid biosynthesis enzymes occur within the plastid. In some embodiments, a sequence is targeted to a site in the plastid encoding a protein related to photosysntheic growth.

The Examples below describe the use of algal plastid targeting sequences to target heterologous proteins to the correct compartment in the host cell. cDNA libraries were made using *Prototheca moriformis* and *Chlorella protothecoides* cells and are described in PCT Publication No. WO 2010/063032.

In another embodiment, the expression of a polypeptide in *Prototheca* is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR—Plant Research International, includes the well known KDEL (SEQ ID NO: 49104) retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci U.S.A. 2005 Apr. 26; 102(17):6225-30.

In another embodiment of the present invention, a polypeptide is targeted for secretion outside the cell into the culture media. See Hawkins et al., Current Microbiology Vol. 38 (1999), pp. 335-341 for examples of secretion signals active in *Chlorella* that can be used, in accordance with the methods of the invention, in *Chlorella protothecoides*.

B. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated, in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker. Any of a wide variety of selectable markers can be employed in a transgene construct useful for transforming microalgae. Examples of suitable selectable markers include the G418 resistance gene, the nitrate reductase gene (see Dawson et al. (1997), Current Microbiology 35:356-362), the hygromycin phosphotransferase gene (HPT; see Kim et al. (2002), Mar. Biotechnol. 4:63-73), the neomycin phosphotransferase gene, and the ble gene, which confers resistance to phleomycin (Huang et al. (2007), Appl. Microbiol. Biotechnol.

72:197-205). Methods of determining sensitivity of microalgae to antibiotics are well known. For example, Mol Gen Genet. 1996 Oct. 16; 252(5):572-9.

Other selectable markers that are not antibiotic-based can also be employed in a transgene construct useful for transforming microalgae. Genes that confers the ability to utilize certain carbon sources that were previously unable to be utilized by the microalgae can also be used as a selectable marker. By way of illustration, *Prototheca moriformis* strains typically grow poorly, if at all, on sucrose. Using a construct containing a sucrose invertase gene can confer the ability of positive transformants to grow on sucrose as a carbon substrate. Additional details on using sucrose utilization as a selectable marker along with other selectable markers are discussed below. We provide herein an example of *Auxenochlorella prototheocoides* transformed with sucrose invertase used as a selectable marker.

For purposes of the present invention, the expression vector used to prepare a recombinant host cell of the invention will include at least two, and often three, genes, if one of the genes is a selectable marker. For example, a genetically engineered *Prototheca* cell can be made by transformation with vectors of the invention that comprise, in addition to a selectable marker, one or more exogenous genes, such as, for example, sucrose invertase gene or acyl ACP-thioesterase gene. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of different inducible (or constitutive) promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced).

In other embodiments, the two or more exogenous genes (in addition to any selectable marker) are: a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In one embodiment, the vector provides for the combination of a fatty acyl-ACP thioesterase, a fatty acyl-CoA reductase, and a fatty aldehyde decarbonylase to generate alkanes. In each of these embodiments, one or more of the exogenous genes can be expressed using an inducible promoter.

Other illustrative vectors of the invention that express two or more exogenous genes include those encoding both a sucrose transporter and a sucrose invertase enzyme and those encoding both a selectable marker and a secreted sucrose invertase. The recombinant *Prototheca* transformed with either type of vector produce lipids at lower manufacturing cost due to the engineered ability to use sugar cane (and sugar cane-derived sugars) as a carbon source. Insertion of the two exogenous genes described above can be combined with the disruption of polysaccharide biosynthesis through directed and/or random mutagenesis, which steers ever greater carbon flux into lipid production. Individually and in combination, trophic conversion, engineering to alter lipid production and treatment with exogenous enzymes alter the lipid composition produced by a microorganism. The alteration can be a change in the amount of lipids produced, the amount of one or more hydrocarbon species produced relative to other lipids, and/or the types of lipid species produced in the microorganism. For example, microalgae can be engineered to produce a higher amount and/or percentage of TAGs.

Transgenes that alter the fatty acid profiles of host organisms may be expressed in numerous eukaryotic microbes. Examples of expression of transgenes in eukaryotic microbes including *Chlamydomonas reinhardtii, Chlorella ellipsoidea, Chlorella saccarophila, Chlorella vulgaris, Chlorella kessleri, Chlorella sorokiniana, Haematococcus pluvialis, Gonium pectorale, Volvox carteri, Dunaliella tertiolecta, Dunaliella viridis, Dunaliella salina, Closterium peracerosum-strigosum-littorale complex, Nannochloropsis* sp., *Thalassiosira pseudonana, Phaeodactylum tricornutum, Navicula saprophila, Cylindrotheca fusiformis, Cyclotella cryptica, Symbiodinium microadriacticum, Amphidinium* sp., *Chaetoceros* sp., *Mortierella alpina,* and *Yarrowia lipolytica* may be found in the scientific literature. These expression techniques may be combined with the teachings of the present invention to produce engineered microorganisms with altered fatty acid profiles.

Transgenes that alter the fatty acid profiles of host organisms or alter the regiospecific distribution of glycerolipids produced by host organisms can also be expressed in numerous prokaryotic microbes. Examples of expression of transgenes in oleaginous microbes including *Rhodococcus opacus* may be found in the literature. These expression techniques may be combined with the teachings of the present invention to produce engineered microorganisms with altered fatty acid profiles.

For optimal expression of a recombinant protein, it is beneficial to employ coding sequences that produce mRNA with codons preferentially used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA. Methods of recoding genes for expression in microalgae are described in U.S. Pat. No. 7,135,290. In some cases it is preferable to use the most preferred codon in all instances. In other cases it may be preferable to use the entire codon usage table, such that rare codons are still used, albeit rarely, and to provide additional algorithmhs that seek to minimize secondary structure of the mRNA transcript, particularly in the 5' leader region. An exemplary program for this operation is PySplicer. In other cases, it may be desirable to produce and screen a library of different variations of the codon-optimized gene. Additional information for codon optimization is available, e.g., at the codon usage database of GenBank. As non-limiting examples, codon usage in *Chlorella pyrenoidosa, Dunaliella saltha, Chlorella prototheocoides*, and *Chlorella prototheocoides* plastid are shown in Tables 2-6. For genes targeted to the nuclear genome, the nuclear codon usage table is preferred. For lipid biosynthesis genes directly targeted to the plastid genome by plastid transformation methods, the plastid codon usage table is preferred.

Codon usage in *Prototheca* species was analyzed by studying cDNA sequences isolated from *Prototheca mori-*

*formis*. This analysis represents the interrogation over 24,000 codons and resulted in Table 2 below. In addition, the gene predictions for the entire nuclear genome were analyzed for codon usage, resulting in Table 5b below.

Codon usage in *Chlorella protothecoides* plastid was analyzed by studying the entire plastid genome sequence isolated from *Chlorella protothecoides*. This analysis represents the interrogation 20,889 codons resulting in Tables 5c-d below.

TABLE 2

Illustrative preferred codon usage in *Prototheca* strains.

| Ala | GCG | 345 (0.36) | Asn | AAT | 8 (0.04) |
|---|---|---|---|---|---|
|  | GCA | 66 (0.07) |  | AAC | 201 (0.96) |
|  | GCT | 101 (0.11) | Pro | CCG | 161 (0.29) |
|  | GCC | 442 (0.46) |  | CCA | 49 (0.09) |
| Cys | TGT | 12 (0.10) |  | CCT | 71 (0.13) |
|  | TGC | 105 (0.90) |  | CCC | 267 (0.49) |
| Asp | GAT | 43 (0.12) | Gln | CAG | 226 (0.82) |
|  | GAC | 316 (0.88) |  | CAA | 48 (0.18) |
| Glu | GAG | 377 (0.96) | Arg | AGG | 33 (0.06) |
|  | GAA | 14 (0.04) |  | AGA | 14 (0.02) |
| Phe | TTT | 89 (0.29) |  | CGG | 102 (0.18) |
|  | TTC | 216 (0.71) |  | CGA | 49 (0.08) |
| Gly | GGG | 92 (0.12) |  | CGT | 51 (0.09) |
|  | GGA | 56 (0.07) |  | CGC | 331 (0.57) |
|  | GGT | 76 (0.10) | Ser | AGT | 16 (0.03) |
|  | GGC | 559 (0.71) |  | AGC | 123 (0.22) |
| His | CAT | 42 (0.21) |  | TCG | 152 (0.28) |
|  | CAC | 154 (0.79) |  | TCA | 31 (0.06) |
| Ile | ATA | 4 (0.01) |  | TCT | 55 (0.10) |
|  | ATT | 30 (0.08) |  | TCC | 173 (0.31) |
|  | ATC | 338 (0.91) | Thr | ACG | 184 (0.38) |
| Lys | AAG | 284 (0.98) |  | ACA | 24 (0.05) |
|  | AAA | 7 (0.02) |  | ACT | 21 (0.05) |
| Leu | TTG | 26 (0.04) |  | ACC | 249 (0.52) |
|  | TTA | 3 (0.00) | Val | GTG | 308 (0.50) |
|  | CTG | 447 (0.61) |  | GTA | 9 (0.01) |
|  | CTA | 20 (0.03) |  | GTT | 35 (0.06) |
|  | CTT | 45 (0.06) |  | GTC | 262 (0.43) |
|  | CTC | 190 (0.26) | Trp | TGG | 107 (1.00) |
| Met | ATG | 191 (1.00) | Tyr | TAT | 10 (0.05) |
|  |  |  |  | TAC | 180 (0.95) |
|  |  |  | Stop | TGA/TAG/TAA |  |

TABLE 3

Codon usage in *Chlorella pyrenoidosa*.

| Phe | UUU | 39 (0.82) | Ser | UCU | 50 (1.04) |
|---|---|---|---|---|---|
|  | UUC | 56 (1.18) |  | UCC | 60 (1.25) |
| Leu | UUA | 10 (0.20) |  | UCA | 6 (0.96) |
|  | UUG | 46 (0.91) |  | UCG | 43 (0.89) |
| Tyr | UAU | 15 (0.59) | Cys | UGU | 46 (0.77) |
|  | UAC | 36 (1.41) |  | UGC | 73 (1.23) |
| ter | UAA | 9 (0.00) | ter | UGA | 43 (0.00) |
| ter | UAG | 15 (0.00) | Trp | UGG | 69 (1.00) |
| Leu | CUU | 49 (0.97) | Pro | CCU | 80 (0.98) |
|  | CUC | 73 (1.45) |  | CCC | 88 (1.08) |
|  | CUA | 22 (0.44) |  | CCA | 93 (1.14) |
|  | CUG | 103 (2.04) |  | CCG | 65 (0.80) |
| His | CAU | 50 (0.88) | Arg | CGU | 39 (0.76) |
|  | CAC | 3 (1.12) |  | CGC | 63 (1.23) |
| Gln | CAA | 59 (0.84) |  | CGA | 46 (0.90) |
|  | CAG | 2 (1.16) |  | CGG | 47 (0.92) |
| Ile | AUU | 24 (0.69) | Thr | ACU | 32 (0.67) |
|  | AUC | 61 (1.76) |  | ACC | 76 (1.60) |
|  | AUA | 19 (0.55) |  | ACA | 41 (0.86) |
| Met | AUG | 42 (1.00) |  | ACG | 41 (0.86) |
| Asn | AAU | 26 (0.75) | Ser | AGU | 23 (0.48) |
|  | AAC | 3 (1.25) |  | AGC | 67 (1.39) |
| Lys | AAA | 32 (0.54) | Arg | AGA | 51 (1.00) |
|  | AAG | 86 (1.46) |  | AGG | 61 (1.19) |
| Val | GUU | 36 (0.75) | Ala | GCU | 57 (0.79) |
|  | GUC | 54 (1.13) |  | GCC | 97 (1.34) |

TABLE 3-continued

Codon usage in *Chlorella pyrenoidosa*.

|  | GUA | 30 (0.63) |  | GCA | 89 (1.23) |
|---|---|---|---|---|---|
|  | GUG | 71 (1.49) |  | GCG | 47 (0.65) |
| Asp | GAU | 60 (0.95) | Gly | GGU | 35 (0.60) |
|  | GAC | 66 (1.05) |  | GGC | 78 (1.33) |
| Glu | GAA | 41 (0.68) |  | GGA | 54 (0.92) |
|  | GAG | 80 (1.32) |  | GGG | 67 (1.15) |

TABLE 4

Preferred codon usage in *Dunaliella salina*.

| TTC (Phe) | TAC (Tyr) | TGC (Cys) | TAA (Stop) |
|---|---|---|---|
| TGG (Trp) | CCC (Pro) | CAC (His) | CGC (Arg) |
| CTG (Leu) | CAG (Gln) | ATC (Ile) | ACC (Thr) |
| AAC (Asn) | AGC (Ser) | ATG (Met) | AAG (Lys) |
| GCC (Ala) | GAC (Asp) | GGC (Gly) | GTG (Val) |
| GAG (Glu) |  |  |  |

TABLE 5a

Preferred codon usage in *Chlorella protothecoides*.

| TTC (Phe) | TAC (Tyr) | TGC (Cys) | TGA (Stop) |
|---|---|---|---|
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) |  |  |  |

TABLE 5b

Codon usage in *Auxenochlorella protothecoides* Nuclear genome

| Amino Acid | Codon | Number (Fraction) |
|---|---|---|
| Gly | GGG | 53727.00 (0.26) |
|  | GGA | 35897.00 (0.18) |
|  | GGT | 24027.00 (0.12) |
|  | GGC | 90622.00 (0.44) |
| Glu | GAG | 70388.00 (0.83) |
|  | GAA | 14074.00 (0.17) |
| Asp | GAT | 16562.00 (0.23) |
|  | GAC | 55282.00 (0.77) |
| Val | GTG | 57084.00 (0.54) |
|  | GTA | 6904.00 (0.07) |
|  | GTT | 8591.00 (0.08) |
|  | GTC | 33104.00 (0.31) |
| Ala | GCG | 78923.00 (0.31) |
|  | GCA | 39748.00 (0.15) |
|  | GCT | 40702.00 (0.16) |
|  | GCC | 96742.00 (0.38) |
| Arg | AGG | 35406.00 (0.16) |
|  | AGA | 14056.00 (0.06) |
|  | CGG | 51465.00 (0.23) |
|  | CGA | 26066.00 (0.12) |
|  | CGT | 20310.00 (0.09) |
|  | CGC | 72278.00 (0.33) |
| Ser | AGT | 9434.00 (0.07) |
|  | AGC | 39915.00 (0.27) |
|  | TCG | 24945.00 (0.17) |
|  | TCA | 17117.00 (0.12) |
|  | TCT | 14344.00 (0.10) |
|  | TCC | 39776.00 (0.27) |
| Lys | AAG | 39479.00 (0.77) |
|  | AAA | 11529.00 (0.23) |
| Asn | AAT | 4955.00 (0.18) |
|  | AAC | 22524.00 (0.82) |
| Met | ATG | 30760.00 (1.00) |
| Ile | ATA | 2327.00 (0.06) |
|  | ATT | 5116.00 (0.12) |
|  | ATC | 34530.00 (0.82) |

TABLE 5b-continued

Codon usage in *Auxenochlorella protothecoides* Nuclear genome

| Amino Acid | Codon | Number (Fraction) |
|---|---|---|
| Thr | ACG | 33535.00 (0.32) |
|  | ACA | 15840.00 (0.15) |
|  | ACT | 11762.00 (0.11) |
|  | ACC | 45187.00 (0.42) |
| Trp | TGG | 50365.00 (1.00) |
| Stop | TGA | 14946.00 (0.87) |
|  | TAG | 1427.00 (0.08) |
|  | TAA | 815.00 (0.05) |
| Cys | TGT | 11915.00 (0.23) |
|  | TGC | 40379.00 (0.77) |
| Tyr | TAT | 3961.00 (0.15) |
|  | TAC | 22665.00 (0.85) |
| Leu | TTG | 11031.00 (0.06) |
|  | TTA | 1058.00 (0.01) |
| Phe | TTT | 11436.00 (0.29) |
|  | TTC | 27674.00 (0.71) |
| Gln | CAG | 52937.00 (0.72) |
|  | CAA | 20035.00 (0.28) |
| His | CAT | 21799.00 (0.37) |
|  | CAC | 36516.00 (0.63) |
| Leu | CTG | 96752.00 (0.56) |
|  | CTA | 8161.00 (0.05) |
|  | CTT | 15436.00 (0.09) |
|  | CTC | 39575.00 (0.23) |
| Pro | CCG | 48421.00 (0.26) |
|  | CCA | 36278.00 (0.20) |
|  | CCT | 41156.00 (0.22) |
|  | CCC | 60326.00 (0.32) |

TABLE 5c

Preferred codon usage in *Chlorella protothecoides* plastid

| TTT (Phe) | TAT (Tyr) | TGT (Cys) | CGT (Arg) |
|---|---|---|---|
| TGG (Trp) | CCA (Pro) | CAT (His) | ACA/ACT (Thr) |
| TTA (Leu) | CAA (Gln) | ATT (Ile) | AAA (Lys) |
| GAT (Asp) | TCT (Ser) | ATG (Met) | GTT (Val) |
| GCT (Ala) | AAT (Asn) | GGT (Gly) |  |
| GAA (Glu) |  |  |  |

TABLE 5d

Codon usage in *Chlorella protothecoides* plastid

| Ala | GCA | 494 (0.37) | Asn | AAC | 228 (0.20) |
|---|---|---|---|---|---|
|  | GCC | 69 (0.05) |  | AAT | 926 (0.80) |
|  | GCG | 129 (0.10) | Pro | CCA | 419 (0.46) |
|  | GCT | 638 (0.48) |  | CCC | 54 (0.06) |
| Cys | TGC | 39 (0.22) |  | CCG | 101 (0.11) |
|  | TGT | 136 (0.78) |  | CCT | 340 (0.37) |
| Asp | GAC | 125 (0.15) | Gln | CAA | 791 (0.92) |
|  | GAT | 722 (0.85) |  | CAG | 72 (0.08) |
| Glu | GAA | 937 (0.84) | Arg | AGA | 203 (0.21) |
|  | GAG | 178 (0.16) |  | AGG | 26 (0.03) |
| Phe | TTC | 137 (0.12) |  | CGA | 198 (0.21) |
|  | TTT | 1038 (0.88) |  | CGC | 86 (0.09) |
| Gly | GGA | 358 (0.26) |  | CGG | 69 (0.07) |
|  | GGC | 119 (0.09) |  | CGT | 371 (0.39) |
|  | GGG | 183 (0.13) | Ser | AGC | 64 (0.05) |
|  | GGT | 724 (0.52) |  | AGT | 350 (0.26) |
| His | CAC | 105 (0.25) |  | TCA | 387 (0.28) |
|  | CAT | 317 (0.75) |  | TCC | 37 (0.03) |
| Ile | ATA | 411 (0.25) |  | TCG | 84 (0.06) |
|  | ATC | 129 (0.08) |  | TCT | 439 (0.32) |
|  | ATT | 1090 (0.67) | Thr | ACA | 511 (0.44) |
| Lys | AAA | 1331 (0.93) |  | ACC | 67 (0.06) |
|  | AAG | 94 (0.07) |  | ACG | 68 (0.06) |
| Leu | CTA | 146 (0.07) |  | ACT | 512 (0.44) |
|  | CTC | 34 (0.02) | Val | GTA | 498 (0.39) |
|  | CTG | 18 (0.01) |  | GTC | 30 (0.02) |
|  | CTT | 399 (0.18) |  | GTG | 87 (0.07) |

TABLE 5d-continued

Codon usage in *Chlorella protothecoides* plastid

|  | TTA | 1481 (0.67) |  | GTT | 654 (0.52) |
|---|---|---|---|---|---|
|  | TTG | 132 (0.06) | Trp | TGG | 309 (1.00) |
| Met | ATG | 394 (1.00) | Tyr | TAC | 124 (0.17) |
|  |  |  |  | TAT | 596 (0.83) |

C. Selectable Markers

Sucrose Utilization

In one embodiment, the recombinant cell provided herein further contains one or more exogenous sucrose utilization genes. In various embodiments, the one or more genes encode one or more proteins selected from the group consisting of a fructokinase, a glucokinase, a hexokinase, a sucrose invertase, a sucrose transporter. For example, expression of a sucrose transporter and a sucrose invertase allows the cell to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are GenBank accession numbers CAD91334, CAB92307, and CAA53390. Examples of suitable fructokinases are GenBank accession numbers P26984, P26420 and CAA43322.

In one embodiment, the present invention provides a *Prototheca* host cell that secretes a sucrose invertase. Secretion of a sucrose invertase obviates the need for expression of a transporter that can transport sucrose into the cell. This is because a secreted invertase catalyzes the conversion of a molecule of sucrose into a molecule of glucose and a molecule of fructose, both of which can be transported and utilized by microbes provided by the invention. For example, expression of a sucrose invertase with a secretion signal (such as that of SEQ ID NO:12 (from yeast), SEQ ID NO:13 (from higher plants), SEQ ID NO:14 (eukaryotic consensus secretion signal), and SEQ ID NO:15 (combination of signal sequence from higher plants and eukaryotic consensus) generates invertase activity outside the cell. Expression of such a protein, as enabled by the genetic engineering methodology disclosed herein, allows cells already capable of utilizing extracellular glucose as an energy source to utilize sucrose as an extracellular energy source.

*Prototheca* species expressing an invertase in media containing sucrose are a preferred microalgal species for the production of oil. The expression and extracellular targeting of this fully active protein allows the resulting host cells to grow on sucrose, whereas their non-transformed counterparts cannot. Thus, the present invention provides *Prototheca* recombinant cells with a codon-optimized invertase gene (SEQ ID NO:16), including but not limited to the yeast invertase gene, integrated into their genome such that the invertase gene is expressed as assessed by invertase activity and sucrose hydrolysis.

Examples of suitable sucrose invertases include those identified by GenBank accession numbers CAB95010, NP 012104 (SEQ ID NO:17), and CAA06839. Non-limiting examples of suitable invertases are include those described in PCT Publication No. WO 2010/063032, incorporated herein by reference.

The secretion of an invertase to the culture medium by *Prototheca* enable the cells to grow as well on waste molasses from sugar cane processing as they do on pure reagent-grade glucose; the use of this low-value waste product of sugar cane processing can provide significant cost savings in the production of lipids and other oils. Thus, the present invention provides a microbial culture containing a population of *Prototheca* microorganisms, and a culture medium comprising (i) sucrose and (ii) a sucrose invertase enzyme. In various embodiments the sucrose in the culture comes from sorghum, sugar beet, sugar cane, molasses, or depolymerized cellulosic material (which may optionally contain lignin). In another aspect, the methods and reagents of the invention significantly increase the number and type of feedstocks that can be utilized by recombinant *Prototheca*. While the microbes exemplified here are altered such that they can utilize sucrose, the methods and reagents of the invention can be applied so that feedstocks such as cellulosics are utilizable by an engineered host microbe of the invention with the ability to secrete cellulases, pectinases, isomerases, or the like, such that the breakdown products of the enzymatic reactions are no longer just simply tolerated but rather utilized as a carbon source by the host.

D. Sequence Determination

A variety of methods may be employed for the identification of gene sequences and amino acid sequences of lipid biosynthetic pathway genes and enzymes. Sequences of polynucleotides (e.g., genomic DNA, cDNA, RNA, PCR-amplified nucleotides) may be determined through sequencing technologies including but not limited to Sanger sequencing, pyrosequencing, sequencing by synthesis, sequencing by oligonucleotide probe ligation, and real time sequencing. One skilled in the art may compare nucleotide sequences to published databases of genomic sequences or expressed sequences. Where a DNA sequence is determined or disclosed, one skilled in the art may compare segments from published exon sequences, or may assemble exon sequences into a reconstructed sequence that does not contain intronic sequences. Sequences of polynucleotides may also be translated into amino acids, peptides, polypeptides or proteins through a variety of methods including but not limited to manual translation or computer-automated translation with bioinformatics software commonly known in the art. Comparison methods of sequenced DNA, RNA, amino acids, peptides, or proteins may include but are not limited to manual evaluation of the sequence or computer-automated sequence comparison and identification using algorithms such as BLAST (Basic Local Alignment Search Tool; Altschul, S. E, et al, (1993)/. *Mol. Biol.* 215:403-410; see also www.ncbi.nlm.nih.gov/BLAST/).

The instant specification teaches partial or complete amino acid and nucleotide sequences encoding one or more particular microbial genes and proteins. The skilled artisan, having the benefit of the sequences as reported herein, may now use all or a portion of the disclosed sequences for purposes known to those skilled in this art.

Genomic DNA from *Chlorella protothecoides* (UTEX 250) was isolated using standard protocols, and sequenced using Illumina HiSeq Paired-End sequencing, with 100 bp reads and approximatgely 450 by fragments. Genomic DNA is prepared using standard protocols and fragmented by hydrodynamic shearing. Sequencing reads were quality trimmed and filtered using FastX tools. Genome data was assembled using Velvet (Zerbino et al, Velvet: algorithms for de novo short read assembly using de Bruijn graphs, Genome Research, May 2008) using an optimized kmer and other default parameters. The assembly resulted in 31619 continuous sequences (SEQ ID NO: 17485-49103). Further sequencing was provided using Illumina HiSeq sequencing (100 bp paired end reads, ~450 bp fragment size) using a Mobio clean-up kit to remove secondary contaminants. Data was analyzed using FastQC. Data was cleaned and de-duplicated using a custom read processing pipeline that removes PCR duplicates, trims ends based on quality scores, and trims problematic 5' regions from reads. Illumina data was assembled using velvet with a minimum coverage cutoff to assemble only plastid components that are present in high-coverage, and with a maximum coverage cutoff that focuses the assembly on lower-coverage components, thus providing an enhanced assembly of the nuclear genome.

Annotation was performed using the MAKER pipeline, and genes and proteins (e.g. SEQ ID NO: 61-17484) were identified by BLAST (NCBI database). Briefly, MAKER runs gene modeling programs SNAP and Augustus, using default HMMs (eukaryotic general and *Chlamydomonas* were used here respectively) and then provides gene models for each gene on the genome. These gene models were further annotated by blasting them against the NCBI nr database to provide functional annotation. Genomic assemblies were further annotated using Augustus with a HMM trained on a *Prototheca* species to provide gene modeling that is closer to the native (*Auxenochlorella*) organism. These gene models were trained through multiple rounds of bootstrapping. Gene models obtained were of generally high quality. These gene models were annotated with BLAST (blastp vs. nr at NCBI, as of November 2013) and Interpro.

Given a gene or transcriptome fragment, one of skill in the art may retreive full-length transcripts (cDNA) or sequence genomic regions using various techniques. RACE (Rapid Amplification of cDNA ends) can be used to obtain a full-length cDNA, given even a short segment of a transcript. RAGE (Rapid Amplification of Genomic Ends) can be used to identify, even given a short segment of a transcript, the flanking genomic regions corresponding to a gene.

A given base position is indicated with a code as shown in the table below.

Base Codes

| | |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N | any base |
| . or - | gap |
| * | stop/nonsense codon |
| ? | unknown amino acid |

In some cases the sequence may contain Ns, representing unknown bases in a gap of size defined by the paired ends. These bases can be filled in by standard gap-filling techniques. N's will be represented as X's and any invalid codons will be represented as question marks ("?") in the translated amino acid sequence.

Section V. Genetically Engineered Cells

In a first aspect, the present invention provides a genetically engineered cell in one or more lipid biosynthesis genes have been modified to increase or decrease expression of such one or more genes such that the fatty acid profile of the genetically engineered strain differs from that of the strain from which it was derived. In one embodiment, at least two genes have been modified. In various embodiments, the genetic modifications include one or more of the following modifications: (i) attenuation of a gene or its enzymatic product; and (ii) increased expression of a gene or its enzymatic product; (iii) altered activity of a gene or its enzymatic product.

In various embodiments, the genetically engineered cell has one or more attenuated genes, wherein the genes attenuated have been attenuated by a means selected from the group consisting of a homologous recombination event and introduction of an exogenous gene that codes for an interfering RNA. In various embodiments, one or more alleles of a gene are attenuated.

In various embodiments, the genetically engineered cell has one or more over-expressed genes, wherein the genes over-expressed have been up-regulated by a means selected from the group consisting of introduction of additional copies of said gene into said cell; introduction of new expression control elements for said gene; and alteration of the protein-coding sequence of the gene. In various embodiments, one or more alleles of a gene are over-expressed.

In various embodiments, the modified genes of the genetically engineered cell are selected from the group consisting of lipid biosynthesis genes presented in Table 1. In various embodiments, the genetically engineered cell comprises an exogenous gene selected from the group consisting of lipid biosynthesis genes presented in Table 1. In various embodiments, the genetically engineered cell comprises one or more over-expressed alleles of a gene, the gene selected from the group consisting of lipid biosynthesis genes presented in Table 1. In various embodiments, the genetically engineered cell has an attenuated gene selected from the group consisting of lipid biosynthesis genes presented in Table 1. In various embodiments, the genetically engineered cell has one or more attenuated alleles of a gene, the gene selected from the group consisting of lipid biosynthesis genes presented in Table 1.

In various embodiments, the genetically engineered cell has one or more overexpressed genes, wherein the expression of the genes have been increased by a means selected from the group consisting of introduction of additional copies of said gene into said cell; and introduction of new expression control elements for said gene. In various embodiments, the overexpressed gene is an exogenous gene.

In various embodiments, the modified genes of the genetically engineered cell are selected from the group consisting of lipid biosynthesis genes presented in Table 1.

In various embodiments, the genetically engineered cell has an up-regulated gene selected from the group consisting of lipid biosynthesis genes presented in Table 1. In various embodiments, the genetically engineered cell has an attenuated gene selected from the group consisting of lipid biosynthesis genes presented in Table 1. In various embodiments, the genetically engineered cell has a fatty acid profile selected from the group consisting of: 3% to 60% C8:0, 3% to 60% C10:0, 3% to 70% C12:0, 3% to 95% C14:0, 3% to 95% C16:0, 3% to 95% C18:0, 3% to 95% C18:1, 3% to 60% C18:2, 1% to 60% C18:3 or combinations thereof. In various embodiments, the ratio of C10:0 to C12:0 is at least 3:1. In some cases, the ratio of C10:0 to C14:0 is at least 10:1. In various embodiments, the genetically engineered cell has a fatty acid profile of at least 40% saturated fatty acids, of at least 60% saturated fatty acids, or at least 85% saturated fatty acids.

The present invention also provides recombinant cells that have been modified to contain one or more exogenous genes encoding lipid biosyntheis enzymes such as, for example, a fatty acyl-ACP thioesterase (see Example 4) or a ketoacyl-ACP synthase II (see Example 5). In some embodiments, genes encoding a fatty acyl-ACP thioesterase and a naturally co-expressed acyl carrier protein are transformed into a *Prototheca* cell, optionally with one or more genes encoding other lipid biosynthesis genes. In other embodiments, the ACP and the fatty acyl-ACP thioesterase may have an affinity for one another that imparts an advantage when the two are used together in the microbes and methods of the present invention, irrespective of whether they are or are not naturally co-expressed in a particular tissue or organism. Thus, the present invention contemplates both naturally co-expressed pairs of these enzymes as well as those that share an affinity for interacting with one another to facilitate cleavage of a length-specific carbon chain from the ACP.

In still other embodiments, an exogenous gene encoding a desaturase is transformed into a cell in conjunction with one or more genes encoding other lipid biosynthesis genes to provide modifications with respect to lipid saturation. In other embodiments, an endogenous desaturase gene is over-expressed (e.g., through the introduction of additonal copies off the gene) in a cell. In some embodiments, the desaturase can be selected with reference to a desired carbon chain length, such that the desaturase is capable of making location specific modifications within a specified carbon-length substrate, or substrates having a carbon-length within a specified range. In another embodiment, if the desired fatty acid profile is an increase in monounsaturates (such as C16:1 and/or C18:1) overexpression of a SAD or expression of a heterologous SAD can be coupled with the silencing or inactivation (e.g., through mutation, RNAi, antisense, or knockout of an endogenous desaturase gene, etc.) of a fatty acyl desaturase (FAD) or another desaturase gene.

In other embodiments, the cell has been modified to have an attenuated endogenous desaturase gene, wherein the attenuation renders the gene or desaturase enzyme inactive. In some cases, the mutated endogenous desaturase gene is a fatty acid desaturase (FAD). In other cases, the mutated endogenous desaturase gene is a stearoyl Acyl carrier protein desaturase (SAD). Example 3 below describes the targeted ablation or knockout of stearoyl-ACP desaturases and delta 12 fatty acid desaturases. Example 3 also describes the use of RNAi or antisense constructs to decrease the expression of an endogenous desaturase gene.

In some cases, it may be advantageous to pair one or more of the genetic engineering techniques in order to achieve a trangenic cell that produces the desired lipid profile. In one embodiment, a cell comprises an attenuated endogenous thioestease gene and one or more exogenous gene. In non-limiting examples, a cell with an attenuated endogenous thioesterase gene can also express an exogenous fatty acyl-ACP thioesterase gene and/or a sucrose invertase gene. Example 4 below describes a transgenic cell containing a targeted ablation or knockout of an endogenous thioesterase and also expresses a *Cuphea wrightii* FatB2 C10:0-C14:0 preferring thioesterase and a sucrose invertase.

In other embodiments, one allele of a lipid biosyntheis gene has been attenuated. In additional embodiments, two or more alleles of a lipid biosyntheis gene have been attenuated. Example 3 below describes the targeted knockout of multiple alleles of stearoyl-ACP desaturase. In some cases, the targeted knockout of different alleles of a gene may result in different effects on fatty acid profiles.

In other embodiments, the targeted knockout gene is located on the plastid genome. This could be paired with one or more genetic engineering techniques targeting the nuclear genome. In non-limiting examples, a cell optinally having an attenuated endogenous thioesterase gene can also express an exogenous fatty acyl-ACP thioesterase gene from within the plastid.

In other embodiments, the targeted knockout gene is located on the plastid genome. This could be paired with one or more genetic engineering techniques targeting the nuclear genome. In non-limiting examples, a cell optinally having an attenuated endogenous thioesterase gene can also express an exogenous fatty acyl-ACP thioesterase gene from within the plastid. Expression of the thioesterase in the plastid increases total copy number (due to presence of multiple plastid organelles per cell) and negates the need for a plastid transit peptide. In this case a preferred method is to use the plastid codon usage table provided herein. The entire plastid sequece for *Auxenochlorella protothecoides*, useful for providing targeting regions and gene targets for overexpression or knockdown, and for comprehensive identification of strain identity, is disclosed in SEQ ID NO: 49118.

Section VI. Microbial Oils

For the production of oil in accordance with the methods of the invention, it is preferable to culture cells in the dark, as is the case, for example, when using extremely large (40,000 liter and higher) fermentors that do not allow light to strike the culture. Species provided herein are grown and propagated for the production of oil in a medium containing a fixed carbon source and in the absence of light; such growth is known as heterotrophic growth.

As an example, an inoculum of lipid-producing microalgal cells are introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after then end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of lipid species produced, and/or production of a specific oil.

As discussed above, a bioreactor or fermenter is used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells. Lipid production by cells disclosed herein can occur during the log phase or thereafter, including the stationary phase wherein nutrients are supplied, or still available, to allow the continuation of lipid production in the absence of cell division.

Preferably, microorganisms grown using conditions described herein and known in the art comprise at least about 20% by weight of lipid, preferably at least about 40% by weight, more preferably at least about 50% by weight, and most preferably at least about 60% by weight. Process conditions can be adjusted to increase the yield of lipids suitable for a particular use and/or to reduce production cost. For example, in certain embodiments, a microalgae is cultured in the presence of a limiting concentration of one or more nutrients, such as, for example, nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 50%, 100%, 200%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period. Lipid content of cells can be increased by continuing the culture for increased periods of time while providing an excess of carbon, but limiting or no nitrogen.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using constructs and techniques such as those described above.

The specific examples of bioreactors, culture conditions, and heterotrophic growth and propagation methods described herein can be combined in any suitable manner to improve efficiencies of microbial growth and lipid and/or protein production.

Microalgal biomass with a high percentage of oil/lipid accumulation by dry weight has been generated using different methods of culture, which are known in the art (see PCT Pub. No. WO 2008/151149). Microalgal biomass generated by the culture methods described herein and useful in accordance with the present invention comprises at least 10% microalgal oil by dry weight. In some embodiments, the microalgal biomass comprises at least 25%, at least 50%, at least 55%, or at least 60% microalgal oil by dry weight. In some embodiments, the microalgal biomass contains from 10-90% microalgal oil, from 25-75%

The microalgal oil of the biomass described herein, or extracted from the biomass for use in the methods and compositions of the present invention can comprise glycerolipids with one or more distinct fatty acid ester side chains. Glycerolipids are comprised of a glycerol molecule esterified to one, two or three fatty acid molecules, which can be of varying lengths and have varying degrees of saturation. The length and saturation characteristics of the fatty acid molecules (and the microalgal oils) can be manipulated to modify the properties or proportions of the fatty acid molecules in the microalgal oils of the present invention via culture conditions or via lipid pathway engineering, as described in more detail in Section IV, below. Thus, specific blends of algal oil can be prepared either within a single species of algae by mixing together the biomass or algal oil from two or more species of microalgae, or by blending algal oil of the invention with oils from other sources such as soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, *Cuphea*, flax, peanut, choice white grease, lard, Camelina sativa, mustard seed, cashew nut, oats, lupine, kenaf, calendula, help, coffee, linseed (flax), hazelnut, euphorbia, pumpkin seed, coriander, camellia, sesame, safflower, rice, tung tree, cocoa, copra, pium poppy, castor beans, pecan, jojoba, macadamia, Brazil nuts, avocado, petroleum, or a distillate fraction of any of the preceding oils.

The oil composition, i.e., the properties and proportions of the fatty acid constituents of the glycerolipids, can also be manipulated by combining biomass or oil from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids Generally, *Prototheca* strains have very little or no fatty acids with the chain length C8-C14. For example, *Prototheca moriformis* (UTEX 1435), *Prototheca krugani* (UTEX 329), *Prototheca stagnora* (UTEX 1442) and *Prototheca zopfli* (UTEX 1438) contains no (or undetable amounts) C8 fatty acids, between 0-0.01% C10 fatty acids, between 0.03-2.1% C12 fatty acids and between 1.0-1.7% C14 fatty acids.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.025-0.3 mcg/g, preferably from 0.05 to 0.244 micrograms/gram, of oil; chlorophyll A present from 0.025-0.3 mcg/g, preferably from 0.045 to 0.268 micrograms/gram, of oil; total chlorophyll of less than 0.03 mcg/g, preferably less than 0.025 micrograms/gram, of oil; gamma tocopherol present from 35-175 mcg/g, preferably from 38.3-164 micrograms/gram, of oil; total tocopherols present from 50-300 mcg/g, preferably from 60.8 to 261.7 microgram/gram, of oil; less than 0.5%, preferably less than 0.25%, brassicasterol, campesterol, stigmasterol, or betasitosterol; total tocotrienols less than 300 micrograms/gram of oil; and total tocotrienols present from 225-350 mcg/g, preferably from 249.6 to 325.3 micrograms/gram, of oil.

Other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds. In some cases, the oil extracted from a species provided herein comprises between 0.001 to 0.05, preferably from 0.003 to 0.039, microgram lutein/gram of oil, less than 0.005, preferably less than 0.003, micrograms lycopene/gram of oil; and less than 0.005, preferably less than 0.003, microgram beta carotene/gram of oil.

In one aspect, the present invention provides methods for obtaining microbial oil comprising culturing a genetically engineered cell under conditions such that oil is produced. In various embodiments, the microbial oil has a fatty acid profile selected from the group consisting of: 3% to 60% C8:0, 3% to 60% C10:0, 3% to 60% C12:0, 3% to 95% C14:0, 3% to 95% C16:0, 3% to 95% C18:0, 3% to 95% C18:1, 3% to 60% C18:2, 1% to 60% C18:3 or combinations thereof. In various embodiments, the ratio of C10:0 to C12:0 is at least 3:1. In some cases, the ratio of C10:0 to C14:0 is at least 10:1. In various embodiments, the genetically engineered cell has a fatty acid profile of at least 40% saturated fatty acids, of at least 60% saturated fatty acids, or at least 85% saturated fatty acids.

In another aspect, the present invention provides microbial oils and foods, fuels, and chemicals containing said oil or a chemical derived therefrom.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigamsterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g):

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campersterol or 22,23-dihydrobrassicasterol) | 10.7 (1.6%) | 11.9 (1.6%) | 10.9 (1.8%) | 10.8 (1.8%) |
| 4 | 5,22-cholestadien-24-ethyl-3-ol (Stigmaserol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigamsterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol: β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols b-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than b-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

Section VII. Nucleic Acids

In one aspect, the present invention provides recombinant nucleic acids useful in methods for making genetically modified *Prototheca* and other cells. The nucleic acids of the invention comprise all or some portion of a coding sequence of a *C. prototheocoides* lipid biosynthesis gene.

In various embodiments, these nucleic acids include expression cassettes, which consist of a coding sequence and control sequences that regulate expression of the coding sequence, which may code for an mRNA that encodes a lipid biosynthesis enzyme or for an RNAi that acts to suppress expression of a fatty acid biosynthesis gene.

In other embodiments, these nucleic acids are expression vectors that include one or more expression cassettes and stably replicate in a *Prototheca* or other host cell, either by integration into chromosomal DNA of the host cell or as freely replicating vectors.

In other embodiments, these nucleic acids comprise only a portion of a *Prototheca* lipid biosynthesis gene, which portion may be a portion of a coding sequence, an exon, or a control element. Such nucleic acids are useful in the construction of expression cassettes for *Prototheca* and non-*Prototheca* host cells, for integration of exogenous DNA into *Prototheca* host cells, and for construction of nucleic acids useful for inactivating *Prototheca* fatty acid biosynthetic genes by homologous recombination.

EXAMPLES

Example 1

Methods for Culturing *Prototheca*

The methods below can be used to culture *Auxenochlorella* or *Prothetheca* strains. For example, *Prototheca* strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4.7H_2O$, 0.25 g/L Citric Acid monohydrate, 0.025 g/L $CaCl_2$ $2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 6.

TABLE 6

Percent oil by dry cell weight

| Species | Strain | % Oil |
|---|---|---|
| Prototheca stagnora | UTEX 327 | 13.14 |
| Prototheca moriformis | UTEX 1441 | 18.02 |
| Prototheca moriformis | UTEX 1435 | 27.17 |

Microalgae samples from multiple strains from the genus *Prototheca* were genotyped. Genomic DNA was isolated from algal biomass as follows. Cells (approximately 200 mg) were centifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2× iProof HF master mix (BIO-RAD) was added to 0.4 µl primer SZ02613 (5'-TGTTGAAGAATGAGCCGGCGAC-3') (SEQ ID NO: 49105) at 10 mM stock concentration. This primer sequence runs from position 567-588 in GenBank accession no. L43357 and is highly conserved in higher plants and algal plastid genomes. This was followed by the addition of 0.4 µl primer SZ02615 (5'-CAGTGAGCTATTACGCACTC-3') (SEQ ID NO:49106) at 10 mM stock concentration. This primer sequence is complementary to position 1112-1093 in GenBank accession no. L43357 and is highly conserved in higher plants and algal plastid genomes. Next, 5 µl of diluted total DNA and 3.2 µl $dH_2O$ were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 μl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. In total, twelve *Prototheca* strains were selected to have their 23S rRNA DNA sequenced and the sequences are listed in the Sequence Listing. A summary of the strains and Sequence Listing Numbers is included below. The sequences were analyzed for overall divergence from the UTEX 1435 (SEQ ID NO: 5) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below:

| Species | Strain | % nt identity | SEQ ID NO. |
|---|---|---|---|
| *A. prototheocoides* | UTEX 250 | 88.7 | SEQ ID NO: 60 |
| *Prototheca kruegani* | UTEX 329 | 75.2 | SEQ ID NO: 1 |
| *Prototheca wickerhamii* | UTEX 1440 | 99 | SEQ ID NO: 2 |
| *Prototheca stagnora* | UTEX 1442 | 75.7 | SEQ ID NO: 3 |
| *Prototheca moriformis* | UTEX 288 | 75.4 | SEQ ID NO: 4 |
| *Prototheca moriformis* | UTEX 1439; 1441; 1435; 1437 | 100 | SEQ ID NO: 5 |
| *Prototheca wikerhamii* | UTEX 1533 | 99.8 | SEQ ID NO: 6 |
| *Prototheca moriformis* | UTEX 1434 | 75.9 | SEQ ID NO: 7 |
| *Prototheca zopfii* | UTEX 1438 | 75.7 | SEQ ID NO: 8 |
| *Prototheca moriformis* | UTEX 1436 | 88.9 | SEQ ID NO: 9 |

Two other highly conserved plastid regions are the Accd and cyst gene which can be used for phylogenetic comparison. The sequences for these two genes are listed under sequence ID 49109 and 49110 and 49119-49125. They have been observed in all members of the genus *Prototheca* sequenced. The percent sequence identity to UTEX 250 is also included below:

| Species | Strain | % nt identity | SEQ ID NO. |
|---|---|---|---|
| *A prothecoides* | UTEX 250 | 100 | SEQ ID NO: 49119 |
| *zopfii* | SAG 263.7 | 71.5 | SEQ ID NO: 49120 |
| *blaschkaea* | SAG 2064 | 73.5 | SEQ ID NO: 49121 |
| *zopfii* | SAG 263-4 | 73.8 | SEQ ID NO: 49122 |
| *wickerhamii* | SAG 263-11 | 88.2 | SEQ ID NO: 49123 |
| *stagnora* | CBS 605.66 | 75.3 | SEQ ID NO: 49124 |
| *moriformis* | UTEX 376 | 84.5 | SEQ ID NO: 49125 |

Lipid samples from a subset of the above-listed strains were analyzed for fatty acid profile using HPLC. Results are shown below in Table 7.

TABLE 7

Diversity of fatty acid chains in *Prototheca* species

| Strain | C14:0 | C16:0 | C16:1 | C18:0 | C18:1 | C18:2 | C18:3 | C20:0 | C20:1 |
|---|---|---|---|---|---|---|---|---|---|
| *Auxenochlorella prototheocoides* UTEX 250 | 1.07 | 14.82 | | 2.65 | 66.46 | 12.18 | 1.34 | | |
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Oil extracted from *Prototheca moriformis* UTEX 1435 (via solvent extraction or using an expeller press) was analyzed for carotenoids, chlorophyll, tocopherols, other sterols and tocotrienols. The results are summarized below in Table 8.

TABLE 8

Carotenoid, chlorophyll, tocopherol/sterols and tocotrienol analysis in oil extracted from *Prototheca moriformis* (UTEX 1435).

| | Pressed oil (mcg/ml) | Solvent extracted oil (mcg/ml) |
|---|---|---|
| cis-Lutein | 0.041 | 0.042 |
| trans-Lutein | 0.140 | 0.112 |
| trans-Zeaxanthin | 0.045 | 0.039 |
| cis-Zeaxanthin | 0.007 | 0.013 |
| t-alpha-Crytoxanthin | 0.007 | 0.010 |
| t-beta-Crytoxanthin | 0.009 | 0.010 |
| t-alpha-Carotene | 0.003 | 0.001 |
| c-alpha-Carotene | none detected | none detected |
| t-beta-Carotene | 0.010 | 0.009 |
| 9-cis-beta-Carotene | 0.004 | 0.002 |
| Lycopene | none detected | none detected |
| Total Carotenoids | 0.267 | 0.238 |
| Chlorophyll | <0.01 mg/kg | <0.01 mg/kg |
| Tocopherols and Sterols | | |
| | Pressed oil (mg/100 g) | Solvent extracted oil (mg/100 g) |
| gamma Tocopherol | 0.49 | 0.49 |
| Campesterol | 6.09 | 6.05 |
| Stigmasterol | 47.6 | 47.8 |
| Beta-sitosterol | 11.6 | 11.5 |
| Other sterols | 445 | 446 |
| Tocotrienols | | |
| | Pressed oil (mg/g) | Solvent extracted oil (mg/g) |
| alpha Tocotrienol | 0.26 | 0.26 |
| beta Tocotrienol | <0.01 | <0.01 |
| gamma Tocotrienol | 0.10 | 0.10 |
| detal Tocotrienol | <0.01 | <0.01 |
| Total Tocotrienols | 0.36 | 0.36 |

Oil extracted from *Prototheca moriformis*, from four separate lots, was refined and bleached using standard vegetable oil processing methods. Briefly, crude oil extracted from *Prototheca moriformis* was clarified in a horizontal decanter, where the solids were separated from the oil. The clarified oil was then transferred to a tank with citric acid and water and left to settle for approximately 24 hours. After 24 hours, the mixture in the tank formed 2 separate layers. The bottom layer was composed of water and gums that were then removed by decantation prior to transferring the degummed oil into a bleaching tank. The oil was then heated along with another dose of citric acid. Bleaching clay was then added to the bleaching tank and the mixture was further heated under vacuum in order to evaporate off any water that was present. The mixture was then pumped through a leaf filter in order to remove the bleaching clay. The filtered oil was then passed through a final 5 μm polishing filter and then collected for storage until use. The refined and bleached (RB) oil was then analyzed for carotenoids, chlorophyll, sterols, tocotrienols and tocopherols. The results of these analyses are summarized in Table 9 below. "Nd" denotes none detected and the sensitivity of detection is listed below:

Sensitivity of Detection

Carotenoids (mcg/g) nd=<0.003 mcg/g

Chlorophyll (mcg/g) nd=<0.03 mcg/g

Sterols (%) nd=0.25%

Tocopherols (mcg/g); nd=3 mcg/g

TABLE 9

Carotenoid, chlorophyll, sterols, tocotrienols and tocopherol analysis from refined and bleached *Prototheca moriformis* oil.

| | Lot A | Lot B | Lot C | Lot D |
|---|---|---|---|---|
| Carotenoids (mcg/g) | | | | |
| Lutein | 0.025 | 0.003 | nd | 0.039 |
| Zeaxanthin | nd | nd | nd | nd |
| cis-Lutein/Zeaxanthin | nd | nd | nd | nd |
| trans-alpha-Cryptoxanthin | nd | nd | nd | nd |
| trans-beta-Cryptoxanthin | nd | nd | nd | nd |
| trans-alpha-Carotene | nd | nd | nd | nd |
| cis-alpha-Carotene | nd | nd | nd | nd |
| trans-beta-Carotene | nd | nd | nd | nd |
| cis-beta-Carotene | nd | nd | nd | nd |
| Lycopene | nd | nd | nd | nd |
| Unidentified | 0.219 | 0.066 | 0.050 | 0.026 |
| Total Carotenoids | 0.244 | 0.069 | 0.050 | 0.065 |
| Chlorophyll (mcg/g) | | | | |
| Chlorophyll A | 0.268 | 0.136 | 0.045 | 0.166 |
| Chlorophyll B | nd | nd | nd | nd |
| Total Chlorophyll | 0.268 | 0.136 | 0.045 | 0.166 |
| Sterols (%) | | | | |
| Brassicasterol | nd | nd | nd | nd |
| Campesterol | nd | nd | nd | nd |
| Stigmasterol | nd | nd | nd | nd |
| beta-Sitosterol | nd | nd | nd | nd |
| Total Sterols | nd | nd | nd | nd |
| Tocopherols (mcg/g) | | | | |
| alpha-Tocopherol | 23.9 | 22.8 | 12.5 | 8.2 |
| beta-Tocopherol | 3.72 | nd | nd | nd |
| gamma-Tocopherol | 164 | 85.3 | 43.1 | 38.3 |
| delta-Tocopherol | 70.1 | 31.1 | 18.1 | 14.3 |
| Total Tocopherols | 262 | 139.2 | 73.7 | 60.8 |
| Tocotrienols (mcg/g) | | | | |
| alpha-Tocotrienol | 190 | 225 | 253 | 239 |
| beta-Tocotrienol | nd | nd | nd | nd |
| gamma-Tocotrienol | 47.3 | 60.4 | 54.8 | 60.9 |
| delta-Tocotrienol | 12.3 | 16.1 | 17.5 | 15.2 |
| Total Tocotrienols | 250 | 302 | 325 | 315 |

The same four lots of *Prototheca moriformis* oil was also analyzed for trace elements and the results are summarized below in Table 10.

TABLE 10

Elemental analysis of refined and bleached *Prototheca moriformis* oil.

| | Lot A | Lot B | Lot C | Lot D |
|---|---|---|---|---|
| Elemental Analysis (ppm) | | | | |
| Calcium | 0.08 | 0.07 | <0.04 | 0.07 |
| Phosphorous | <0.2 | 0.38 | <0.2 | 0.33 |
| Sodium | <0.5 | 0.55 | <0.5 | <0.5 |
| Potassium | 1.02 | 1.68 | <0.5 | 0.94 |
| Magnesium | <0.04 | <0.04 | <0.04 | 0.07 |
| Manganese | <0.05 | <0.05 | <0.05 | <0.05 |
| Iron | <0.02 | <0.02 | <0.02 | <0.02 |
| Zinc | <0.02 | <0.02 | <0.02 | <0.02 |
| Copper | <0.05 | <0.05 | <0.05 | <0.05 |
| Sulfur | 2.55 | 4.45 | 2.36 | 4.55 |
| Lead | <0.2 | <0.2 | <0.2 | <0.2 |
| Silicon | 0.37 | 0.41 | 0.26 | 0.26 |
| Nickel | <0.2 | <0.2 | <0.2 | <0.2 |
| Organic chloride | <1.0 | <1.0 | <1.0 | 2.2 |
| Inorganic chloride | <1.0 | <1.0 | <1.0 | <1.0 |
| Nitrogen | 4.4 | 7.8 | 4.2 | 6.9 |
| Lithium | <0.02 | <0.02 | <0.02 | <0.02 |
| Boron | 0.07 | 0.36 | 0.09 | 0.38 |
| Aluminum | — | <0.2 | <0.2 | <0.2 |
| Vanadium | <0.05 | <0.05 | <0.05 | <0.05 |
| Lovibond Color (°L) | | | | |
| Red | 5.0 | 4.3 | 3.2 | 5.0 |
| Yellow | 70.0 | 70.0 | 50.0 | 70.0 |
| Mono & Diglycerides by HPLC (%) | | | | |
| Diglycerides | 1.68 | 2.23 | 1.25 | 1.61 |
| Monoglycerides | 0.03 | 0.04 | 0.02 | 0.03 |
| Free fatty acids (FFA) | 1.02 | 1.72 | 0.86 | 0.83 |
| Soaps | 0 | 0 | 0 | |
| Oxidized and Polymerized Triglycerides | | | | |
| Oxidized Triglycerides (%) | 3.41 | 2.41 | 4.11 | 1.00 |
| Polymerized Triglycerides (%) | 1.19 | 0.45 | 0.66 | 0.31 |
| Peroxide Value (meq/kg) | 0.75 | 0.80 | 0.60 | 1.20 |
| p-Anisidine value (dimensionless) | 5.03 | 9.03 | 5.44 | 20.1 |
| Water and Other Impurities (%) | | | | |
| Karl Fisher Moisture | 0.8 | 0.12 | 0.07 | 0.18 |
| Total polar compounds | 5.02 | 6.28 | 4.54 | 5.23 |
| Unsaponifiable matter | 0.92 | 1.07 | 0.72 | 1.04 |
| Insoluble impurities | <0.01 | <0.01 | 0.01 | <0.01 |
| Total oil (%) | | | | |
| Neutral oil | 98.8 | 98.2 | 99.0 | 98.9 |

Example 2

General Methods for Biolistic Transformation of *Auxenochlorella* or *Prototheca*

Seashell Gold Microcarriers (550 nanometers) were prepared according to the protocol from manufacturer. Plasmid (20 μg) was mixed with 50 μl of binding buffer and 60 μl (30 mg) of S550d gold carriers and incubated in ice for 1 min. Precipitation buffer (100 μl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

Prototheca strains were grown in proteose medium (2 g/L yeast extract, 2.94 mM NaNO3, 0.17 mM CaCl2.2H2O, 0.3 mM MgSO4.7H$_2$O, 0.4 mM K2HPO4, 1.28 mM KH2PO4, 0.43 mM NaCl) with 2% glucose on a gyratory shaker until it reaches a cell density of 2×10$^6$ cells/ml. The cells were harvested, washed once with sterile distilled water, and resuspended in 50 µl of medium. 1×10$^7$ cells were spread in the center third of a non-selective proteose media plate. The cells were bombarded with the PDS-1000/He Biolistic Particle Delivery system (Bio-Rad). Rupture disks (1350 psi) were used, and the plates are placed 6 cm below the screen/macrocarrier assembly. The cells were allowed to recover at 25° C. for 12-24 h. Upon recovery, the cells were scraped from the plates with a rubber spatula, mixed with 100 µA of medium and spread on plates containing the appropriate antibiotic selection. After 7-10 days of incubation at 25° C., colonies representing transformed cells were visible on the plates. Colonies were picked and spotted on selective (either antibiotic or carbon source) agar plates for a second round of selection.

Example 3

Fatty Acid analysis by Fatty Acid Methyl Ester Detection

Lipid samples were prepared from dried biomass. 20-40 mg of dried biomass was resuspended in 2 mL of 5% H$_2$SO$_4$ in MeOH, and 200 ul of toluene containing an appropriate amount of a suitable internal standard (C19:0) was added. The mixture was sonicated briefly to disperse the biomass, then heated at 70-75° C. for 3.5 hours. 2 mL of heptane was added to extract the fatty acid methyl esters, followed by addition of 2 mL of 6% K$_2$CO$_3$ (aq) to neutralize the acid. The mixture was agitated vigorously, and a portion of the upper layer was transferred to a vial containing Na$_2$SO$_4$ (anhydrous) for gas chromatography analysis using standard FAME Example 4

Altering the Levels of Saturated Fatty Acids in the Microalgae Auxenochlorella protothecoides or Prototheca moriformis A. Decreasing Stearoyl ACP Desaturase and Delta 12 Fatty Acid Desaturase Expression by a Gene Knockout Approach As part of a genomics screen using a bioinformatics based approach based on cDNAs, Illumia transcriptome and Roche 454 sequencing of genomic DNA from Prototheca moriformis (UTEX 1435), as well as Illumina sequencing of genomic DNA from Auxenochlorella protothecoides, two specific groups of genes involved in fatty acid desaturation were identified: stearoyl ACP desaturases (SAD) and delta 12 fatty acid desaturases (Δ12 FAD). Stearoyl ACP desaturase enzymes are part of the lipid synthesis pathway and they function to introduce double bonds into the fatty acyl chains, for example, the synthesis of C18:1 fatty acids from C18:0 fatty acids. Delta 12 fatty acid desaturases are also part of the lipid synthesis pathway and they function to introduce double bonds into already unsaturated fatty acids, for example, the synthesis of C18:2 fatty acids from C18:1 fatty acids. Southern blot analysis using probes based on the two classes of fatty acid desaturase genes identified during the bioinformatics efforts indicated that each class of desaturase genes was likely comprised of multiple family members. Additionally the genes encoding stearoyl ACP desaturases fell into two distinct families. Based on these results, three gene disruption constructs were designed to potentially disrupt multiple gene family members by targeting more highly conserved coding regions within each family of desaturase enzymes.

Three homologous recombination targeting constructs were designed using: (1) highly conserved portions of the coding sequence of delta 12 fatty acid desaturase (d12FAD) family members and (2) two constructs targeting each of the two distinct families of SAD, each with conserved regions of the coding sequences from each family. This strategy would embed a selectable marker gene into these highly conserved coding regions (targeting multiple family members) rather than a classic gene replacement strategy where the homologous recombination would target flanking regions of the targeted gene.

All constructs were introduced into the cells by biolistic transformation using the methods described above and constructs were linearized before being shot into the cells. Transformants were selected on sucrose containing plates/media and changes in lipid profile were assayed using the above-described method. Relevant sequences from each of the three targeting constructs are listed below.

| Description | SEQ ID NO: |
|---|---|
| 5' sequence from coding region of d12FAD targeting construct | SEQ ID NO: 18 |
| 3' sequence from coding region of d12FAD targeting construct | SEQ ID NO: 19 |
| d12FAD targeting construct cDNA sequence | SEQ ID NO: 20 |
| 5' sequence from coding region of SAD2A | SEQ ID NO: 21 |
| 3' sequence from coding region of SAD2A | SEQ ID NO: 22 |
| SAD2A targeting construct cDNA sequence | SEQ ID NO: 23 |
| 5' sequence from coding region os SAD2B | SEQ ID NO: 24 |
| 3' sequence from coding region of SAD2B | SEQ ID NO: 25 |
| SAD2B targeting construct cDNA sequence | SEQ ID NO: 26 |

Representative positive clones from transformations with each of the constructs were picked and the fatty acid profiles for these clones were determined. Lipid samples were prepared from dried biomass from each transformant and fatty acid profiles from these samples were analyzed using standard fatty acid methyl ester gas chromatography flame ionization (FAME GC/FID) detection methods as described in Example 3. The fatty acid profiles (expressed as Area % of total fatty acids) from the transgenic lines arising from transformation are shown in Table 11.

TABLE 11

Fatty acid profiles of desaturase knockouts.

| Fatty Acid | d12FAD KO | SAD2A KO | SAD2B KO | wt UTEX 1435 |
|---|---|---|---|---|
| C8:0 | 0 | 0 | 0 | 0 |
| C10:0 | 0.01 | 0.01 | 0.01 | 0.01 |
| C12:0 | 0.03 | 0.03 | 0.03 | 0.03 |
| C14:0 | 1.08 | 0.985 | 0.795 | 1.46 |
| C16:0 | 24.42 | 25.335 | 23.66 | 29.87 |
| C18:0 | 6.85 | 12.89 | 19.555 | 3.345 |
| C18:1 | 58.35 | 47.865 | 43.115 | 54.09 |
| C18:2 | 7.33 | 10.27 | 9.83 | 9.1 |
| C18:3 alpha | 0.83 | 0.86 | 1 | 0.89 |
| C20:0 | 0.48 | 0.86 | 1.175 | 0.325 |

Each construct had a measurable impact on the desired class of fatty acid and in all three cases C18:0 levels increased markedly, particularly with the two SAD knockouts. Further comparison of multiple clones from the SAD knockouts indicated that the SAD2B knockout lines had significantly greater reductions in C18:1 fatty acids than the C18:1 fatty acid levels observed with the SAD2A knockout lines.

Additional Δ12 FAD knockouts were generated in a *Prototheca moriformis* background using the methods described above. In order to identify potential homologous of Δ12FADs, the following primers were used in order to amplify a genomic region encoding a putative FAD:

Primer 1  5'-TCACTTCATGCCGGCGGTCC-3' SEQ ID NO: 27

Primer 2  5'-GCGCTCCTGCTTGGCTCGAA-3' SEQ ID NO: 28

The sequences resulting from the genomic amplification of *Prototheca moriformis* genomic DNA using the above primers were highly similar, but indicated that multiple genes or alleles of Δ12FADs exist in *Prototheca*.

Based on this result, two gene disruption constructs were designed that sought to inactivate one or more Δ12FAD genes. The strategy would embed a sucrose invertase (suc2 from *S. cerevisiae*) cassette (SEQ ID NO: 29), thus conferring the ability to hydrolyze sucrose as a selectable marker, into highly conserved coding regions rather than use a classic gene replacement strategy. The first construct, termed pSZ1124, contained 5' and 3' genomic targeting sequences flanking a *C. reinhardtii* β-tubulin promoter (SEQ ID NO: 30) driving the expression of the *S. cerevisiae* suc2 gene (SEQ ID NO: 31) and a *Chlorella vulgaris* nitrate reductase 3'UTR (SEQ ID NO: 32). The second construct, termed pSZ1125, contained 5' and 3' genomic targeting sequences flanking a *C. reinhardtii* β-tubulin promoter driving the expression of the *S. cerevisiae* suc2 gene and a *Chlorella vulgaris* nitrate reductase 3'UTR. The relevant sequences of the constructs are listed in the Sequence Listing:

| | |
|---|---|
| *S. cerevisiae* suc2 cassette | SEQ ID NO: 29 |
| pSZ1124 (FAD2B) 5' genomic targeting sequence | SEQ ID NO: 33 |
| pSZ1124 (FAD2B) 3' genomic targeting sequence | SEQ ID NO: 34 |
| pSZ1125 (FAD2C) 5' genomic targeting sequence | SEQ ID NO: 35 |
| pSZ1125 (FAD2C) 3' genomic targeting sequence | SEQ ID NO: 36 | pSZ1124 and pSZ1125 were each introduced into a *Prototheca moriformis* background. Positive clones were selected based on the ability to hydrolyze sucrose. Table 12 summarizes the fatty acid profiles (in Area %, generated using methods described above) obtained in two transgenic lines in which pSZ1124 and pSZ1125 targeting vectors were utilized.

expected to decrease, only decreased by about one area %. However, the C18:1 fatty acid levels increased significantly, almost exclusively at the expense of the C16:0 levels, which decreased significantly. The transgenic containing the FAD2C (pSZ1125) construct also gave a change in lipid profile: the levels of C18:2 are reduced significantly along with a corresponding increase in C18:1 levels.

B. RNA Hairpin Approach to Down-Regulation of Delta 12 Desaturase (FADc) in *Auxenochlorella* or *Prototheca* Cells Vectors constructed to down-regulate FADc (delta 12 desaturase gene) gene expression by long hairpin RNAs were introduced into a *Prototheca moriformis* UTEX 1435 genetic background. The *Saccharomyces cerevisiae* suc2 sucrose invertase gene was utilized as a selectable marker, conferring the ability to grow on sucrose as a sole-carbon source to positive clones, and two types of constructs were used. The first type of construct utilized a portion of the first exon of the FADc coding region linked in cis to its first intron followed by a repeat unit of the first exon in reverse orientation. This type of construct was designed to form a hairpin when expressed as mRNA. Two constructs of this first type were created, one driven by the *Prototheca moriformis* Amt03 promoter (SEQ ID NO:37), termed pSZ1468, and a second driven by the *Chlamydomonas reinhardtii* β-tubulin promoter (SEQ ID NO:30), termed pSZ1469. The second type of construct utilized the large FADc exon 2 in the antisense orientation driven by either the *Prototheca moriformis* Amt03 promoter (SEQ ID NO:37), termed pSZ1470, or driven by the *Chlamydomonas reinhardtii* β-tubulin promoter (SEQ ID NO:30), termed pSZ1471. All four constructs had a *S. cerevisiae* suc2 sucrose invertase cassette (SEQ ID NO:29) and a 5' (SEQ ID NO:38) and 3' (SEQ ID NO:39) homologous recombination targeting sequences (flanking the construct) to the 6S genomic region for integration into the nuclear genome. Sequences of the FADc portions of each long hairpin RNA construct along with the relevant portions of each construct are listed in the Sequence Listing as:

| Description | SEQ ID NO: |
|---|---|
| pSZ1468 FADc RNA hairpin cassette | SEQ ID NO: 40 |
| Relevant portions of the pSZ1468 construct | SEQ ID NO: 41 |
| pSZ1469 FADc RNA hairpin cassette | SEQ ID NO: 42 |
| Relevant portions of the pSZ1469 construct | SEQ ID NO: 43 |
| pSZ1470 FADc exon 2 RNA hairpin cassette | SEQ ID NO: 44 |
| Relevant portions of the pSZ1470 construct | SEQ ID NO: 45 |
| pSZ1471 FADc exon 2 RNA hairpin cassette | SEQ ID NO: 46 |
| Relevant portions of the pSZ1471 construct | SEQ ID NO: 47 |

Each of the four constructs was transformed into a *Prototheca moriformis* (UTEX 1435) background and positive clones were screened using plates with sucrose as the sole carbon source. Positive clones were picked from each trans-

TABLE 12

Fatty acid profiles of Δ12 FAD knockouts

| | C10:0 | C12:0 | C14:0 | C16:0 | C16:1 | C18:0 | C18:1 | C18:2 | C18:3α |
|---|---|---|---|---|---|---|---|---|---|
| parent | 0.01 | 0.03 | 1.15 | 26.13 | 1.32 | 4.39 | 57.20 | 8.13 | 0.61 |
| FAD2B | 0.02 | 0.03 | 0.80 | 12.84 | 1.92 | 0.86 | 74.74 | 7.08 | 0.33 |
| FAD2C | 0.02 | 0.04 | 1.42 | 25.85 | 1.65 | 2.44 | 66.11 | 1.39 | 0.22 |

The transgenic containing the FAD2B (pSZ1124) construct gave a very interesting and unexpected result in fatty acid profile, in that the C18:2 levels, which would be formation and a subset were selected to determine the impact of the hairpin and antisense cassettes contained in pSZ1468, pSZ1469, pSZ1470 and pSZ1471 on fatty acid profiles. The selected clones from each transformation were grown under lipid producing conditions and the fatty acid profiles were determined using direct transesterification methods as described above. Representative fatty acid profiles from each of the transformations are summarized below in Table 13. Wildtype 1 and 2 cells were untransformed *Prototheca moriformis* (UTEX 1435) cells that were run with each of the transformants as a negative control.

TABLE 13

Fatty acid profiles of *Prototheca moriformis* cells containing long hairpin RNA constructs to down-regulate the expression of delta 12 desaturase gene (FADc).

| Strain | C10:0 | C12:0 | C14:0 | C16:0 | C18:0 | C18:1 | C18:2 |
|---|---|---|---|---|---|---|---|
| wildtype 1 | 0.01 | 0.03 | 1.20 | 27.08 | 4.01 | 57.58 | 7.81 |
| pSZ1468 clone A | 0.01 | 0.04 | 1.33 | 25.95 | 3.68 | 65.60 | 1.25 |
| pSZ1468 clone B | 0.01 | 0.03 | 1.18 | 23.43 | 2.84 | 65.32 | 4.91 |
| pSZ1468 clone C | 0.01 | 0.04 | 1.34 | 23.18 | 4.27 | 63.65 | 5.17 |
| pSZ1468 clone D | 0.01 | 0.03 | 1.24 | 23.00 | 3.85 | 61.92 | 7.62 |
| pSZ1470 clone A | 0.01 | 0.03 | 1.23 | 24.79 | 4.33 | 58.43 | 8.92 |
| pSZ1470 clone B | 0.01 | 0.03 | 1.26 | 24.91 | 4.14 | 57.59 | 9.64 |
| pSZ1470 clone C | 0.01 | 0.03 | 1.21 | 23.35 | 4.75 | 58.52 | 9.70 |
| wildtype 2 | 0.01 | 0.03 | 0.98 | 24.65 | 3.68 | 62.48 | 6.26 |
| pSZ1469 clone A | 0.01 | 0.03 | 1.05 | 21.74 | 2.71 | 71.33 | 1.22 |
| pSZ1469 clone B | 0.01 | 0.03 | 1.01 | 22.60 | 2.98 | 70.19 | 1.27 |
| pSZ1469 clone C | 0.01 | 0.03 | 1.03 | 19.82 | 2.38 | 72.95 | 1.82 |
| pSZ1469 clone D | 0.01 | 0.03 | 1.03 | 20.54 | 2.66 | 70.96 | 2.71 |
| pSZ1471 clone A | 0.01 | 0.03 | 1.03 | 18.42 | 2.63 | 66.94 | 8.55 |
| pSZ1471 clone B | 0.01 | 0.03 | 0.94 | 18.61 | 2.58 | 67.13 | 8.66 |
| pSZ1471 clone C | 0.01 | 0.03 | 1.00 | 18.31 | 2.46 | 67.41 | 8.71 |
| pSZ1471 clone D | 0.01 | 0.03 | 0.93 | 18.82 | 2.54 | 66.84 | 8.77 |

The above results show that the hairpin constructs pSZ1468 and pSZ1469 showed expected phenotypes: a reduction in C18:2 fatty acid levels and an increase in C18:1 fatty acid levels as compared to wildtype 1 and wildtype 2, respectively. The antisense constructs, pSZ1470 and pSZ1471 did not result in a decrease in C18:2 fatty acid levels but instead showed a slight increase when compared to wildtype 1 and wildtype 2, respectively and a slight decrease in C16:0 fatty acid levels.

We provide herein the sequences of *Auxenochlorella* fatty acid desaturase (FAD2 and FAD3). These genes can be used in *Auxenochlorella*, as in the above examples featuring *Prototheca*, in order to increase C18:2 or C18:3 levels through overexpression of FAD2 or FAD3 respectively. They can be used as target regions for homologous recombination, for example to reduce C18:2 accumulation and increase C18:1 levels by knocking out one or both alleles of FAD2, or by introducing a downward promoter in front of FAD2 that will allow for expression of FAD2 during the growth phase, allowing for normal growth, but with FAD2 being shut off during the lipid production phase, to minimize C18:2 levels and increase C18:1 levels.

As just one illustrative example of the above, provided is a vector containing the ACP-P promoter, the ApFAD2 (*Auxenochlorella protothecoides* SAD gene) and the CvNR terminator or other suitable terminator, that is transformed into *Auxenchlorella protothecoides* or *Prototheca* using biolistic transformation as described herein. The cells are then tested for elevated C18:2 levels using standard GC/MS FAME profiling methods as described in this application.

Example 5

Engineered Microalgae with Altered Fatty Acid Profiles

As described above, integration of heterologous genes to attenuate specific endogenous lipid pathway genes, through knockout or knockdown, in *Prototheca* species can alter fatty acid profiles. Plasmid constructs (listed in Table 14) were created to assess whether the fatty acid profile of a host cell may be affected as a result of a knockout an endogenous fatty acyl-ACP thioesterase gene, FATA1.

A classically mutagenized derivative of *Protheca moriformis* UTEX 1435, Strain J, was transformed with one of the following plasmid constructs in Table 14 using the methods of Example 2. Each construct contained a region for integration into the nuclear genome to interrupt the endogenous FATA1 gene and a *S. cerevisiae* suc2 sucrose invertase coding region under the control of *C. reinhardtii* β-tubulin promoter/5'UTR (SEQ ID NO: 30) and *Chlorella vulgaris* nitrate reductase 3' UTR (SEQ ID NO: 32). This *S. cerevisiae* suc2 expression cassette is listed as SEQ ID NO: 29 and served as a selection marker. All protein coding regions were codon optimized to reflect the codon bias inherent in *Prototheca moriformis* UTEX 1435 (see Table 2) nuclear genes. Relevant sequences for the targeting regions for the FATA1 gene used for nuclear genome integration are shown below.

| Description | SEQ ID NO: |
|---|---|
| 5' sequence for integration into FATA1 locus | SEQ ID NO: 48 |
| 3' sequence for integration into FATA1 locus | SEQ ID NO: 49 |

TABLE 14

Plasmid constructs used to transform *Protheca moriformis* (UTEX 1435) STRAIN J.

| Plasmid Construct | Relevant Sequence Elements | SEQ ID NO: |
|---|---|---|
| pSZ1883 | FATA1-CrbTub_yInv_nr-FATA1 | SEQ ID NO: 50 |
| pSZ1925 | FATA1-CrbTub_yInv_nr::amt03_CwTE2_nr-FATA1 | SEQ ID NO: 51 |

To introduce the *Cuphea wrightii* ACP-thioesterase 2 (CwFatB2) gene (Accession No: U56104) into STRAIN J at the FATA1-1 locus, a construct was generated to express the protein coding region of the CwFatB2 gene under the control of the *Prototheca moriformis* Amt03 promoter/5'UTR (SEQ ID NO: 37) and *C. vulgaris* nitrate reductase 3'UTR (SEQ ID NO: 32). Relevant portions of this construct are provided in the Sequence Listing as SEQ ID NO: 51. The codon-optimized cDNA sequences and amino acid sequences of the *Cuphea wrightii* FatB2 thioesterase are listed in the Sequence Listing as SEQ ID NO: 52 and SEQ ID NO: 53, respectively.

Upon transformation of FATA1-CrbTub_yInv_nr-FATA1 into STRAIN J, primary transformants were clonally purified and grown under standard lipid production conditions at pH 5.0 similar to the conditions as disclosed in Example 1. Lipid samples were prepared from dried biomass from each transformant and fatty acid profiles from these samples were analyzed using standard fatty acid methyl ester gas chromatography flame ionization (FAME GC/FID) detection methods as described in Example 3. The fatty acid profiles (expressed as Area % of total fatty acids) from the transgenic lines arising from transformation with pSZ1883 into Strain J are shown in Table 15.

TABLE 15

Fatty acid profiles of *Prototheca moriformis* cells containing a selectable marker to disrupt an endogenous FATA1 allele.

| Transformation | % C14:0 | % C16:0 | % C18:0 | % C18:1 | % C18:2 |
|---|---|---|---|---|---|
| Wildtype | 1.23 | 25.68 | 2.83 | 60.54 | 7.52 |
| Transformant 1 | 0.86 | 16.95 | 1.75 | 68.44 | 9.78 |
| Transformant 2 | 0.85 | 17.33 | 1.71 | 68.57 | 9.31 |
| Transformant 3 | 0.82 | 17.40 | 1.78 | 68.55 | 9.22 |
| Transformant 4 | 0.84 | 17.43 | 1.78 | 68.25 | 9.53 |
| Transformant 5 | 0.75 | 17.64 | 2.02 | 69.02 | 8.61 |

These results show that ablation of the host's endogenous FATA1-1 allele alters the fatty acid profile of the engineered microalgae. The impact of targeting a selectable marker to the endogenous FATA1 allele is a clear diminution of C16:0 fatty acid production with an increase in C18:1 fatty acid production.

Upon transformation of FATA1-CrbTub_yInv_nr::amt03_CwTE2_nr-FATA1 into STRAIN J, primary transformants were clonally purified and grown under standard lipid production conditions at pH 7.0 with different carbon sources provided to a total concentration of 40 g/L. The sucrose concentration was 40 g/L. Where only glucose was used as the carbon source, glucose was provided at 40 g/L. Where glucose and fructose was used as the carbon source, glucse was provided at 20 g/L and fructose was provided at 20 g/L. Lipid samples were prepared from dried biomass from each transformant and fatty acid profiles from these samples were analyzed using standard fatty acid methyl ester gas chromatography flame ionization (FAME GC/FID) detection methods as described in Example 3. The fatty acid profiles (expressed as Area % of total fatty acids) from the transgenic line arising from transformation with pSZ1925 into Strain J are shown in Table 16. The resulting fatty acid profiles are listed in Table 16.

TABLE 16

Fatty acid profiles of *Prototheca moriformis* cells containing a selectable marker and an exogenous thioesterase to disrupt an endogenous FATA1 allele.

| Transformant | | Carbon source | % C10:0 | % C12:0 | % C14:0 | % C16:0 | % C18:0 | % C18:1 | % C18:2 |
|---|---|---|---|---|---|---|---|---|---|
| Strain J | Wildtype | Glucose | 0.01 | 0.04 | 1.38 | 28.83 | 3.00 | 56.05 | 8.21 |
| | Wildtype | Glucose | 0.01 | 0.04 | 1.50 | 29.38 | 3.00 | 55.29 | 8.23 |
| | Wildtype | Glucose/Fructose | 0.01 | 0.05 | 1.48 | 28.58 | 3.20 | 57.14 | 7.27 |
| | Wildtype | Glucose/Fructose | 0.01 | 0.04 | 1.54 | 29.05 | 3.23 | 56.47 | 7.32 |
| >2 copies | 1 | Glucose/Fructose | 4.29 | 19.98 | 9.17 | 20.68 | 3.47 | 34.38 | 6.37 |
| | 2 | Glucose/Fructose | 3.11 | 16.17 | 9.91 | 15.97 | 1.57 | 45.72 | 5.81 |
| | 3 | Sucrose | 4.84 | 24.22 | 11.56 | 19.48 | 2.67 | 29.56 | 6.02 |
| | 4 | Sucrose | 3.24 | 16.67 | 10.39 | 16.34 | 1.43 | 44.41 | 6.00 |
| 1-2 copies | 1 | Glucose/Fructose | 0.18 | 1.64 | 1.85 | 14.43 | 2.12 | 70.30 | 7.63 |
| | 2 | Glucose/Fructose | 0.18 | 1.56 | 1.74 | 13.56 | 2.25 | 71.04 | 7.72 |
| | 3 | Sucrose | 0.19 | 1.69 | 1.89 | 13.79 | 3.15 | 69.97 | 7.68 |
| | 4 | Sucrose | 0.15 | 1.26 | 1.49 | 13.44 | 2.73 | 71.46 | 7.77 |

Concordant with targeting a selectable marker alone to the host's FATA1-1allele, integration of a selectable marker concomitant with an exogenous thioesterase alters the fatty acid profile of the engineered microalgae. As above, targeting an exogenous gene to the FATA1-1 allele results in a clear diminution of C16:0 fatty acid production. The additional expression of the CwTE2 thioesterase at the FATA1-1 locus also impacts mid chain fatty acids and C18:1 fatty acid production to an extent that is dependent upon the level of exogenous thioesterase activity present in the transformants analyzed. Genes bordered by repeat units such as the C. vulgaris nitrate reductase 3' UTR in constructs such as FATA1-CrbTub_yInv_nr::amt03_CwTE2_nr-FATA1, may be amplified upon integration in the host genome. There is good concordance between copy number of the amplified transgene at the target integration site and thioesterase levels as revealed either by impacts on fatty acid profiles or recombinant protein accumulation as assessed by western blotting.

Transgenic lines in which the CwTE2 gene has undergone amplification show a marked increase in mid chain (C10:0-C14:0) fatty acids and a concurrent decrease in C18:1 fatty acids. In contrast, those transformants in which CwTE2 has undergone little or no amplification (likely 1-2 copies) are consistent with lower expression of the exogenous thioesterase, resulting in a slight increase in mid chain fatty acids and a far greater impact on the increase of C18:1 fatty acids.

Collectively, these data show that ablation of the host's endogenous FATAL-1 allele alters the lipid profile of the engineered microalgae. Provided herein is the sequence of the FATA gene of *Axuenochlorella prototehcoides*. As with the *Prototheca*, the FATA gene of *Auxenochlorella protothecoides* can be ablated to alter fatty acid profiles. In addition, heterologous thioesterases, such as the CwFATB2 thioesterase, can be introduced to alter fatty acid profiles to produce mid chain fatty acids. In one non-limiting example, a suitable promoter such as the ACP-P promoter is fused to a plastid transit peptide selected from *A. prototheocoides*, CwFATB2 codon-optimized using the codon optimization table for *A. prototheocoides* and methods provided herein, and a suitable terminator such as the CvNR terminator. This construct is expressed in *A. prototheocoides* and then tested for increased mid-chain fatty acid accumulation.

Example 6

Altering Fatty Acid Profiles of Microalgae Through Overexpression of a an *Auxenochlorella* or *Prototheca* Lipid Biosynthesis Gene As described above, the β-ketoacyl-ACP synthase II (KASII) catalyzes the 2-carbon extension of C16:0-ACP to C18:0-ACP during fatty acid biosynthesis. It is an important lipid biosynthesis enzyme in establishing the fatty acid profile of the host organism and is critical for stearate and oleate production. Plasmid constructs were created to assess whether the fatty acid profile of a host cell may be affected as a result of expression of a KASII gene. Sources of KASII gene sequences were selected from *Protheca moriformis* UTEX 1435 or from higher plants (*Glycine max, Helianthus annus*, or *Ricinus communis*).

A classically mutagenized derivative of *Protheca moriformis* UTEX 1435, STRAIN J, was transformed individually with one of the following plasmid constructs in Table 17 using the methods of Example 2. Each construct contained a region for integration into the nuclear genome at the 6S locus and a *S. cerevisiae* suc2 sucrose invertase coding region under the control of *C. reinhardtii* β-tubulin promoter/5'UTR and *Chlorella vulgaris* nitrate reductase 3' UTR. This *S. cerevisiae* suc2 expression cassette is listed as SEQ ID NO: 29 and served as a selection marker. For each construct, the KASII coding region was under the control of the *Prototheca moriformis* Amt03 promoter/5'UTR (SEQ ID NO: 37) and *C. vulgaris* nitrate reductase 3'UTR (SEQ ID NO: 32). The native transit peptide of each KASII enzyme was replaced with the *Chlorella prototheocoides* stearoyl-ACP desaturase transit peptide (SEQ ID NO: 54). All protein coding regions were codon optimized to reflect the codon bias inherent in *Prototheca moriformis* UTEX 1435 nuclear genes (see Table 2). Relevant sequences for the targeting regions to the 6S locus for nuclear genome integration are shown below.

| Description | SEQ ID NO: |
| --- | --- |
| 5' sequence for integration into 6S locus | SEQ ID NO: 38 |
| 3' sequence for integration into 6S locus | SEQ ID NO: 39 |

TABLE 17

Plasmid constructs used to transform *Protheca moriformis* (UTEX 1435) STRAIN J.

| Plasmid Construct | Source of KASII enzyme | Sequence Elements | SEQ ID. NO: |
| --- | --- | --- | --- |
| pSZ1747 | *Glycine max* | 6S::β-tub:suc2:nr::Amt03:S106SAD:GlmKASII:nr::6S | SEQ ID NO: 55 |
| pSZ1750 | *Helianthus annuus* | 6S::β-tub:suc2:nr::Amt03:S106SAD:HaKASII:nr::6S | SEQ ID NO: 56 |
| pSZ1754 | *Ricinus communis* | 6S::β-tub:suc2:nr::Amt03:S106SAD:RcKASII:nr::6S | SEQ ID NO: 57 |
| pSZ2041 | *Protheca moriformis* | 6S::β-tub:suc2:nr::Amt03:S106SAD:PmKASII:nr::6S | SEQ ID NO: 58 |

The relevant nucleotide sequence of the construct 6S::β-tub:suc2:nr::Amt03:S106SAD:PmKASII:nr::6S is provided in the sequence listings as SEQ ID. NO: 58. Upon individual transformation of each plasmid construct into Strain J, positive clones were screened on plates with sucrose as the sole carbon source. As in the previous examples, primary transformants were clonally purified and grown under standard lipid production conditions. Here, transformants were cultivated at pH 7 and lipid samples were prepared from dried biomass from each transformant as described above. Fatty acid profiles (expressed as Area %) of several positive transformants as compared to a wildtype negative control are summarized for each plasmid construct in Table 18 below.

TABLE 18

Fatty acid profiles of *Prototheca moriformis* cells engineered to overexpress KASII genes.

| Plasmid Construct | KASII Source | Transformant | % C14:0 | % C16:0 | % C18:0 | % C18:1 | % C18:2 |
| --- | --- | --- | --- | --- | --- | --- | --- |
| None | no over-expression | 1 | 1.36 | 28.69 | 2.92 | 56.36 | 8.16 |
| | | 2 | 1.35 | 28.13 | 3.57 | 55.63 | 8.79 |
| | | 3 | 1.22 | 25.74 | 2.82 | 60.6 | 7.31 |
| | | 4 | 1.22 | 25.74 | 2.82 | 60.6 | 7.31 |
| pSZ1747 | Glm | 1 | 2.23 | 25.34 | 2.69 | 57.35 | 9.53 |
| | | 2 | 2.18 | 25.46 | 2.74 | 57.35 | 9.46 |
| | | 3 | 2.18 | 25.33 | 2.89 | 57.34 | 9.5 |
| | | 4 | 2.2 | 25.69 | 2.66 | 57.28 | 9.43 |
| | | 5 | 2.17 | 25.38 | 3.03 | 56.99 | 9.72 |
| pSZ1750 | Ha | 1 | 2.43 | 26.82 | 2.72 | 55.17 | 9.87 |
| | | 2 | 2.44 | 27.14 | 2.62 | 54.89 | 9.81 |
| | | 3 | 2.61 | 26.9 | 2.67 | 54.43 | 10.25 |
| | | 4 | 1.96 | 30.32 | 2.87 | 53.87 | 8.26 |
| | | 5 | 2.55 | 27.64 | 2.98 | 53.82 | 10.07 |

TABLE 18-continued

Fatty acid profiles of *Prototheca moriformis* cells engineered to overexpress KASII genes.

| Plasmid Construct | KASII Source | Transformant | % C14:0 | % C16:0 | % C18:0 | % C18:1 | % C18:2 |
|---|---|---|---|---|---|---|---|
| pSZ1754 | Rc | 1 | 1.84 | 24.41 | 2.89 | 59.26 | 9.08 |
|  |  | 2 | 1.3 | 25.04 | 2.81 | 58.75 | 9.65 |
|  |  | 3 | 1.27 | 25.98 | 2.76 | 58.33 | 9.22 |
|  |  | 4 | 1.95 | 25.34 | 2.77 | 58.15 | 9.22 |
|  |  | 5 | 1.3 | 26.53 | 2.75 | 57.87 | 9.09 |
| pSZ2041 | Pm | 1 | 1.63 | 11.93 | 3.62 | 70.95 | 9.64 |
|  |  | 2 | 1.85 | 11.63 | 3.34 | 69.88 | 10.93 |
|  |  | 3 | 1.84 | 12.01 | 3.81 | 69.56 | 10.45 |
|  |  | 4 | 1.63 | 14.22 | 3.72 | 68.86 | 9.6 |
|  |  | 5 | 1.67 | 15.04 | 3.05 | 68.63 | 9.24 |

The data presented in Table 18 show that none of the higher plant KASII genes effected a change in the fatty acid profile of the transformed microalgal cells. Additional plasmid constructs expressing KASII genes from higher plants driven by promoters other than the *Prototheca* Amt03 promoter also failed to alter fatty acid profiles in transformed cells. In stark contrast, a clear diminution of C16:0 chain lengths with a concomitant increase in C18:1 length fatty acids was observed upon overexpression of the *Prototheca moriformis* KASII gene codon optimized using the codon frequency denoted in Table 2. Similar fatty acid profile changes were observed upon transformation of constructs expressing the PmKASII gene driven by a β-tublin promoter.

These results show that exogenous expression of a *Prototheca* lipid biosynthesis gene can alter the fatty acid profile of genetically engineered microalgae.

The KASII gene and other key lipid biosynthesis genes from *Auxenochlorella protothecoides* are presented here. They provide various uses, for example KASII can be overexpressed to increase accumulation of C18:1 fatty acids.

Example 7

Genetic Engineering of *Chlorella protothecoides* to Express an Exogenous Sucrose Invertase Strains and Media: *Chlorella protothecoides* (UTEX 250) was obtained from the Culture Collection of Alga at the University of Texas (Austin, Tex., USA). The stock cultures were maintained on modified Proteose medium. Modified Proteose medium consists of 0.25 g NaNO$_3$, 0.09 g K$_2$HPO$_4$, 0.175 g KH$_2$PO$_4$ 0.025 g, 0.025 g CaCl$_2$.2H$_2$O, 0.075 g MgSO$_4$.7H$_2$O, and 2 g yeast extract per liter (g/L).

Plasmid Construction: To express the secreted form of invertase in *Chlorella protothecoides*, a *Saccharomyces cerevisiae* SUC2 gene was placed under the control of three different promoters: Cauliflower mosaic virus $^{35}$S promoter (CMV), *Chlorella* virus promoter (NC-1A), and *Chlorella* HUP1 promoter. A yeast SUC2 gene was synthesized to accommodate codon usage optimized for *C. protothecoides* and includes a signal sequence required for directing extracellular secretion of invertase. Each construct was built in pBluescript KS+, and EcoRI/AscI, AscI/XhoI, and XhoI/BamHI sites were introduced to each promoter, invertase gene, and CMV 3'UTR, respectively, by PCR ampilication using specific primers. Purified PCR products were cloned sequentially.

Transformation of *Chlorella protothecoides*: A *Chlorella protothecoides* culture was grown in modified Proteose medium on a gyratory shaker under continuous light at 75 µmol photons m$^{-2}$ sec$^{-1}$ till it reached a cell density of 6×10$^6$ cells/ml.

For biolistic transformation, S550d gold carriers from Seashell Technology were prepared according to the protocol from the manufacturer. Briefly, a linearized construct (20 µg) by BsaI was mixed with 50 µL of binding buffer and 60 µL (3 mg) of S550d gold carriers and incubated in ice for 1 min. Precipitation buffer (100 µL) was added, and the mixture was incubated in ice for another 1 min. After mild vortexing, DNA-coated particles were pelleted by spinning at 10,000 rpm in an Eppendorf microfuge for 10 seconds. The gold pellet was washed once with 500 µL of cold 100% ethanol, pelleted by brief spinning in the microfuge, and resuspended with 50 µL of ice-cold ethanol. After a brief (1-2 sec) sonication, 10 µL of DNA-coated particles were immediately transferred to the carrier membrane. The cells were harvested, washed once with sterile distilled water, resuspended in 50 µL of medium (1×10$^7$ cells), and were spread in the center third of a non-selective Proteous plate. The cells were bombarded with the PDS-1000/He Biolistic Particle Delivery system (Bio-Rad). Rupture disks (1100 and 1350 psi) were used, and the plates were placed 9-12 cm below the screen/macrocarrier assembly. The cells were allowed to recover at 25° C. for 12-24 hours. Upon recovery, the cells were scraped from the plates with a rubber spatula, mixed with 100 µL of medium and spread on modified Proteose plates with 1% sucrose. After 7-10 days of incubation at 25° C. in the dark, colonies representing transformed cells were visible on the plates.

For transformation with electroporation, cells were harvested, washed once with sterile distilled water, and resuspended in a Tris-phosphate buffer (20 m M Tris-HCl, pH 7.0; 1 mM potassium phosphate) containing 50 mM sucrose to a density of 4×10$^8$ cells/mL. About 250 µL cell suspension (1×10$^8$ cells) was placed in a disposable electroporation cuvette of 4 mm gap. To the cell suspension, 5 µg of linearized plasmid DNA and 200 µg of carrier DNA (sheared salmon sperm DNA) were added. The electroporation cuvette was then incubated in an ice water bath at 16° C. for 10 min. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 mL of modified Proteose media, and shaken on a gyratory shaker for 2 days. Following recovery, the cells were harvested at low speed (4000 rpm), resuspended in modified Proteose media, and plated out at low density on modified Proteose plates with 1% sucrose. After 7-10 days of incubation at 25° C. in the dark, colonies representing transformed cells were visible on the plates.

Screening Transformants and Genotyping: The colonies were picked from dark grown-modified Proteose plates with 1% sucrose, and approximately the same amount of cells were transferred to 24 well-plates containing 1 mL of modified Proteose liquid media with 1% sucrose. The cultures were kept in dark and agitated by orbital shaker from Labnet (Berkshire, UK) at 430 rpm for 5 days.

Growth in Liquid Culture: After five days growth in darkness, the genotype-positive transformants showed growth on minimal liquid Proteose media+1% sucrose in darkness, while wild-type cells showed no growth in the same media in darkness.

Example 8

Engineered Microalgae Plastids with Altered Fatty Acid Profiles

As described above, integration of heterologous genes to attenuate specific endogenous lipid pathway genes, through knockout or knockdown, in *Auxenochlorella* or *Prototheca* species can alter fatty acid profiles. Plasmid constructs can be created to assess whether the fatty acid profile of a host cell can be affected as a result of a knockout of an endogenous plastid psaA and insertion of a *Cuphea wrightii* ACP-thioesterase 2 (CwFatB2) gene.

*Auxenochlorella protothecoides* UTEX 250, can be transformed with plasmid constructs. The construct can contain a region for integration into the plastid genome to interrupt the endogenous psaA gene, a neomycin phosphotransferase gene coding region under the control of *Auxenochlorella protothecoides* Accd promoter/5'UTR (SEQ ID NO: 49194) and *Auxenochlorella protothecoides* Accd 3' UTR (SEQ ID NO: 49195) or various other 3' UTR including but not limited to plastid 3'UTRs such as cysT. This *Auxenochlorella protothecoides* plastid expression cassette can serve as a selection marker. All protein coding regions are codon optimized (see Tables 5c-d) to reflect the codon bias inherent in *Auxenochlorella protothecoides* UTEX 250 plastid genes. Relevant sequences for the targeting regions for the psaA gene used for nuclear genome integration are shown below.

| Description | SEQ ID NO: |
| --- | --- |
| 5' sequence for integration into psaA locus | SEQ ID NO: 49192 |
| 3' sequence for integration into psaA locus | SEQ ID NO: 49193 |

To introduce the *Cuphea wrightii* ACP-thioesterase 2 (CwFatB2) gene (Accession No: U56104) into *Auxenochlorella protothecoides* at the psaA plastid locus, a construct can be generated to express the protein coding region of the CwFatB2 gene under the control of the Accd promoter/5'UTR and *Auxenochlorella protothecoides* Accd 3' UTR (SEQ ID NO: 49194). For a selectable marker the neomycin phosphotransferase gene can be included in the cassette. Relevant portions of this construct are provided in the sequence listing as SEQ ID (49192 through 49196). The plastid codon-optimized cDNA sequences and amino acid sequences of the *Cuphea wrightii* FatB2 thioesterase are listed in the Sequence Listing as SEQ ID NO: 49196 and SEQ ID NO: 53, respectively.

Upon transformation of the cassette into *Auxenochlorella protothecoides*, primary transformants can be clonally purified and grown under standard lipid production conditions at pH 5.0 similar to the conditions as disclosed in Example 1. Lipid samples can be prepared from dried biomass from each transformant and fatty acid profiles from these samples are analyzed using standard fatty acid methyl ester gas chromatography flame ionization (FAME GC/FID) detection methods as described in Example 3. The fatty acid profiles (expressed as Area % of total fatty acids) from the transgenic lines arising from transformation should be similar to pSZ1883 transformed into Strain J as shown in Table 16.

These results can show that ablation of the host's endogenous plastid psaA and insertion of *Cuphea wrightii* FatB2 thioesterase alters the fatty acid profile of the engineered microalgae. The impact of targeting a selectable marker to the endogenous psaA and introduction of CwTE2 can alter C18:1 fatty acid production.

Upon transformation of the cassette psaA-pAccd_NeoR_nr::AccD_CwTE2_nr-psaA into *Auxenochlorella protothecoides*, primary transformants can be clonally purified and grown under standard lipid production conditions at pH 7.0 with different carbon sources provided to a total concentration of 40 g/L with a sucrose concentration of 40 g/L. Where only glucose is used as the carbon source, glucose is provided at 40 g/L. Where glucose and fructose are used as the carbon source, glucose is provided at 20 g/L and fructose is provided at 20 g/L. Lipid samples can be prepared from dried biomass from each transformant and fatty acid profiles from these samples can be analyzed using standard fatty acid methyl ester gas chromatography flame ionization (FAME GC/FID) detection methods as described in Example 3. The fatty acid profiles can be altered similarly (expressed as Area % of total fatty acids) from the transgenic line arising from transformation with pSZ1925 into Strain J as shown in Table 17.

Concordant with targeting a selectable marker alone to the host's psaA plastid gene, integration of a selectable marker concomitant with an exogenous thioesterase can alter the fatty acid profile of the engineered microalgae. The additional expression of the CwTE2 thioesterase at the psaA locus may also impact mid chain fatty acids and C18:1 fatty acid production to an extent that is dependent upon the level of exogenous thioesterase activity present in the transformants analyzed. This would be observed to a further extent if the exogenous thioesterase is removed through homologous recombination.

Transgenic lines in which the CwTE2 gene has undergone amplification will show a marked increase in mid chain (C10:0-C14:0) fatty acids and a concurrent decrease in C18:1 fatty acids. In contrast, those transformants in which CwTE2 has undergone little or no amplification (likely 1-2 copies) are consistent with lower expression of the exogenous thioesterase, resulting in a slight increase in mid chain fatty acids and a reduced impact on the decrease of C18:1 fatty acids. When the plastid is targeted for expression of CwTE2 multiple copies may not be necessary as there are already multiple copies of the plastid per cell, and likely multiple copies of the plastid genome per plastid.

Provided herein is the sequence of the psaA plastid gene of *Axuenochlorella protothecoides*. The psaA gene of *Auxenochlorella protothecoides* can be ablated to in order to insert other lipid biosynthesis genes to alter fatty acid profiles. In addition, heterologous thioesterases, such as the CwFATB2 thioesterase, can be introduced to alter fatty acid profiles to produce mid chain fatty acids. In one non-limiting example, a suitable promoter such as the Accd promoter and CwFATB2 codon-optimized using the codon optimization table for *A. protothecoides* plastid and methods provided herein, and a suitable terminator such as the Accd terminator are uesd. This construct can be expressed in *A. protothecoides* and then tested for increased mid-chain fatty acid accumulation.

Provided herein are preferred loci for nuclear integration via homologous recobminatoin in *Auxenochlorella protothecoides*. These loci near KAS1, SAD2, FATA1, Thi4a and FAD sequences are listed under Seq ID: 49197 through 49201. These loci are expected to perform similarly to the data presented for *Prototheca moriformis*. The interruption of these genes will result in changes to the fatty acid profiles similar to the results shown for *Prototheca moriformis*.

Example 9

Engineered Microalgae Plastids with Altered Fatty Acid Profiles

As described above, integration of heterologous genes to attenuate specific endogenous lipid pathway genes, through knockout or knockdown, in *Auxenochlorella* or *Prototheca* species can alter fatty acid profiles. Plasmid constructs can be created to assess whether the fatty acid profile of a host cell can be affected as a result of a knockout of an endogenous plastid psaA and insertion of an *Auxenochlorella protothecoides* Ketoacyl-ACP Synthase II gene (KASII).

*Auxenochlorella protothecoides* UTEX 250 can be transformed with plasmid constructs. The construct can contain a region for integration into the plastid genome to interrupt the endogenous psaA gene, a neomycin phosphotransferase gene coding region under the control of *Auxenochlorella protothecoides* Accd promoter/5'UTR (SEQ ID NO: 49194) and *Auxenochlorella protothecoides* Accd 3' UTR (SEQ ID NO: 49195) or various other 3' UTR including but not limited to plastid 3'UTRs such as cysT. This *Auxenochlorella protothecoides* plastid expression cassette can serve as a selection marker. All protein coding regions are codon optimized (see Tables 5c-d) to reflect the codon bias inherent in *Auxenochlorella protothecoides* UTEX 250 plastid genes. Relevant sequences for the targeting regions for the psaA gene used for nuclear genome integration are shown below.

| Description | SEQ ID NO: |
|---|---|
| 5' sequence for integration into psaA locus | SEQ ID NO: 49202 |
| 3' sequence for integration into psaA locus | SEQ ID NO: 49203 |

To introduce the *Auxenochlorella protothecoides* KetoacylACP-Synthase II gene (Seq ID NO: 49204) into *Auxenochlorella protothecoides* at the psaA plastid locus, a construct can be generated to express the protein coding region of the CwFatB2 gene under the control of the Accd promoter/5'UTR and *Auxenochlorella protothecoides* Accd 3' UTR (SEQ ID NO: 49194). For a selectable marker the neomycin phosphotransferase gene can be included in the cassette. Relevant portions of this construct are provided in the sequence listing as SEQ ID (XX through XX). The plastid codon-optimized cDNA sequences and amino acid sequences of the *Auxenochlorella protothecoides* Ketoacyl-ACP Synthase II are listed in the Sequence Listing as SEQ ID NO: 49204 and SEQ ID NO: 78, respectively.

Upon transformation of the cassette into *Auxenochlorella protothecoides*, primary transformants can be clonally purified and grown under standard lipid production conditions at pH 5.0 similar to the conditions as disclosed in Example 1. Lipid samples can be prepared from dried biomass from each transformant and fatty acid profiles from these samples are analyzed using standard fatty acid methyl ester gas chromatography flame ionization (FAME GC/FID) detection methods as described in Example 3. The fatty acid profiles (expressed as Area % of total fatty acids) from the transgenic lines arising from transformation will be similar to pSZ1883 transformed into Strain J as shown in Table 16.

These results can show that ablation of the host's endogenous plastid psaA and insertion of *Auxenochlorella prothecoides* Ketoacyl-ACP Synthase II alters the fatty acid profile of the engineered microalgae. The impact of targeting a selectable marker to the endogenous psaA and introduction of KASII can alter C18:1 fatty acid production.

Upon transformation of the cassette psaA-pAccd_NeoR_nr::AccD_KASII_nr-psaA into mutagenized *Auxenochlorella protothecoides*, primary transformants can be clonally purified and grown under standard lipid production conditions at pH 7.0 with different carbon sources provided to a total concentration of 40 g/L with a sucrose concentration of 40 g/L. Where only glucose is used as the carbon source, glucose is provided at 40 g/L. Where glucose and fructose are used as the carbon source, glucose is provided at 20 g/L and fructose is provided at 20 g/L. Lipid samples are prepared from dried biomass from each transformant and fatty acid profiles from these samples are analyzed using standard fatty acid methyl ester gas chromatography flame ionization (FAME GC/FID) detection methods as described in Example 3. The fatty acid profiles can be altered similarly (expressed as Area % of total fatty acids) from the transgenic line arising from transformation with pSZ1925 into Strain J as shown in Table 17.

Concordant with targeting a selectable marker alone to the host's psaA plastid gene, integration of a selectable marker concomitant with an exogenous thioesterase can alter the fatty acid profile of the engineered microalgae. The additional expression of the *Auxenochlorella prothecoides* Ketoacyl-ACP Synthase II at the psaA locus can also impact mid chain fatty acids. This would be observed to a further extent if the exogenous KASII is removed through homologous recombination.

Transgenic lines in which the KASII gene has undergone amplification will show a markedly improved conversion from C16:0-ACP to C18:0-ACP fatty acids hence increasing C18:1 levels. In contrast, those transformants in which KASII has undergone little or no amplification (likely 1-2 copies) are consistent with lower expression of the exogenous KASII, resulting in a slight increase in mid chain fatty acids and a reduced impact on the increase of C18:1 fatty acids. When the plastid is targeted for expression of KASII multiple copies may not be necessary as there are already multiple copies of the plastid per cell, and likely multiple copies of the plastid genome per plastid.

Provided herein is the sequence of the psaA plastid gene of *Axuenochlorella prototehcoides*. The psaA gene of *Auxenochlorella protothecoides* can be ablated to in order to insert other lipid biosynthesis genes to alter fatty acid profiles. In addition, heterologous KASII can be introduced to alter fatty acid profiles to produce higher levels of oleic acid. In one non-limiting example, a suitable promoter such as the Accd promoter, the KASII gene codon-optimized using the codon optimization table for *A. protothecoides* plastid and methods provided herein, and a suitable terminator such as the Accd terminator are used. This construct may be expressed in *A. protothecoides* and then tested for increased oleic acid accumulation.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, including GenBank Accession numbers, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09518277B2). An electronic copy of the "Sequence Listing" will also be available from the USPTO upon request and payment of the fee set forth in 37 CFR 1.19(b)(3).

What is claimed is:

1. A recombinant cell transformed with an expression vector that comprises an exogenous nucleic acid encoding the polypeptide of SEQ ID NO:49127.
2. The recombinant cell of claim 1, wherein the nucleic acid is operably linked to a promoter.
3. The recombinant cell of claim 1, wherein the nucleic acid is operably linked to an untranslated control element.
4. The recombinant cell of claim 1, wherein the nucleic acid is operably linked to a sequence encoding a targeting peptide.
5. The recombinant cell of claim 4, wherein the targeting peptide is a transit peptide selected from the group of a plastidial targeting peptide and a mitochondrial targeting peptide.
6. The recombinant cell of claim 1, wherein the nucleic acid is a DNA molecule.
7. The recombinant cell of claim 1, wherein the vector further comprises a nucleic acid that encodes a sucrose invertase.
8. The recombinant cell of claim 1, wherein the cell is a cell of the genus *Prototheca* or *Chlorella*.
9. The recombinant cell of claim 8, wherein the cell is a cell of the species *Chlorella protothecoides*.
10. A method for obtaining microbial oil comprising culturing the recombinant *Chlorella protothecoides* cell of claim 9 under conditions such that oil is produced.

* * * * *